(12) United States Patent
Bonci et al.

(10) Patent No.: US 9,261,508 B2
(45) Date of Patent: Feb. 16, 2016

(54) ANTISENSE RNA FOR TREATING CANCER AND INHIBITION OF METASTASIS AND VECTORS FOR ANTISENSE SEQUESTRATION

(75) Inventors: Desiree Bonci, Perugia (IT); Ruggero De Maria, Rome (IT)

(73) Assignee: Istituto Superiore Di Sanita, Rome (IT)

( * ) Notice: Subject to any disclaimer, the term of this patent is extended or adjusted under 35 U.S.C. 154(b) by 194 days.

(21) Appl. No.: 12/430,737

(22) Filed: Apr. 27, 2009

(65) Prior Publication Data
US 2010/0016406 A1    Jan. 21, 2010

Related U.S. Application Data

(60) Provisional application No. 61/048,047, filed on Apr. 25, 2008.

(51) Int. Cl.
| | | |
|---|---|---|
| *C12Q 1/68* | (2006.01) | |
| *G01N 33/574* | (2006.01) | |
| *A61K 31/7088* | (2006.01) | |
| *C12N 15/113* | (2010.01) | |

(52) U.S. Cl.
CPC ...... *G01N 33/57484* (2013.01); *A61K 31/7088* (2013.01); *C12N 15/113* (2013.01); *C12N 15/1135* (2013.01); *C12N 15/1136* (2013.01); *C12N 2310/11* (2013.01); *C12Q 1/6886* (2013.01); *G01N 2333/4703* (2013.01); *G01N 2333/4739* (2013.01); *G01N 2333/71* (2013.01)

(58) Field of Classification Search
CPC ........................ C12Q 1/6886; A61K 31/7088
USPC ............ 435/6, 91.1, 91.31, 455; 514/1, 2, 44; 536/23.1, 24.5
See application file for complete search history.

(56) References Cited

U.S. PATENT DOCUMENTS

| | | | | |
|---|---|---|---|---|
| 2009/0131356 A1* | 5/2009 | Bader et al. | ...................... | 514/44 |
| 2009/0175827 A1* | 7/2009 | Byrom et al. | ................. | 424/93.2 |

FOREIGN PATENT DOCUMENTS

| | | |
|---|---|---|
| WO | 2005/013901 A2 | 2/2005 |
| WO | 2007/033023 A2 | 3/2007 |

OTHER PUBLICATIONS

Aaltomaa et al. (1999) "Expression of cyclin A and D proteins in prostate cancer and their relation to clinopathological variables and patient survival", Prostate 38(3):175-182.
Almeida et al. (2005) "Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT", J Biol Chem 280(50):41342-41351.
Asangani et al. (published online Oct. 29, 2007) "MicroRNA-21 (miR-21) post-transcriptionally downregulates tumor suppressor Pdcd4 and stimulates invasion, intravasation and metastasis in colorectal cancer", Oncogene 27:2128-2136.
Bartel, D.P. (2004) "MicroRNAs: genomics, biogenesis, mechanism, and function", Cell 116(2): 281-297.
Bello et al. (1997) "Androgen responsive adult human prostatic epithelial cell lines immortalized by human papillomavirus 18", Carcinogenesis 18(6):1215-1223.
Blagosklonny, M.V. (2004) "Antiangiogenic therapy and tumor progression", Cancer Cell 5(1):13-17.
Bonci, et al. (2003) "'Advanced' generation lentiviruses as efficient vectors for cardiomyocyte gene transduction in vitro and in vivo", Gene Ther 10(8):630-636.
Bradbury et al. (1991) "Molecular cloning of PC3, a putatively secreted protein whose mRNA is induced by nerve growth factor and depolarization", PNAS 88:3353-3357.
Calin et al. (2004) "Human microRNA genes are frequently located at fragile sites and genomic regions involved in cancers", PNAS 101(9):2999-3004.
Calin et al. (2006) "MicroRNA signatures in human cancers", Nat Rev Cancer 6(11):857-866.
Calin et al. (2005) "A MicroRNA signature associated with prognosis and progression in chronic lymphocytic leukemia", N Engl J Med 353(17):1793-1801.
Calin et al. (2002) "Frequent deletions and down-regulation of micro-RNA genes miR15 and miR16 at 13q14 in chronic lymphocytic leukemia", PNAS 99(24):15524-15529.
Calin et al. (2004) "MicroRNA profiling reveals distinct signatures in B cell chronic lymphocytic leukemias", PNAS 101(32):11755-11760.
Care et al. (published online Apr. 29, 2007) "*MicroRNA-133* controls cardiac hypertrophy", Nature Medicine 13(5):613-618.
Chan et al. (2005) "MicroRNA-21 Is an Antiapoptotic Factor in Human Glioblastoma Cells" Cancer Res 65(14):6029-6033.
Chang et al. (published online Dec. 9, 2007) "Widespread microRNA repression by Myc contributes to tumorigenesis", Nat Genet 40(1):43-50.
Chesire et al. (2003) "Beta-catenin signaling in prostate cancer: an early perspective", Endocr Relat Cancer 10(4):537-560.
Cimmino et al. (2005) "miR-15 and miR-16 induce apoptosis by targeting BCL2", PNAS 102(39):13944-13949.
Clevers, H. (2006) "Wnt/beta-catenin signaling in development and disease", Cell 127(3):469-80.
Cmarik et al. (1994) "Preferential primary-response gene expression in promotion-resistant versus promotion-sensitive JB6 cells", Mol. Carcinog. 11:115-124.
Colombel et al. (1993) "Detection of the apoptosis-suppressing oncoprotein bc1-2 in hormone-refractory human prostate cancers", Am J Pathol 143(2):390-400.
Cortes et al. (2000) "BTG gene expression in the p53-dependent and -independent cellular response to DNA damage", Mol. Carcinog. 27:57-64.
Dhanasekaran et al. (2001) "Delineation of prognostic biomarkers in prostate cancer", Nature 412(6849):822-826.
Dillhoff et al. (published online Jul. 19, 2008) "MicroRNA-21 is Overexpressed in Pancreatic Cancer and a Potential Predictor of Survival", J Gastrointest Surg. 12(12):2171-2176.
Dong, J.T. (2001) "Chromosomal deletions and tumor suppressor genes in prostate cancer", Cancer Metastasis Rev 20(3-4):173-193.
Dong et al. (2001) "Loss of heterozygosity at 13q14 and 13q21 in high grade, high stage prostate cancer", Prostate 49(3):166-171.

(Continued)

*Primary Examiner* — J. E. Angell
(74) *Attorney, Agent, or Firm* — Lathrop & Gage LLP

(57) ABSTRACT

Provided is the use of antisense RNA and methods for the treatment, diagnosis and prophylaxis of cancer comprising administering said antisense RNA, particularly miRs 15 and 16 to a patient in need thereof.

8 Claims, 22 Drawing Sheets

(56) References Cited

OTHER PUBLICATIONS

Donnellan et al. (1998) "Cyclin D1 and human neoplasia", J. Clin. Pathol. Mol Pathol 51(1):1-7.

Drobnjak et al. (2000) "Overexpression of cyclin D1 is associated with metastatic prostate cancer to bone", Clin Cancer Res 6(5):1891-1895.

Ebert et al. (2007) "MicroRNA sponges: competitive inhibitors of small RNAs in mammalian cells", Nat Methods 4(9):721-726. (Epub, Aug. 12, 2007).

Esquela-Kerscher et al. (2006) "Oncomirs—microRNAs with a role in cancer", Nat Rev Cancer 6(4):259-269.

Farioli-Vecchioli et al. (2007) "Inhibition of medulloblastoma tumorigenesis by the antiproliferative and pro-differentiative gene PC3", FASEB J 21(9):2215-2225. (Epub, Mar. 19, 2007.).

Fei et al. (Nov. 2008) "Inhibitory effects of anti-miRNA oligonucleotides (AMOs) on A549 cell growth", J Drug Target 16(9):688-693.

Felli et al. (2005) "MicroRNAs 221 and 222 inhibit normal erythropoiesis and erythroleukemic cell growth via kit receptor down-modulation", PNAS 102(50):18081-18086.

Ferrara, N. (2004) "Vascular endothelial growth factor: basic science and clinical progress", Endocr Rev. 25(4):581-611.

Ficazzola et al. (2001) "Antiproliferative B cell translocation gene 2 protein is down-regulated post-transcriptionally as an early event in prostate carcinogenesis", Carcinogenesis 22(8):1271-1279.

Fletcher et al. (1991) "Structure and expression of TIS21, a primary response gene induced by growth factors and tumor promoters", J Biol Chem 266:14511-14518.

Fusco et al. (published online Nov. 15, 2007) "Roles of HMGA proteins in cancer", Nat Rev Cancer 7(12):899-910.

Gabriely et al. (published online Jun. 30, 2008) "MiR-21 Promotes Glioma Invasion by Targeting MMP Regulators", Mol Cell Biol. 28(17):5369-5380.

Gao et al. (2006) "Combinatorial activities of Akt and B-Raf/Erk signaling in a mouse model of androgen-independent prostate cancer", PNAS 103(39):14477-14482.

Gleave et al. (1999) "Progression to androgen independence is delayed by adjuvant treatment with antisense Bcl-2 oligodeoxynucleotides after castration in the LNCaP prostate tumor model", Clin Cancer Res 5(10):2891-2898.

Hyytinen et al. (1999) "Three distinct regions of allelic loss at 13q14, 13q21-22, and 13q33 in prostate cancer", Genes Chromosomes Cancer 25(2):108-14.

Jemal et al. (2006) "Cancer statistics 2006", CA Cancer J Clin 56(2):106-130.

John et al. (2004) "Human MicroRNA targets", PLoS Biol 2(11):e363.

Krek et al. (2005) "Combinatorial microRNA target predictions", Nat Genet 37(5):495-500.

Krutzfeldt et al. (2005) "Silencing of microRNAs in vivo with 'antagomirs'", Nature 438(7068):685-689.

Lara et al. (1999) "Treatment options in androgen-independent prostate cancer", Cancer Invest 17(2):137-144.

Lee et al. (published online Feb. 18, 2009) "A 3'-Untranslated Region (3'UTR) Induces Organ Adhesion by Regulating miR-199a Functions", PLOS One 4(2):1-11.

Leung et al. (2001) "Synergistic chemosensitization and inhibition of progression to androgen independence by antisense Bcl-2 oligodeoxynucleotide and paclitaxel in the LNCaP prostate tumor model", Int J Cancer 91(6):846-850.

Lewis et al. (2003) "Prediction of mammalian microRNA targets", Cell 115(7):787-798.

Lewis et al. (2005) "Conserved seed pairing, often flanked by adenosines, indicates that thousands of human genes are microRNA targets", Cell 120(1):15-20.

Lim et al. (published online Oct. 7, 2008) "B Cell translocation Gene 2 Enhances Susceptibility of HeLa Cells to Doxorubicin-Induced Oxidative Damage", J Biol Chem 283(48):33110-33118.

Loberg et al. (2005) "Pathogenesis and treatment of prostate cancer bone metastases: targeting the lethal phenotype", J Clin Oncol 23(32):8232-8241.

Loffler et al., (published online May 11, 2007) "Interleukin-6-dependent survival of multiple myeloma cells involves the Stat3-mediated induction of microRNA-21 through a highly conserved enhancer", Blood 110(4):1330-1333.

McDonnell et al. (1992) "Expression of the protooncogene bcl-2 in the prostate and its association with emergence of androgen-independent prostate cancer", Cancer Res 52(24):6940-6944.

Nakamoto et al. (1992) "Basic Fibroblast Growth Factor in Human Prostate Cancer Cells", Cancer Research 52, 571-577.

Navone et al. (2004) "Isolation and Culture of Prostate Cancer Cell Lines", Methods Mol Med 88:121-130.

Nelson et al. (2006) "RAKE and LNA-ISH reveal microRNA expression and localization in archival human brain", RNA 12(2):187-191.

Nupponen et al. (1998) "Genetic alterations in prostate cancer cell lines detected by comparative genomic hybridization", Cancer Genet Cytogenet 101(1):53-57.

Pienta et al. (2005) "Advances in prostate cancer chemotherapy: a new era begins", CA Cancer J Clin 55(5):300-318.

Raffo et al. (1995) "Overexpression of bcl-2 protects prostate cancer cells from apoptosis in vitro and confers resistance to androgen depletion in vivo", Cancer Research 55(19):4438-4445.

Rouault et al. (1996) "Identification of BTG2, an antiproliferative p53-dependent component of the DNA damage cellular response pathway", Nature Genet. 14:482-486.

Sambrook et al. (1989) "Molecular Cloning", A Laboratory Manual 1.101-1.104, Cold Spring Harbor, Laboratory Press.

Sherr, C.J. (1996) "Cancer cell cycles", Science 274(5293):1672-1677.

Shivakumar et al. (2006) "Bcl-2 gene expression as a predictor of outcome in diffuse large B-cell lymphoma", Clin Lymphoma Myeloma 6(6):455-457.

Si et al. (published online Oct. 30, 2006) "*miR-21*-mediated tumor growth", Oncogene 26:2799-2803.

Singh et al. (published online May 8, 2008) "REST maintains self-renewal and pluripotency of embryonic stem cells", Nature 453(7192):223-227.

Tashiro et al. (2007) "Functions of cyclin D1 as an oncogene and regulation of cyclin D1 expression", Cancer Sci. 98(5):629-635. (Epub Mar. 14, 2007) Review.

Tashiro et al. (2003) "Overexpression of Cyclin D1 Contributes to Malignancy by Up-Regulation of Fibroblast Growth Factor Receptor 1 via the pRB/E2F Pathway1", Cancer Research 63:424-431.

Tolcher et al. (2005) "A phase II, pharmacokinetic, and biological correlative study of oblimersen sodium and docetaxel in patients with hormone-refractory prostate cancer", Clin Cancer Res 11(10):3854-3861.

Verras et al. (2004) "Wnt3a growth factor induces androgen receptor-mediated transcription and enhances cell growth in human prostate cancer cells", Cancer Research 64(24):8860-8866.

Volinia et al. (2006) "A microRNA expression signature of human solid tumors defines cancer gene targets", PNAS 103(7):2257-2261.

Wang et al. (2000) "The Role of Cell Cycle Regulatory Protein, Cyclin D1, in the Progression of Thyroid Cancer", Mod Pathol 13(8):882-887.

Yardy et al. (2005) "Wnt signalling and prostate cancer", Prostate Cancer Prostatic Dis 8(2):119-126.

Yin et al. (1999) "Limiting the location of a putative human prostate cancer tumor suppressor gene at chromosome 13q14.3", Oncogene 18(52):7576-7583.

Yoshino et al. (2006) "Bcl-2 expression as a predictive marker of hormone-refractory prostate cancer treated with taxane-based chemotherapy", Clin Cancer Res 12(20 Pt 1):6116-6124.

Yun et al. (2005) "Both ERK and Wnt/beta-catenin pathways are involved in Wnt3a-induced proliferation", J Cell Sci 118(Pt 2):313-322.

Zhou et al. (2004) "Progression to androgen-independent LNCaP human prostate tumors: cellular and molecular alterations", Int J Cancer 110(6):800-806.

(56) References Cited

OTHER PUBLICATIONS

Zhu et al. (published online Mar. 15, 2007) "MicroRNA-21 Targets the Tumor Suppressor Gene Tropomyosin 1 (*TMB1*)", J Biol Chem 282(19):14328-14336.

Zimmermann et al. (2006) "RNAi-mediated gene silencing in non-human primates", Nature 441(7089):111-114.

Bonci et al. (Oct. 25, 2007) "The *miR-15a/miR-16-1* Cluster Controls Prostate Cancer Progression by Targeting Multiple Oncogenic Activities," Abstract, Congresso Urologia Internazionale.

(Oct. 2007) "Down-Regulation del miR-15 and miR-16 nel cancro alla prostata, Involvement of *miR15-16* Downregulation in Prostate Cancer Development Through the Misregulation of Bcl-2, Cyclin D1 and Wnt3a," Italian language and machine-generated translation.

\* cited by examiner a b

RWPE-2 *in vivo*

Virus injection

Ki67

HeE apoptosi

ANTISENSE RNA FOR TREATING CANCER AND INHIBITION OF METASTASIS AND VECTORS FOR ANTISENSE SEQUESTRATION

CROSS-REFERENCE TO RELATED APPLICATION

This application claims benefit of U.S. Provisional Application 61/048,047, filed Apr. 25, 2008, which application is incorporated by reference to the extent there is no inconsistency with the present disclosure.

FIELD OF THE INVENTION

The present invention relates to the use of antisense RNA, in particular microRNA, and methods for the treatment and prophylaxis of cancer comprising administering said RNA to a patient in need thereof.

INTRODUCTION

Prostate cancer is the most common malignancy in men and one of the leading causes of cancer death[1]. In early stages, androgen ablation is the first line of therapeutic intervention, which induces regression of those tumors that depend on androgens for growth and survival. This therapy is initially effective in the majority of tumors. However, recurrent androgen-independent cancers often develop within 2-3 years[2]. These tumors can be successfully treated by surgery only before the tumor spreads, but no effective treatment has yet been identified to cure the metastatic forms of prostate cancer[2, 3].

SUMMARY OF THE INVENTION

Surprisingly, we have discovered that miR-15 and 16 target not only Bcl2, but also Cyclin D1, Wnt3a and bFGF. Accordingly, by up-modulating miR 15 and/or 16, Cyclin D1, Wnt3a and bFGF can be inhibited. Conversely, by down-modulating miR 15 and/or 16, Cyclin D1, Wnt3a and bFGF inhibition can be lifted.

Thus, in a first aspect, the present invention provides use of antisense RNA, preferably microRNA, specific for all or part of the 3' untranslated region (UTR) of Cyclin D1, Wnt3a and/or bFGF protein mRNA in the treatment, prophylaxis or diagnosis of cancer.

In a further aspect, the present invention provides use of antisense RNA, preferably microRNA, able to specifically bind the 3' untranslated region (UTR) of Cyclin D1, Wnt3a and/or bFGF protein mRNA in the treatment, prophylaxis or diagnosis of cancer.

In a further aspect, the present invention provides a method for the treatment or prophylaxis of cancer, comprising administering to a patient antisense RNA, specific for all or part of 3' untranslated region (UTR) of Cyclin D1, Wnt3a and/or bFGF protein mRNA.

In all aspects, the all or part of the 3' UTR may, in some embodiments, be only part of the 3' UTR. In all aspects, the binding may be specific and preferably, highly specific, measured by hybridisation under highly stringent conditions, as referred to below.

In a further aspect, the present invention provides a method for the inhibition of cancer metastasis, comprising administering to a patient antisense RNA specific for all or part of the 3' untranslated region (UTR) of Cyclin D1, Wnt3a and/or bFGF mRNA.

In a further aspect, the present invention provides a method of diagnosing the presence or status of a cancerous tissue or tumor by determining whether one or more cells from the tissue or tumor express Cyclin D1, Wnt3a and/or FGF. The status of the tissue or tumor may be that the tissue or tumor is metastatic or not metastatic. The presence of Cyclin D1, Wnt3a and/or FGF upregulation, and/or miR 15 and 16 downregulation, either of which are indicative of cancer metastasis. The status of the cancer can be determined and the upregulation of Cyclin D1, Wnt3a and/or FGF, and/or miR 15 and 16 down-regulation, are indicative of a more aggressive phenotype. This allows one to identify, with high probability, tumors which will progress to more advanced or metastatic forms.

The presence of Cyclin D1, Wnt3a and/or bFGF expression in prostate or other cancer metastasis is indicative of an inverse correlation between miR15 and 16 downregulation and target protein up-regulation. In fact, by identifying miR-15 and 16 dis- or down-regulation, one can identify and discriminate those tumors which will become or are metastatic, from those that are or will not become metastatic. This is particularly useful in determining suitable treatment regimes. An important issue concerning therapy choice is that hormonal therapy is effective during early stages of tumor formation but seems contributes to cancer progression when it is applied to advanced forms. Thus, by determining the status of the cancer, a personalised treatment for the patient can be determined.

In certain embodiments applicable to all aspects of the invention unless otherwise apparent, Bcl2 is expressed at a normal level, being a level comparable to a normal cell of the same type, or a weak level, being a level comparable to less than the level of said normal cell of the same type. Thus, the invention can be applicable in all tumors in which Cyclin D1, Wnt3a, Bcl-2 and bFGF are up-regulated but also in cases in which Bcl-2 is expressed at a normal level, being a level comparable to a normal cell of the same type, or a weak level, but not a level indicated or determined to be Bcl2 overexpression.

In embodiment where the cancer is prostate cancer, the cancer treated or identified may be T1-T2 or T2-T3 prostate cancer stages, as these weakly express Bcl-2 (Bcl-2≤10% of total cells) and still express at least one of Cyclin D1, Wnt3a, Bcl-2 and bFGF. This subgroup, based on said stages, is important because is the one that undergoes the change to androgen-independent or metastatic forms, as discussed further below. Moreover the invention includes treatment of prostate metastatic forms that showed Cyclin D1, Wnt3a, Bcl-2 and bFGF-2 up-regulation, provided that Bcl2 is not over-expressed, of course.

In one embodiment, Bcl2 is not overexpressed, being a level greater than the level of said normal cell of the same type. Although cancers in general are encompassed by the invention, in one embodiment, the cell is a prostate cell and the cancer is prostate cancer. In this embodiment, the level of Bcl2 expression is preferably the same, as determined to statistical significance, as a normal, i.e. non-cancerous, prostate cell, and more preferably, less. Levels of Cyclin D1, Wnt3a and/or bFGF expression are preferably higher in the cancerous cells compared to the normal cells. Where reference to a normal cell is made, it will be understood that this is a non-cancerous cell that has not undergone tumorigenesis or oncogenesis. In the case of prostate tissue, this may also include hyperplastic prostate cells.

One way to determine Bcl2 overexpression, in prostate cancer for instance, is to assay, for instance using immunohistochemical techniques, basal cells that express Bcl-2 comparing normal and tumor tissues, preferably form the same patient. In other tumors, Bcl-2 expression is found in a number of cells, so normal and tumoral tissue can be compared, again preferably from the same patient to determine whether Bcl-2 is overexpressed or not.

The cancer may be an uro-genital cancer, preferably kidney and most preferably prostate cancer, although for non-prostate cancer, the invention is not limited to males. Other cancer types envisaged include any of colon, breast, melanoma, and thyroid cancer. The invention also includes any cancer expressing Cyclin D1, Wnt3a and/or bFGF is preferred, especially as these have a much broader prevalence than cancers expressing Bcl2.

Furthermore, the invention involves other kinds of tumors where there is up-regulation of Cyclin D1, Wnt3a and bFGF, but Bcl-2 is not expressed or up-regulated. Indeed, diffuse large B-cell lymphoma (DLBCL) is an aggressive lymphoma with a 5-year survival rate of 35%-60% and patients can be divided in Bcl-2 positive or negative. In addition in thyroid tumors there are Bcl-2 overexpressing or not subgroups. Particularly preferred is the treatment of all kinds of cancer in advanced forms, as Cyclin D1, Wnt3a, Bcl-2 and bFGF-2 are strongly expressed in all kind of metastasis.

MicroRNAs (miRs) are small non-coding single-stranded RNAs of around 22 nucleotides, which negatively regulate gene expression at posttranscriptional level, primarily through base pairing to the 3' untranslated region (UTR) of target mRNAs. Growing evidence indicates that miRs control basic cell functions, ranging from proliferation to apoptosis [4, 5]. Although it has been suggested that miRs are implicated in tumor development and progression [7, 8], few oncogenic miR targets have been identified so far. Interestingly, ~50% of miR genes are located in cancer-associated genomic regions or in fragile sites[9, 10]. miR-15a and miR-16-1 are transcribed as a cluster (miR-15a/miR-16-1) that resides in the region 13q14. Deletions or point mutations at region 13q14 occur with high frequency in chronic lymphocytic leukemia, lymphoma and several solid tumors[10, 11].

WO 2005/013901 discloses a very large number of miR sequences and its contents are hereby incorporated by reference.

The present inventors disclosed the role of miR 15 and 16, targeting Cyclin D1 and Wnt3a, in prostate cancer at the AURO (Italian Urology Association) in Florence, October 2007.

In prostate cancer, the frequency of allelic loss at 13q correlates with tumor progression, rising from 30% to 70% and 90% in early, advanced and metastatic tumors, respectively[12-14]. These observations suggest the existence of tumor suppressor gene(s) involved in prostate carcinogenesis within the 13q14 region. The role of miR-15 and miR-16 in oncogenesis has been highlighted in previous studies showing that their transcripts are absent or downregulated in a significant fraction of B-cell chronic lymphocytic leukemia [15], resulting in the upregulation of the antiapoptotic gene Bcl-2, whose mRNA is targeted by both miR-15 and miR-16 [16].

Increased Bcl-2 expression protects prostate cancer cells from apoptosis induced by androgen withdrawal and chemotherapeutic drugs, thus facilitating tumor progression towards androgen independence and resistance to conventional therapy[17]. The ability of miR-15 and miR-16 to target Bcl-2 may partially explain the oncogenic effect of 13q14 deletion. However, since single microRNAs can target multiple mRNAs [4], the loss of miR-15 and miR-16 may hypothetically increase the expression of other proteins promoting cell proliferation and transformation.

The possibility that miR-15a and miR-16 act as tumor suppressor genes in prostate cancer might have considerable implications for both elucidation of the oncogenic mechanisms underlying tumor progression and the development of innovative therapies based on miR delivery in defective tumors. Therefore, we examined the expression of miR-15a and miR-16 in prostate cancer, and the functional consequence of altered expression of these microRNAs in tumor and untransformed prostate cells.

Croce et al (WO 2007/033023) disclose the role of miRs 15 and 16 in treating prostate cancer in which Bcl2 is overexpressed. However, we have shown that miR 15 and/or 16 can be used to target a broader range of proteins, belonging to three separate signalling pathways (Cyclin D1, Wnt3a and/or FGF). As Cyclin D1 and Wnt3a are oncogenes, we have shown that miR 15 and/or 16 are tumor suppressor genes and therefore useful in tumor suppression. As such, miR 15 and/or 16 has a much broader applicability than just prostate cancer. Croce et al did not disclose or hint at these targets or to the broader applicability of the use of these miRs to target many cancers.

In fact, Croce suggests that only Bcl-2 overexpressing tumors can be treated, whereas we have shown that the miRs can be used to treat tumors in which Cyclin D1, bFGF and/or Wnt3a are expressed. As mentioned above, it is preferred that Bcl-2 is expressed at normal levels or below and, more preferably not over-expressed.

Our data demonstrated the specific function of the Cyclin D1, Wnt3a, bFGF and Bcl2 genes revealing that Bcl-2 alone does not cause tumour progression. Indeed, Bcl-2 is only responsible for resistance to apoptosis (cell death). Bcl-2 inhibition alone is, therefore, not sufficient to block cancer, despite the reports of Croce.

Moreover, we can extend the results on the interaction between tumor and stroma which is known to support tumor progression. In fact miRs 15 and/or 16 are not expressed in prostate stroma, such as shown by in situ hybridization assay, reported herein. Tumor prostate fibroblasts express Cyclin D1 (ref 48, 49) and miR-15-16 overexpression reduced bFGF expression (ref 53,55 and our data not yet published), and in addition bFGF is a new target of miR15-16 (we validated bFGF as miR15-16 target, our data not yet published. Of course Bcl-2 is expressed by fibroblasts but the role of Cyclin D1 is clear from the literature.

bFGF and FGF-R1 (the bFGF receptor) were shown to be new targets for miR15 and/or miR16 by Luciferase assay and western blotting. Fibroblasts, isolated from prostate cancer primary cultures, showed that miRNA treatment blocked their growth in terms of proliferation. Moreover, co-culture of tumor cells and miR-15 and/or 16 treated stroma showed a consistent reduction in tumor growth in vitro and in vivo, indicating an important role of miRNA also in microenviroment control. The scientific community has great attention on microenviroment conditioning by tumors. In fact many anticancer drugs are directed at blocking the interaction between cancer and stroma. miRNA treatment can, therefore, block growth of the tumor itself and the also its stroma support. This is useful for all kinds of tumors.

This data was reconfirmed by in vivo co-injection of different tumor cells (RWPE-2, LNCaP, PC3) and stroma treated with miR-15a and -16. The results showed a consistent reduction in tumor growth, indicating an important role of miRNA in microenviroment control. Furthermore, a bioinformatic analysis and identified other possible targets of miR-15 and miR-16 involved in neo-angiogenesis, metastasis and aggressiveness: VEGF-A, HMGA-1, HMGA-2. Thus, these are also preferred targets of the present invention.

Vascular endothelial growth factor A (VEGFA or VEGF) is an essential growth and survival factor for endothelial cells. It plays a major role in physiological and pathological angiogenesis through its ability to stimulate growth of new blood vessels from nearby capillaries (ref.60,61). Its sequence is given in SEQ ID NO: 1 (the 3'UTR binding site position is present within ntds1748-3625).

The high mobility group A (HMGA) non-histone chromatin proteins alter chromatin structure and thereby regulate the transcription of several genes by either enhancing or suppressing transcription factors. This protein family is implicated, through different mechanisms, in both benign and malignant neoplasias. Rearrangements of HMGA genes are a feature of most benign human tumours. Conversely, unrearranged HMGA overexpression is a feature of malignant tumours and is also causally related to neoplastic cell transformation (ref.62). The sequence of HMGA2 is given in SEQ ID NO: 2 (the 3' UTR binding site position is at position 1302-1308).

The sequence of HMGA-1 is given in SEQ ID NO: 3 (the 3' UTR binding site positions are 1019-1025 and 1022-1028).

bFGF is synonymous for FGF-2. Basic fibroblast growth factor, also known as bFGF or FGF2, is a member of the fibroblast growth factor family. Therefore, it is envisaged that all cellular growth factors associated with cell division and replication may also be targeted, especially those listed below.

FGF1, FGF2, FGF3, FGF4, FGF4, FGF5, FGF6, FGF7, FGF8, FGF9 and FGF10 all bind fibroblast growth factor receptors (FGFRs). FGF1 is also known as "Acidic", and FGF2 is also known as basic fibroblast growth factor. Members FGF11, FGF12, FGF13, and FGF14, also known as FGF homologous factors 1-4 (FHF1-FHF4), have been shown to have distinct functional differences compared to the FGFs. Although these factors possess remarkably similar sequence homology, they do not bind FGFRs and are involved in intracellular processes unrelated to the FGFs. Members FGF16 through FGF23 are newer and not as well characterized. FGF-15 is the mouse ortholog of human FGF-19. Fibroblast growth factors that bind to fibroblast growth factor receptors are particularly preferred.

Up-modulating miRs 15 and/or 16 (down-modulation of Cyclin D1, Wnt3a and/or FGF) may be achieved, for instance, by administering or increasing expression of miRs 15 and/or 16, for instance administering it directly or in the form of a vector with a coding sequence for miRs 15 and/or 16 preferably under the control of a suitable promoter, or by reducing antagomir (anti-miRs 15 and/or 16) levels.

Conversely, down-modulating miRs 15 and/or 16 (up-modulation of Cyclin D1, Wnt3a and/or bFGF) may be achieved, for instance, by increasing antagomir (anti-miRs 15 and/or 16) levels, for instance using a vector with a coding sequence for anti-miRs 15 and/or 16, preferably under the control of a suitable promoter.

Provided is a method of diagnosing the presence or status of a cancerous tissue or tumor by determining whether one or more cells from the tissue or tumor express Cyclin D1, Wnt3a and/or bFGF. The status of the tissue or tumor may be that the tissue or tumor is metastatic or not metastatic. The presence of Cyclin D1, Wnt3a and/or FGF is indicative of cancer metastasis. Furthermore, the downregulation of miRs 15 and/or 16 is also indicative of the progression of a tumor to an advanced stage. By determining the metastatic status of the tissue and/or by detecting the downregulation of miRs 15 and/or 16, a decision can be reached as to the treatment regimen that is most suited to the particular patient. Said regimen may include surgery (such as removal of all or part of the tissue (for instance a prostatectomy for prostate tissue), a chemotherapeutic, hormone treatment and/or a radiation treatment regimen.

For prostate tissues, identification of the metastatic status of the tissue and/or the detection of the downregulation of miRs 15 and/or 16 can aid the decision as to whether hormone treatment (such as androgen ablation) or a prostatectomy is required. Thus, a personalized treatment regime can be tailored to the individual patient. Indeed, there is a need in the art for a marker of this sort, particularly in prostate cancer, One of the invasive processes of Prostate Cancer (abbreviated in English as PCa or CaP in Italian) is characterised by a step associated with the interaction of between the tumour cells and the surrounding tissues (ref 55, 56). Metastatic prostate cancer is a leading source of cancer-related death in men. Although most patients will respond to androgen ablation as an initial systemic therapy, nearly all patients will develop androgen-independent prostate cancer (Al PCa) and will succumb to the disease (resulting in death). Prostate metastatic tissue expresses Cyclin D1 (ref 56), Bcl2 (ref 58) Wnt3a (evidence from a PC-3 line which is a prostate metastasis from bone) and/or bFGF (ref 52, 53). Croce et al is completely silent on this. LNCaP cells, as used herein, have been isolated by a lymphonodal metastasis (ref 59). Since miRs 15 and/or 16 treatment produced tumor regression in vitro and in vivo, the present invention is useful is blocking inhibition of metastasis, which is applicable over a broad range of tumors.

Particularly preferred stages of cancer progression for treatment and/or diagnosis by the present invention are pre-metastatic tumours or tissues, i.e. benign or hyperplastic tissues that have yet to metastasise.

In particular, the cancer is at a T1-T2 or T2-T3 stage. This is especially the case for prostate cancers. In this embodiment, the T1-T2 or T2-T3 stage cancers are also preferably androgen-sensitive cancers, in other words, they are responsive to androgen ablation. As we have shown, only 50% of the patients analysed in this group have downregulation of miRs 15 and/or 16. Nevertheless, this subgroup is also reported (ref 50) to weakly express Bcl2 (about 10% or less, see table 2 of ref 50 incorporated herein by reference) but does express Cyclin D1. This subgroup is important as it often progress to advanced, Androgen-independent or metastatic forms of cancer.

The 50% of T2 samples, as identified therein, showing miR downregulation are believed to be samples expressing Bcl2 at only normal levels (i.e. not over-expressing Bcl2) and which do express Cyclin D1. The advanced forms are T3-T4 and 80% of these included patients that did show miRs 15 and/or 16 downregulation. Thus, these subgroups are a preferred patient of the invention, particularly patients with cancer at the T1-T2 or T2-T3 stage.

Preferably, Bcl2 is expressed at only minimal levels and is mot preferably not overexpressed. Bax and Bak are expressed in some cancers where Bcl2 is not overexpressed. Thus, it is preferred that the cancers treated or diagnosed by the invention do express Bax and/or Bak. In particular, there are still 30% of Bcl2-expressing tumors (which is a large number of patients given the prevalence of prostate cancer for instance) between stages T2 and T3 that do not overexpress Bcl2 and only partially express Bak and Bax. Furthermore, these cancers do not respond to treatment with taxanes. Thus, tissues or tumors that at least partially express Bak and/of Bax and, optionally, which are not responsive to treatment with taxanes, are preferred. As Croce focuses on Bcl2 over-expression, these tissues or tumors were not considered by Croce.

In normal or hyperplastic prostate epithelium Cyclin D1 is weakly expressed. In T1 and T2 stages only 50% of cells expressed Cyclin D1 (in this group 50% of cases with miR15-16 showed down-regulation) reaching 90% in T3 and T4 (T3 cases were used in our work) (TabII ref.50). Bcl-2 is known to be over expressed in advanced cancer (T3-T4) (TabII ref. 50). In the article a study involving 120 patients reports (TabII) that Bcl-2 is weakly expressed in about 76 Cyclin D1 positive and 44 negative patients in early stages. In 44 Bcl-2 over expressed patients (advanced Stages), about 41 have up-regulation of Cyclin D1 (Tab II. Ref 50). The paper by Yoshino reports that Bcl-2 is strongly associated with advanced cancer above all hormone therapy refractory prostate cancer. The Bcl-2 expressing tumors can be treated with taxanes, but there is a 30% of cases between T2-T3 that do not over express Bcl-2 and only partially express Bak and Bax, these do not answer to taxanes (Ref. 51).

Where reference is made to "miR 15" this includes miR 15, miR 15a and miR15b, which differ in their "seed" position. Most preferred is miR-15a (SEQ ID NO. 4).

Where reference is made to "miR 16" this includes miR16-2 and miR 16-1. miR-16 has two sequences mapping into two different Chromosome, miR-16-1 and miR-16-2, which are perfectly the same. In the examples, reference is made to miR-16-1. miR 16 is SEQ ID NO: 5.

Preferably, the therapy is via Cyclin D1, Wnt3a and/or FGF down-modulation or inhibition, particularly by posttranscriptional control of Cyclin D1, Wnt3a and/or FGF by miRs 15 and/or 16.

Where reference is made to miRs 15 and/or 16, it will be understood that miR 15 can be used alone, or miR 16 can be used alone, or a mixture of both of said miRs may be used. Similar considerations apply to the anti-miR sequences and, indeed to reference to Cyclin D1, Wnt3a and/or FGF, where one, at least one, two or all three may be targeted.

It is preferred that the antisense RNA is a micro RNA. Preferably, the antisense RNA has at least 60% homology with a selected region of the 3' untranslated region of Cyclin D1, Wnt3a and/or FGF protein mRNA. Preferably, the antisense RNA is between about 12 bases and 45 bases in length.

The antisense RNA is preferably a sequence having the same sequence as mature miRs 15 and/or 16, which is preferably the RNA sequence of SEQ ID NO 4 (mature miR 15 5'-UAGCAGCACAUAAUGGUUUGUG-3'), or SEQ ID NO. 5, miR 16 (5'-U AGCAGCACGUAAAUAUUGGCG-3'), NCBI accession: miR15-miR16 NCBI:ch13:49519256:49523338. In both miRs, the seed sequence is shown in bold and underlined.

Where a sequence capable of inhibiting miRs 15 and/or 16 is required (anti-miR 15 and/or anti-miR 16, antagomirs), its sequence is preferably the RNA sequence of SEQ ID NO 6 (anti-miR-15: 5'CACAAACCATTATGTGCTGCTA3') or SEQ ID NO. 7 (anti-miR-16 5'-CGCCAATATTTACGTGCT-GCTA 3') or their RNA equivalents.

The nucleotide sequence of:
human Cyclin D1 is (>gi|77628152|ref|NM_053056.2| *Homo sapiens* cyclin D1 (CCND1) mRNA) SEQ ID NO. 9;
Wnt3a (>gi|7017978|ref|NM_033131.2| *Homo sapiens* wingless-type MMTV integration site family, member 3A (WNT3A), mRNA) is SEQ ID NO. 10; and
FGF (>gi|153285460|ref|NM_002006.4| *Homo sapiens* fibroblast growth factor 2 (basic) (FGF2), mRNA) is SEQ ID NO. 11.

The nucleotide sequence of Bcl2 is provided in SEQ ID NO.12 (>gi|72198188|ref|NM_000633.2|*Homo sapiens* B-cell CLL/lymphoma 2 (BCL2), nuclear gene encoding mitochondrial protein, transcript variant alpha, mRNA)

The sequence of FGF2 is provided at accession number: NM_002006. That of FGF-R1 is provided at accession number: NM_023110, as SEQ ID NO. 13. (>gi|105990515|ref|NM_015850.3|*Homo sapiens* fibroblast growth factor receptor 1 (fms-related tyrosine kinase 2, Pfeiffer syndrome) (FGFR1), transcript variant 2, mRNA)

The antisense RNA is preferably specific for all or part of the 3' UTR of Cyclin D1, Wnt3a and/or FGF protein mRNA. Preferably, it is specific for the full length 3' UTR of Cyclin D1, Wnt3a and/or bFGF mRNA. Preferably, it is specific for at least one, and preferably both, of the following putative miRs 15 and/or 16 binding sites, as indicated in FIG. 13 (for Wnt3a, both contained between bp 2026-2932; for Cyclin D1, both contained between bp 3044-4079).

The seed sequences can be seen highlighted below. They are also further discussed herein.

```
miR-15
5' U AGCAGCA CAUAAUGGUUUGUG 3' miR-16
5' U AGCAGCA CGUAAAUAUUGGCG 3'

IN BOLD: SEED
```

The binding and alignment of miRs 15 and 16 with respect to Wnt3a, Cyclin D1 ad bFGF is shown below:

```
Wnt3a NM_033131.2:
Site 1
Position 1771-1778 of WNT3A 3' UTR (SEQ ID NO:
       14) with hsa-miR-15a 5'...UAAUGUUAUAUCUGAUGCUGCUA...
              ||   |||||||
   3'   GUGUUUGGUAAUACACGACGAU
Position 1771-1778 of WNT3A 3' UTR (SEQ ID NO:
       14) with hsa-miR-16

5'...UAAUGUUAUAUCUGA-UGCUGCUA...
              ||||   |||||||
   3'   GCGGUUAUAAAUGCACGACGAU
Site 2
Position 1426-1432 of WNT3A 3' UTR (SEQ ID NO:
       15) with hsa-miR-15a 5'...UCAACCCCCCGACUGUGCUGCUC...
          ||||       |||||||
   3' GUGUUUGGUAAUAC---ACGACGAU
Position 1426-1432 of WNT3A 3' UTR (SEQ ID NO:
       15) with hsa-miR-16

5'...UCAACCCCCCGACUGUGCUGCUC...
              ||  |||||||
   3'   GCGGUUAUAAAUGC-ACGACGAU
Cyclin D1 NM_053056
Site 1
Position 1961-1967 of CCND1 3' UTR (SEQ ID NO:
       16) with hsa-miR-16

5'...CCAUUUUCUUAUUGC---GCUGCUAC...
              ||||   |||||||
   3'       GCGGUUAUAAAUGCACGACGAU
Position 1961-1967 of CCND1 3' UTR (SEQ ID NO:
       16) with hsa-miR-15a 5'...CCAUUUUCUUAUUGCGCUGCUAC...
              ||||    ||||||
   3'   GUGUUUGGUAAUACA-CGACGAU
```

-continued

Site 2
Position 2033-2040 of CCND1 3' UTR (SEQ ID NO: 17) with hsa-miR-15a

```
5'...CUCUUUCACAUUGUUUGCUGCUA...
        ||||    |||||||
3'      GUGUUUGGUAAUACACGACGAU
```

Position 2033-2040 of CCND1 3' UTR (SEQ ID NO: 17) with hsa-miR-16

```
5'...CUCUUUCACAUUGUU-UGCUGCUA...
        |||     |||||||
3'      GCGGUUAUAAAUGCACGACGAU
``` bFGF (NM_002006);
Site 1
Position 5599-5606 of FGF2 3' UTR (SEQ ID NO: 18) with hsa-miR-16

```
5'...UAAUUUAAAAUAUUU---UGCUGCUA...
        |||||||       |||||||
3'      GCGGUUAUAAAUGCACGACGAU
```

Position 5599-5606 of FGF2 3' UTR (SEQ ID NO: 18) with hsa-miR-15a

```
5'...UAAUUUAAAAUAUUU--UGCUGCUA...
        |||     |||||||
3'      GUGUUUGGUAAUACACGACGAU
```

Position 5640-5647 of FGF2 3' UTR (SEQ ID NO:19) with hsa-miR-16

```
5'...GAAGAAUCUUACAGAUGCUGCUA...
        |||     |||||||
3'  GCGGUUAUAAAUGC--ACGACGAU
```

Position 5640-5647 of FGF2 3' UTR (SEQ ID NO:19) with hsa-miR-15a

```
5'...GAAGAAUCUUACAGAUGCUGCUA...
        |||     |||||||
3'  GUGUUUGGUAAUAC--ACGACGAU
```

FGF-R1; (NM_015850)
Position 886-892 of FGFR1 3' UTR (SEQ ID NO:20) with hsa-miR-16

```
5'...UCCCUCAAUAAAAAU-UGCUGCUG...
        ||||    |||||||
3'      GCGGUUAUAAAUGCACGACGAU
```

Position 886-892 of FGFR1 3' UTR (SEQ ID NO:20) with hsa-miR-15a

```
5'...UCCCUCAAUAAAAAUUGCUGCUG...
        ||       |||||||
3'  GUGUUUGGUAAUAC -ACGACGAU
```

Position 889-895 of FGFR1 3' UTR (SEQ ID NO:21) with hsa-miR-15a

```
5'...CUCAAUAAAAAUGC-UGCUGCUU...
        |||     |||||||
3'      GUGUUUGGUAAUACACGACGAU
```

Position 889-895 of FGFR1 3' UTR (SEQ ID NO:21) with hsa-miR-16

```
5'...CUCAAUAAAAAUGCUGCUGCUU...
        |||||       |||||||
3'      GCGGUUAUAAAUGC--ACGACGAU
```

Thus, it can be seen that FGF-R1 is also targeted by miRs 15 and/or 16. Therefore, the present invention also includes antisense nucleotides that target FGF-R1 and methods of diagnosis based on FGF-R1 upregulation. Indeed, where reference is made to bFGF, it will be understood that this applies to FGF-R1 as well, unless otherwise apparent.

Also provided is an inhibitor or suppressor (antagomir) of miRs 15 and/or 16. Preferably, this is a sense RNA. The invention provides for the use of this inhibitor or suppressor in therapy, preferably in mediation, and preferably stimulation, of oncogenesis, particularly in prostate cancer cells. This is particularly useful in creating suitable cell line and cancer models.

The sense RNA preferably hybridises to miRs 15 and/or 16 under highly stringent conditions, such as 6×SSC.

Also provided is a vector comprising the present antisense or antagomir RNA, or DNA encoding said RNA. Preferably, the vector encodes or comprises the mature form of the RNA, where the RNA is a micro RNA.

To determine the possible involvement of miR15 and 16 loss in prostate malignancies, we first analysed miR-15 and miR-16 expression in prostate cancer cells and tissues. Real Time PCR and in situ hybridization showed that miR-15 and miR-16 were significantly downregulated in about 80% of the 20 tumors analyzed, as compared with normal prostatic tissue from the same patients. Similarly, miR-15 and miR-16 expression was ten-fold lower in cancer than in normal prostate cell lines. This data reinforced the hypothesis that miR-15 and miR-16 can act as tumor suppressor genes. Therefore, we engineered a lentiviral vector (decoy-miR15-16) containing multiple complementary matching sequences for miRs sequestration and silencing, which allowed us to obtain complete silencing of miRs 15 and 16 in the normal prostate cell line RWPE-1. This is the so-called "decoy" viral vector and forms an aspect of the present invention.

Interestingly, decoy-miR15-16 RWPE-1 infected cells recapitulated prostate tumor phenotype in terms of increased growth, cell cycle acceleration, adhesion-independent growth in soft-agar, invasiveness and resistance to chemotherapy-induced apoptosis. Likewise, transduction of normal prostate cells with decoy-miR15-16 resulted in increased survival and proliferation, suggesting that downregulation of miR-15 and miR-16 may contribute to prostate cancer development and progression.

Moreover, we transduced primary prostate cancer cells and the LNCaP cell line with a lentiviral vector containing the cluster miR15-16 to obtain expression levels compatible to those observed in normal cells. Importantly, restoring the expression of miR15-16 in tumor cells resulted in growth arrest, spontaneous apoptosis and increased sensitivity to chemotherapeutic drugs.

Since the modulation of Bcl-2 expression is the natural explanation of the different apoptosis sensitivity, we searched for new target genes of miR-15 and miR-16 that could promote cell proliferation and invasion. Using target prediction software and luciferase reporter assays, we found that miR-15 and miR-16 could directly target the 3'-untranslated region of the Cyclin D1 and Wnt3a mRNAs, two key mediators of the oncogenic process. Accordingly, exogenous expression of the cluster miR15-16 in prostate tumor cells resulted in a considerable downregulation of Bcl-2, Cyclin D1 and Wnt3a at the protein level, while decoy-miR15-16 promoted the expression of Bcl-2, Cyclin D1 and Wnt3a in normal prostate cells. Targeting of miR15-16 conferred tumorigenic potential to RWPE-1 cells, which differently from wild-type cells were able to grow and form tumors in immunodeficient NOD-SCID mice. In contrast, LNCaP-generated tumors underwent growth arrest and massive apoptosis upon lentiviral delivery of miR-15 and miR-16 within the tumor mass. Thus, miR-15 and miR-16 can act as tumor suppressor genes in prostate cancer through the control of cell survival and proliferation. This feature has considerable therapeutic implications and may be exploited in the future for novel treatments of prostate cancer.

Therefore, the delivery of nucleotides capable of silencing miRs, leading to miR downregulation, and delivery of nucleotides capable of upregulating miRs, are provided. Although we have shown that such delivery is effective for miRs 15 and 16, this delivery method is fully expected to work in the upregulation or downregulation of all miRs, particularly those described in WO 2005/013901, incorporated herein by reference.

Thus, in a further aspect, the invention also provides a transducable construct comprising at least one mRNA sequence, or a DNA sequence encoding said mRNA sequence, together with a suitable promoter therefore, the at least one DNA sequence or the encoded mRNA sequence being capable of hybridising to a microRNA sequence. Also provided is a transducable construct comprising at least one DNA sequence, encoding an mRNA sequence, and a suitable promoter therefore, the at least one DNA sequence or the encoded mRNA sequence being capable of hybridising to a microRNA sequence. The promoter is preferably operably linked to the at least one DNA sequence or encoded an mRNA sequence.

Therefore, if the miR reads 5'-AUGC-3' (only for the purposes of an example), then the DNA sequence in the vector would read 5'-GCAT-3'.

Complementary sequences can bind and sequester miRNA but it is also possible to create antisense sequences with some modifications. In particular, certain stretches may have lower levels of complementarity than others (in the dsRNA). For instance, it is possible to create a "bulge" between nucleotide 9-11, in the 22 miRNA bp structure, which leads to loss cleavage of the dsRNA by RNAse enzymes. Positions 9-11 are the preferred site for RNAse cleavage. Such modifications avoiding perfect matching in these positions, thus forming a bulge in one stand of the dsRNA. The RNAse enzyme is only able to cleave the dsRNA if it detects perfect complementarity between positions 9-11. The use of either "perfect" or "bulged" antisense sequences, either separately or simultaneously is envisaged.

The vector may contain multiple repeated sequences (multiple complementary matching sequences), each capable of sequestering and silencing a microRNA (miR) sequence. These sequences may be the same (i.e multiple repeats) or different (i.e. two or more complementary sequences targeting different miRs). In addition, where any one single complementary sequence is present, this may be provided as a tandem repeat, with the optional spacer, as described herein.

For instance, if the complementary sequence for a first miR is represented by "A", the complementary sequence for a second miR is represented by "B" and the complementary sequence for a third miR is represented by "C", then the following arrangements are possible:
A-B-C or A-spacer-A-B-spacer-B-C-spacer-C- or A-B-spacer-B-C or A-spacer-A-B-spacer-B-B-spacer-B-C-spacer-C-

It will be appreciated that these are examples only and many other arrangements are possible. The use of differing numbers of complementary sequences for particular miRs allows varying degrees of specificity to be designed by the skilled physician, depending on the therapeutic state of the patient. In other words, the arrangement of complementary sequences can be tailored to the needs of the patient, under a personalised treatment.

The promoter may be tissue specific so as to allow greater targeting of the treatment. Type Pol II, Pol III promoters are also useful.

In some embodiments, the complementary sequences may be or encode antagomirs, being sequences substantially complementary to a miR over their entire length (or at least over a roughly 22 bp stretch). Specific antagomir examples for miRs 15, 16 and 21, for instance are provided above and also below:

```
                          (miR-15; miR-16 (SEQ ID NO: 22))
5'GCACAAACCATTATGTGCTGCTAAGAGAACTTAGAGAACTTCACAAAC
CATTATGTGCTGCTAT 3'

(miR-21 (SEQ ID NO: 23))
5'TCAACATCAGTCTGATAAGCTAAGAGAACTTAGAGAACTTTCAACATC
AGTCTGATAAGCTA 3'
```

Delivery is preferably by a viral vector. The viral vector may be retrovirus, such as a lentivirus, or an adenovirus.

Thus, the invention provides delivery, by a viral vector, of the above-mentioned at least one DNA sequence or the encoded mRNA sequence (referred to hereinafter as "complementary sequences" as they are preferably complementary to the microRNAs (miRs) of interest).

The complementary sequences, preferably arranged in tandem, and preferably separated by a spacer, form a "unit."

The complementary sequences may inserted into an untranslated region of a gene, the gene being part of a construct or cassette which is then delivered by the vector. When transduced, a host cell will express the complementary sequence and therefore silence any miR already present in that cell. The vector is preferably the viral capsid and does not comprise any viral or other polynucleotides, other than the present construct.

In the present Examples, and in some preferred embodiments, we use a lentiviral vector. The Lavoro et al Nature Medicine paper (Nature Medicine vol 13 number 5 may 2007, incorporated herein by reference) uses a similar system, wherein the vector is an adenoviral vector. Either are preferred. The untranslated region is preferably the 5' UTR or, most preferably, the 3' UTR of the DNA or RNA gene.

The gene into which the unit is positioned is preferably a marker gene. Preferred marker genes include fluorescent protein markers such as enhanced cyan fluorescent protein (ECFP), DsRed fluorescent protein, enhanced green fluorescent protein (EGFP), enhanced yellow (EYFP) and Green Fluorescent Protein, preferably from *Aequorea victoria*.

It is also preferred to use the same structure, preferably only sequence repetition in tandem, with a terminator signal cloned in a vector with a pol II or a pol III promoter, thereby obviating the need for a reporter gene.

The sequences are preferably complementary or bulged. However, it is particularly preferred that the sequences are perfectly complementary to the miR in the seed region. This is as described herein, where the "decoy" structure is able to block miR16 (as can bee seen in FIGS. 9 and 10). It will be appreciated that miR16 and miR15 may have only the 80% sequence homology to their target over their full length but, as preferred, have 100% homology in with the seed sequence. The decoy sequence is designed on miR-15.

Decoy sequences based on 100% of complementarity, such as in the case of miR133 (as shown in Lavoro et al, supra, Nat. Med) or miR 15, are useful.

Furthermore, the use of bulged sequences, particularly for miR16, is also useful. In such bulged sequences, the matching sequence for miR sequestration is complementary for only 80% of the total, but in this case the seed sequence must be perfectly complementary. Sharp et al (Nat Methods. 2007 September;4(9):721-6. Epub Aug. 12, 2007) confirms this and uses sequences in tandem cloned in an expression vector without a reporter. Thus, the use of a reporter is preferred when tandem sequences are used.

The complementary sequences in the unit are preferably arranged in tandem, as mentioned above, but may also be arranged in triplet, quadruplet, or in a series of 5, 6 or more repeats.

The spacer is preferably between 18-22 nucleotides in length and most preferably 22 nucleotides in length. Where more than one complementary sequences is provided, it is preferred that there is a spacer between each complementary sequence in a series. Multiple copies of the unit, comprising the complementary sequences, are also envisaged.

The construct is a genetic element and is adapted for expression in a host cell, most preferably a human cell. The vector may be suitably formulated for administration intramuscularly, intravenously, orally, transdermally or transmucosally.

The construct is transducable, in the sense that it can be expressed in the host cell. Hybridisation is preferably under stringent conditions, preferably highly stringent conditions, preferably 6×SSC.

The term "hybridization under stringent conditions" is defined according to Sambrook et al., Molecular Cloning, A Laboratory Manual, Cold Spring Harbor, Laboratory Press (1989), 1.101-1.104. Preferably, hybridization under stringent conditions means that after washing for 1 h with 1.times.SSC and 0.1% SDS at 50 degrees C., preferably at 55 degrees C., more preferably at 62 degrees C. and most preferably at 68 degrees C., particularly for 1 h in 0.2.times.SSC and 0.1% SDS at 50 degrees C., preferably at 55 degrees C., more preferably at 62 degrees C. and most preferably at 68 degrees C., a positive hybridization signal is observed.

The vector may also comprise a cloning site which allows the insertion of foreign nucleic acid fragments. Further, it is preferred that the cloning site is a multiple cloning site comprising recognition sites for a plurality of restriction enzymes, which e.g. may be selected from the group consisting of NcoI, KpnI, Acc651, XmaI, SmaI, SmaI, EcoRI, XhoI, NotI, EcoRV and SalI.

Suitable miRs are those disclosed in WO 2005/013901, for instance. It is particularly preferred that the miR is miR 15, miR 16, 21 or any combination thereof. If more than one miR is to be silenced, then the complementary sequences for each miR are preferably spaced apart, or provide within separate constructs or even separate vectors.

Antisense RNA may be specific for any part of the 3' UTR of Cyclin D1, Wnt3a and/or FGF protein mRNA, and it will be appreciated that the 3' UTR may vary slightly from individual to individual.

In a further aspect, the invention provides an oligonucleotide comprising at least one 3'UTR of a gene encoding a protein, the 3'UTR comprising a binding sight for a microRNA sequence that inhibits expression of said protein.

Lee et al (reference 12 below) disclose the delivery of a 3'UTR, the 3'UTR comprising a binding sequence for miR199*. This was shown to induce organ adhesion in transgenic mice due to miR sequestration. However, no specific derepression was shown. No data was collected on other targets of miR199*, other than the two proteins of interest in the study, Versican and Fibronectin.

In a still further aspect, the invention provides an oligonucleotide comprising a coding sequence for a first protein, said coding sequence comprising at least one 3'UTR of a gene encoding a second protein, the 3'UTR comprising a binding sight for a microRNA sequence that inhibits expression of said second protein.

There may be more than one 3'UTR, which could be multiple repeats of 3'UTRs from the same gene (which in themselves could vary, provided that they all at least comprise the miR binding site). Alternatively, the 3'UTRs may be from different genes.

The binding site may consist of the "seed" sequence of a particular miR. Alternatively, the binding site may include the seed sequence and any number of other nucleotides complementary to the corresponding miR, up to the full complementary sequence for the miR (usually around 22 bp), in which case, the complementary sequence is fully complementary i.e. is a "sense" version of the antisense miR sequence. All that is required is that the miR can bind to the miR binding site, although suitable levels of hybridisation are also provided above.

Any binding site for a miR is envisaged, as above. Particularly preferred are biding sites for miRs 15, 16 and/or 21. Suitable 3'UTRs can be found using bioinformatic analysis.

Where two one or more 3'UTRs are used, these may have binding sites for different miRs or have differing specificities for the same miR, or a combination of both. Where the 3'UTRs have differing specificities for the same miR, this may be achieved by varying the secondary structure of the remaining oligonucleotide outside the miR binding site. In turn, this may be achieved by selecting different variants or homologues of the same gene, whose 3'UTRs may therefore vary slightly, or this can be designed, i.e. certain secondary structures can be introduced by suitable modulation of the surrounding sequences. The overall specificity of a miR for a particular 3'UTR is determined by both the binding site specificity and the surround secondary structure, much as in the same away as the variation in antigen specificity is determined by the CDRs and the surrounding structure of an antibody binding site.

Where two one or more 3'UTRs are used, and these have binding sites for different miRs, then this allows for multiple therapeutic targets to be included, as discussed further above.

The 3'UTR may comprise as many as 100, 200, 300, 400, 500, 600, 800, 1000, 1500 or even 2000 bp, but around 400 is particularly preferred.

The oligonucleotide may also comprise a suitable promoter, such as those mentioned above. Particularly preferred are tissue-specific promoters or inducible promoters, such as the CMV promoter or hsp promoter.

The first protein may be a marker, for instance. Suitable examples are given above. This transgene may, therefore, be expressed in the presence of the miR.

The present oligonucleotide may be thought of as a chimaeric oligonucleotide.

The second protein may be a therapeutic target. Without being bound by theory, it is believed that a chimaeric oligonucleotide comprising a coding sequence with a heterologous 3'UTR inserted therein, leads to expression of the coding sequence (transgene) in the presence of the miR whilst simultaneously de-repressing the endogenous gene (that encoding the second protein) with which the inserted 3'UTR is associated (or was derived). The chimaera is thought to sequester (or "squelch") the miR and therefore compete with the endogenous gene for said miR, thus reducing the repressive effect of the miR on the expression of the endogenous gene.

The skilled physician may monitor and count the number of transcripts of the oligonucleotide, so that the effect on other targets of said miR can be assessed and monitored. This can be via real-time PCR, for instance.

Each miR is likely to have multiple different in vivo gene targets, but the miR will have different specifies for each, for the reason discussed above. It is surprising that the present oligonucleotide selects the therapeutic target for de-repression (by lifting the inhibitory effect of the miR on that particular protein). Other targets of the same miR are not generally affected in the sense that their levels of repression by said miR remain substantially unchanged, as shown for instance in FIG. 17.

The vector may also comprise a resistance gene, such as puromycin, so allow selection of transduced cells.

In a preferred example, the miR is miR 21, which has the following sequence (SEQ ID NO: 24):

```
5'UAGCUUAUCAGACUGAUGUUGA3'  miR-21
```

In this instance, the 3'UTR is that of BTG2. The sequence of BTG2 is given in SEQ ID NO: 25 and an example of a BTG2 3'UTR is provided. The BTG2 3'UTR binding site is at position 2039-2045.

```
                                           (SEQ ID NO:8)
5' ...GUAGUAGUAUGUUUGUAAGCUAU...3'BTG-2UTR
                 ||||||
3'     AGUUGUAGUCAGACUAUUCGAU miR-21
```

Also provided is a vector comprising the oligonucleotide. The vector may be a viral vector, in particular a Lentiviral vector as discussed above. The oligonucleotide may be under a suitable promoter, as also discussed above.

The invention also provides a method of reducing miR-mediated inhibition of expression of a protein of interest, comprising administering the above oligonucleotide or vector. In this instance, the second protein of the oligonucleotide is the protein of interest.

Also provided is a method of inhibiting cancer metastasis or treating cancer, comprising administering to a patient an antisense RNA, preferably miRs 15 and/or 16, to thereby inhibit Cyclin D1, Wnt3a and/or FGF expression.

Alternatively, also provided is a method of stimulating cancer metastasis, stimulating oncogenesis or removing tumor suppression, comprising administering to a patient an antagomir of miRs 15 and/or 16 or nucleotides encoding it, to thereby increase Cyclin D1, Wnt3a and/or FGF expression.

In addition, as noted above, the miR(s) need not be 100% faithful to the target, sense sequence. Indeed, where they are 100% faithful, this can lead to cleavage of the target mRNA through the formation of dsRNA. While the formation of dsRNA and cleavage of Cyclin D1, Wnt3a and/or FGF protein mRNA is included within the scope of the present invention, it is not a requirement that the antisense RNA be 100% faithful to the target sequence, provided that the antisense RNA is capable of binding the target 3' UTR to inhibit or prevent translation.

Thus, it will be appreciated that the antisense RNA of the present invention need only exhibit as little as 60% or less homology with the target region of the 3' UTR. More preferably, the antisense RNA exhibits greater homology than 60%, such as between 70 and 95%, and more preferably between 80 and 95%, such as around 90% homology. Homology of up to and including 100%, such as between 95 and 100%, is also provided. Suitable methods for assessment of such homology include the BLAST program.

The antisense RNA of the present invention may be as long as the 3' UTR, or even longer. The preferred miR is miRs 15 and/or 16, according to SEQ ID NO.1 or 2. Its mature length is of 22 bases. However, it is generally preferred that the antisense RNA is no longer than 50 bases, and it may be a short as 10 bases, for example. More preferably, the antisense RNA of the present invention is between about 12 bases and 45 bases in length, and is more preferably between about 15 and 35 bases in length. Thus, a particularly preferred length is between 20 and 25 bases, and especially 22.

The area of the 3' UTR to be targeted may be any that prevents or inhibits translation of the ORF, when associated with an antisense RNA of the invention. The particularly preferred regions are those targeted miRs 15 and/or 16, and targeting either of these regions with antisense RNA substantially reduces translation of Cyclin D1, Wnt3a and/or FGF protein.

Regions of the 3' UTR that it is preferred to target include the central region of the 3' UTR and regions between the central region and the ORF. Such regions, which are proximal to the ORF, are particularly preferred. Other Cyclin D1, Wnt3a and/or FGF mRNA sequences, such as the coding region for instance, may also be targeted. It is preferred that the antisense RNA of the present invention is a short interfering RNA or a micro RNA.

The present invention further provides mutants and variants of miRs 15, 16 and/or 21. In this respect, a mutant may comprise at least one of a deletion, insertion, inversion or substitution, always provided that the resulting miR is capable of interacting with the 3' UTR to inhibit or prevent translation of the associated coding sequence. Enhanced homology with the 3' UTR is preferred. A variant will generally be a naturally occurring mutant, and will normally comprise one or more substitutions.

Particularly preferred stretches of the microRNA of the present invention correspond to the so-called "seed" sequences. (such as indicated in FIG. 13) and above. In particular, the seed is "AGCAGCA".

It will be appreciated that reference to any sequence encompasses mutants and variants thereof, caused by substitutions, insertions or deletions, having levels of sequence homology (preferably at least 60%, more preferably at least 70%, more preferably at least 80%, more preferably at least 90%, more preferably at least 95%, more preferably at least 99%, and most preferably at least 99.5% sequence homology), or corresponding sequences capable to hybridising to the reference sequence under highly stringent conditions (preferably 6×SSC or as defined above).

The antisense RNAs of the present invention may be provided in any suitable form to the target site. In this respect, the target site may be in vivo, ex vivo, or in vitro, for example, and the only requirement of the antisense RNA is that it interacts with the target 3' UTR sufficiently to be able to inhibit or prevent translation of the Cyclin D1, Wnt3a and/or FGF ORF.

The antisense RNA may be provided directly, or a target cell may be transformed with a vector encoding the antisense RNA directly, or a precursor therefor. Suitable precursors will be those that are processed to provide a mature miR, although it is not necessary that such precursors be transcribed as long primary transcripts, for example.

Where the antisense RNA is provided directly, then this may be provided in a stabilised form such as is available from Dharmacon, Boulder, Colo., USA.

A large number of microRNAs are known from WO 2005/013901, the patent specification of which alone is over 400 pages. However, no specific function is provided therefor.

Thus, although microRNAs are known, we are the first to establish that naturally-occurring RNA sequences, in particular miRs 15 and/or 16, or inhibitors thereof, are in fact capable of modulating the expression of Cyclin D1, Wnt3a and/or FGF protein.

Insofar as miRs 15 and/or 16 is known, and any stabilised versions thereof, such as provided by Dharmacon are known, then the present invention does not extend to these compounds per se. However, the present invention extends to these and all other antisense RNAs provided by the present invention, for use in therapy and other processes.

More particularly, the present invention provides the use of antisense RNA specific for all or part of the 3' untranslated region of miRs 15 and/or 16 protein mRNA in therapy.

The nature of the therapy is any that is affected by expression of Cyclin D1, Wnt3a and/or FGF proteins. In particular, antisense RNAs of the present invention may be used in the treatment of Cyclin D1, Wnt3a and/or FGF-expressing tumours, preferably those not overexpressing Bcl2.

Solid, non-diffuse tumours may be targeted by direct injection of the tumour with a transforming vector, such as lentivirus, or adenovirus. If desired, the virus or vector may be labelled, such as with FITC (fluorescein isothiocyanate), in order to be able to monitor success of transformation.

Thus, it is also preferred that the present invention is used in the modulation of oncogenesis and/or inhibition of cancer metastasis, most preferably of the prostate.

For the treatment of a more diffuse condition, then systemic administration may be appropriate, and antisense RNA may be administered by injection in a suitable vehicle, for example.

Levels of antisense RNA to be administered will be readily determined by the skilled physician, but may vary from about 1 µg/kg up to several hundred micrograms per kilogram.

The present invention further provides miRs 15 and/or 16 inhibitors, and their use in therapy. These are referred to as "sense inhibitors" in that they are complementary, at least in part, to the antisense miRNA of the present invention.

Also provided is the use of a sense or antisense polynucleotide according to present invention in the manufacture of a medicament for the treatment or prophylaxis of the conditions specified herein.

Suitable inhibitors for miRs 15 and/or 16 include antibodies and sense RNA sequences capable of interacting with these miRs. Such sense RNAs may correspond directly to the concomitant portion of the 3' UTR of Cyclin D1, Wnt3a and/or FGF mRNA, but there is no requirement that they do so. Indeed, as miRs frequently do not correspond entirely to the 3' UTR that they target, while the existence of dsRNA often leads to destruction of the target RNA, then it is a preferred embodiment that the inhibitor of miRs 15 and/or 16 is entirely homologous for the corresponding length of miRs 15 and/or 16. The length of the inhibitor need not be as long as miRs 15 and/or 16, provided that it interacts sufficiently at least to prevent either of these miRs interacting with the 3' UTR or Cyclin D1, Wnt3a and/or FGF mRNA, when so bound.

Conditions treatable by miRs 15 and/or 16 inhibitors include those associated with downmodulation of CXCR4, thereby requiring upregulation of Cyclin D1, Wnt3a and/or FGF.

Preferred methods of delivery of the antisense miRNA or sense inhibitors may be by any gene therapy method known in the art, as will be readily apparent to the skilled person. Such methods include the so-called "gene-gun" method or delivery within viral capsids, particularly adenoviral or lentiviral capsids encapsulating or enclosing said polynucleotides, preferably under the control of a suitable promoter.

Preferred means of administration by injection include intravenous, intramuscular, for instance. However, it will also be appreciated that the polynucleotides of the present invention can be administered by other methods such as transdermally or per orally, provided that they are suitably formulated.

Also provided is a "test kit" capable of testing the level of expression of the Cyclin D1, Wnt3a and/or FGF protein such that the physician or patient can determine whether or not levels of the CXCR4 protein should be increased or decreased by the sense or antisense sequences of the present invention.

The present invention also encompasses a polynucleotide sequence, particularly a DNA sequence, which encodes the microRNAs of the present invention, operably linked to a suitable first promoter so that the microRNAs can be transcribed in vivo. Similarly, the present invention also provides a polynucleotide, particularly DNA, providing polynucleotides encoding the sense microRNA inhibitors of the present invention, also operably linked to a suitable second promoter for in vivo expression of said sense microRNA inhibitors.

In particular, it is also preferred that the first and second promoters mentioned above can be controlled by a third element, such that the level of expression of the antisense microRNA and the level of expression of the sense microRNA inhibitors can be controlled in a coordinated manner. In this regard, it is preferred that a feedback mechanism is also included for establishing this level of control.

Chimeric molecules are also provided, consisting of a polynucleotide according to the present invention, i.e. the antisense microRNAs or the sense microRNA inhibitors, linked to a second element. The second element may be a further polynucleotide sequence or may be a protein sequence, such as part or all of an antibody. Alternatively, the second element may have the function or a marker so that the location of microRNAs can be followed.

Thus, miRs 15 and/or 16 and antagomirs thereof are useful in controlling or mediating expression of Cyclin D1, Wnt3a and/or FGF and controlling or mediating cancer metastasis or oncogenesis.

Treatment may also include at least one chemotherapeutic agent, for instance docatexatel.

All reference cited herein are hereby incorporated by reference, unless otherwise apparent.

The invention will now be described with reference to the Examples and the accompanying Figures.

a) miR-15a and miR-16 expression was analyzed by real time PCR in primary cells isolated by cancer prostate samples from 20 patients diagnosed with prostatic adenocarcinomas. miR levels were evaluated as relative expression over those of cells from normal prostate tissues (dotted line). Real time PCR data are mean values of four independent experiments performed in duplicated. b) In situ hybridization analysis of miR-15a and miR-16 expression in normal and tumor prostatic tissues (magnification 40×). c) Hematoxylin-Eosin staining (left) and detection of miR-15a and miR-16 by in situ hybridization (central and right) in serial sections from prostatic adenocarcinoma. Tumor (red arrows) and non-neoplastic prostate epithelial cell areas (black arrows) are indicated.

Figure 2:
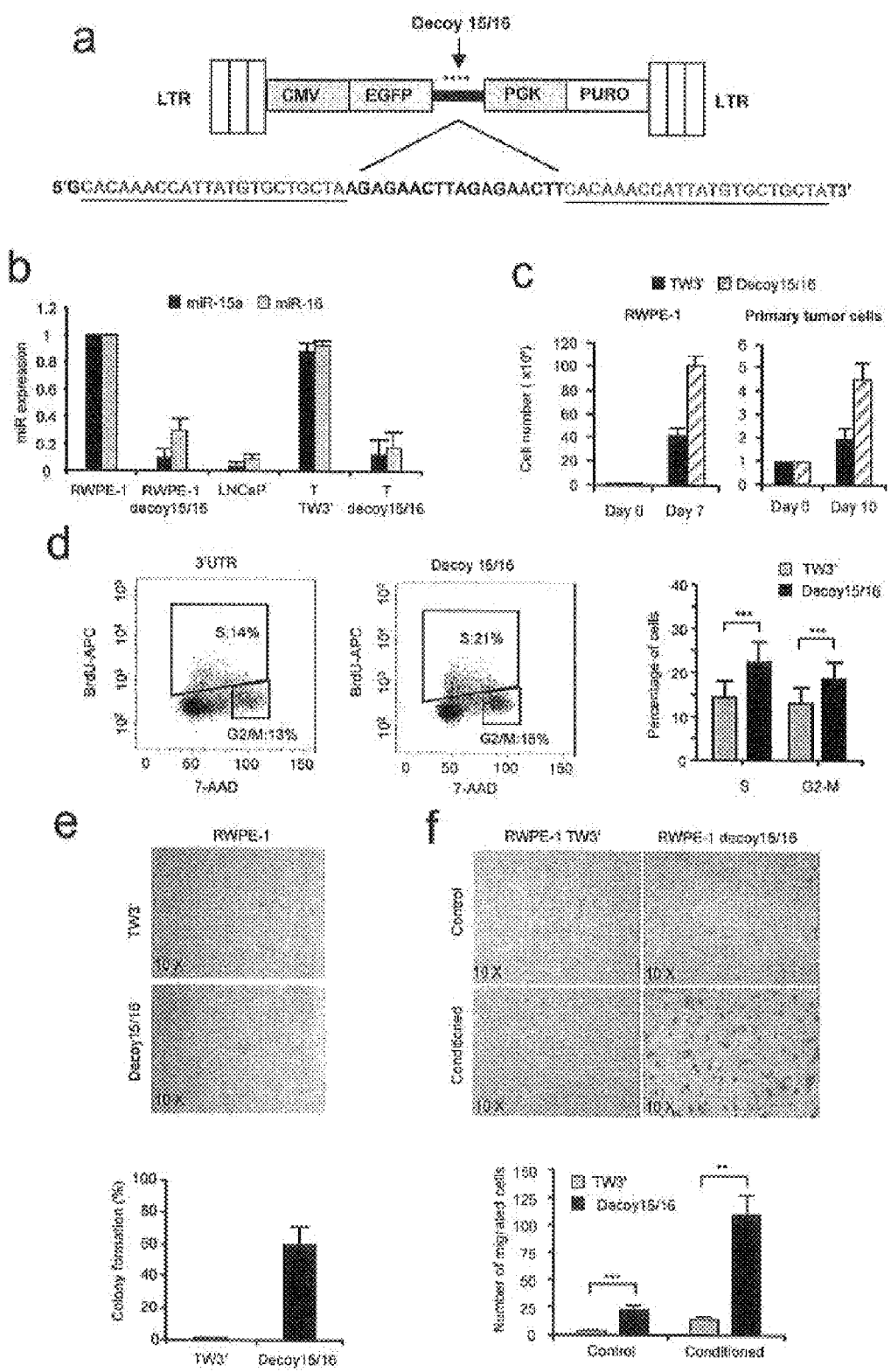

FIG. 2. Targeting of miR-15a and miR-16 promotes prostate cell proliferation and invasiveness.

a) Schematic description of the functional elements in the TW3'UTRdecoy15/16 vector. CMV: cytomegalovirus immediate early promoter; PGK: phosphoglycerate kinase gene promoter, PURO: puromycin resistance gene. b) Real time PCR evaluation of miR-15a and miR-16 levels in RWPE-1decoy15/16, LNCaP and primary tumor with normal miR expression, transduced with control (TW3') or decoy15/16 vectors. The untrasformed prostate cell line RWPE-1 was used as reference. c) Cell growth of RWPE-1 and primary tumor cells with normal miR expression, transduced with decoy15/16 or with the empty vector (TW3'). d) Cell cycle analysis by cytofluorimetric profiling of BrdU/7AAD-stained RWPE-1 cells transduced with TW3' or decoy15/16 vector. Results were analyzed by two-way ANOVA and Bonferroni post-tests. P value for the two groups was <0.001. e) Representative soft-agar colony formation assay for RWPE-1 TW3' and RWPE-1decoy15/16 cells. Data are mean±s.d. of three independent experiments. f) Migration assay for RWPE-1 TW3' and decoy15/16 cells maintained in standard culture medium (Control) or in prostate cancer fibroblast-conditioned medium (Conditioned). Data were analyzed by t-test. () represents a P value<0.01 and (*) represents a P value<0.001. Data are mean±s.d. of four independent experiments.

Figure 3:
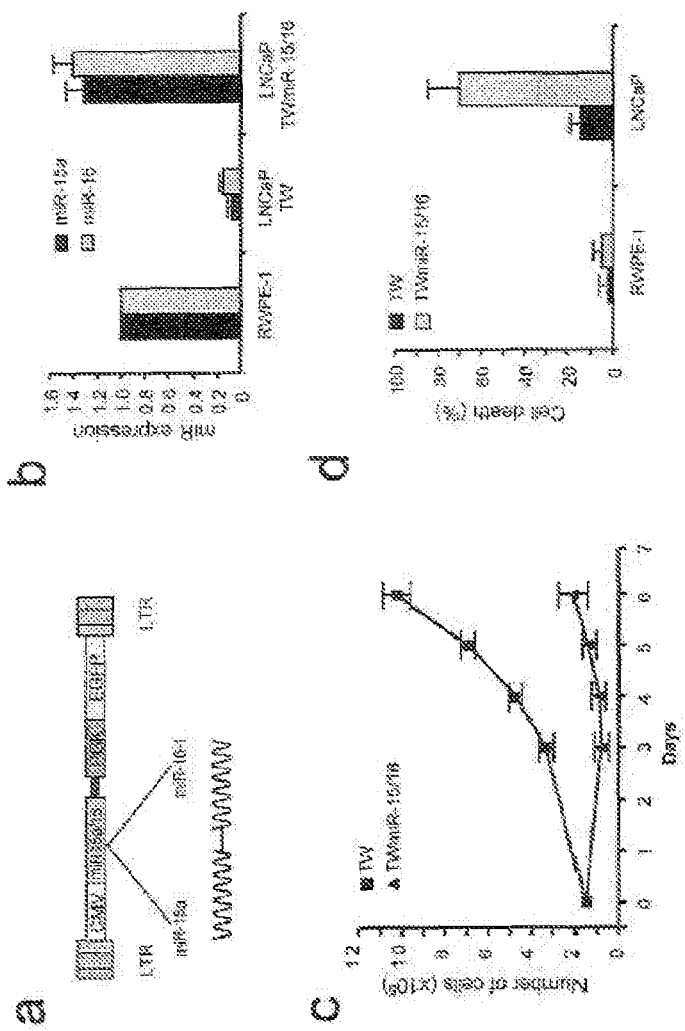
Figure 3:
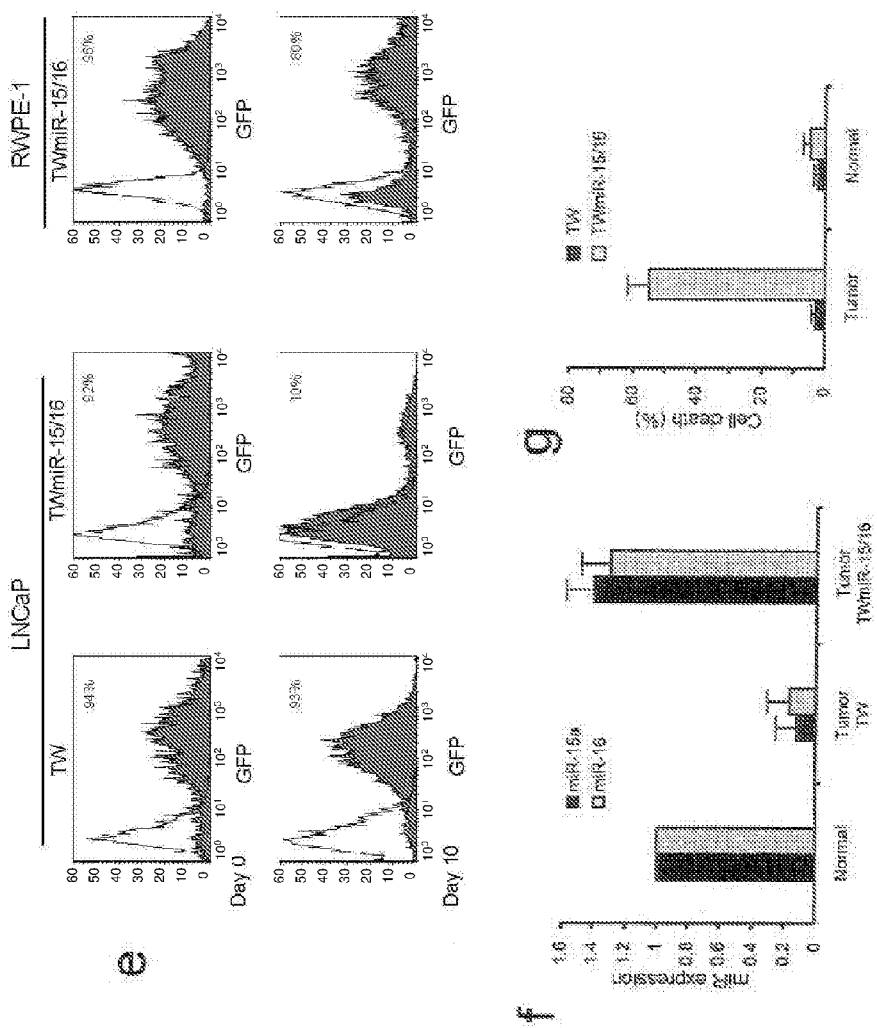

FIG. 3. Restoration of miR-15a and miR-16 induces growth arrest and apoptosis in defective prostate cancer cells.

a) Schematic description of TWmiR-15/miR-16. The miR-15a/miR-16-1 cluster was subcloned in the TWEEN vector under the control of the CMV promoter. b) Real time PCR evaluation of miR-15a and miR-16 expression in LNCaP cells transduced with TWmiR-15a/miR-16 vector. Transduced cells were compared with cells infected with empty vector (TW) and with RWPE-1 cell line. c) Cell growth of LNCaP cells infected with empty vector (TW) or TWmiR-15/miR-16. Data are mean±s.d. of four independent experiments. d) Cell death of normal (RWPE-1) and tumor (LNCaP) cells transduced with TWmiR-15a/miR-16 or control vector (TW) was evaluated 48 hours after lentiviral infection. e) Flow cytometry profiles of LNCaP and RWPE-1 cells infected with TW and TWmiR-15a/miR-16 viruses. GFP expression is shown 24 h (Day 0) and 11 days (Day 10) postinfection. f) Real time PCR analysis of miR-15a/miR-16 expression on miR-defective prostate tumor primary cells after transduction with TWmiR-15a/miR-16 or empty TW vector. Primary normal prostate cells were used as reference. g) Cell death evaluation in tumor and normal prostate primary cells infected as in f. Data are mean±s.d. of three independent experiments.

Figure 4:
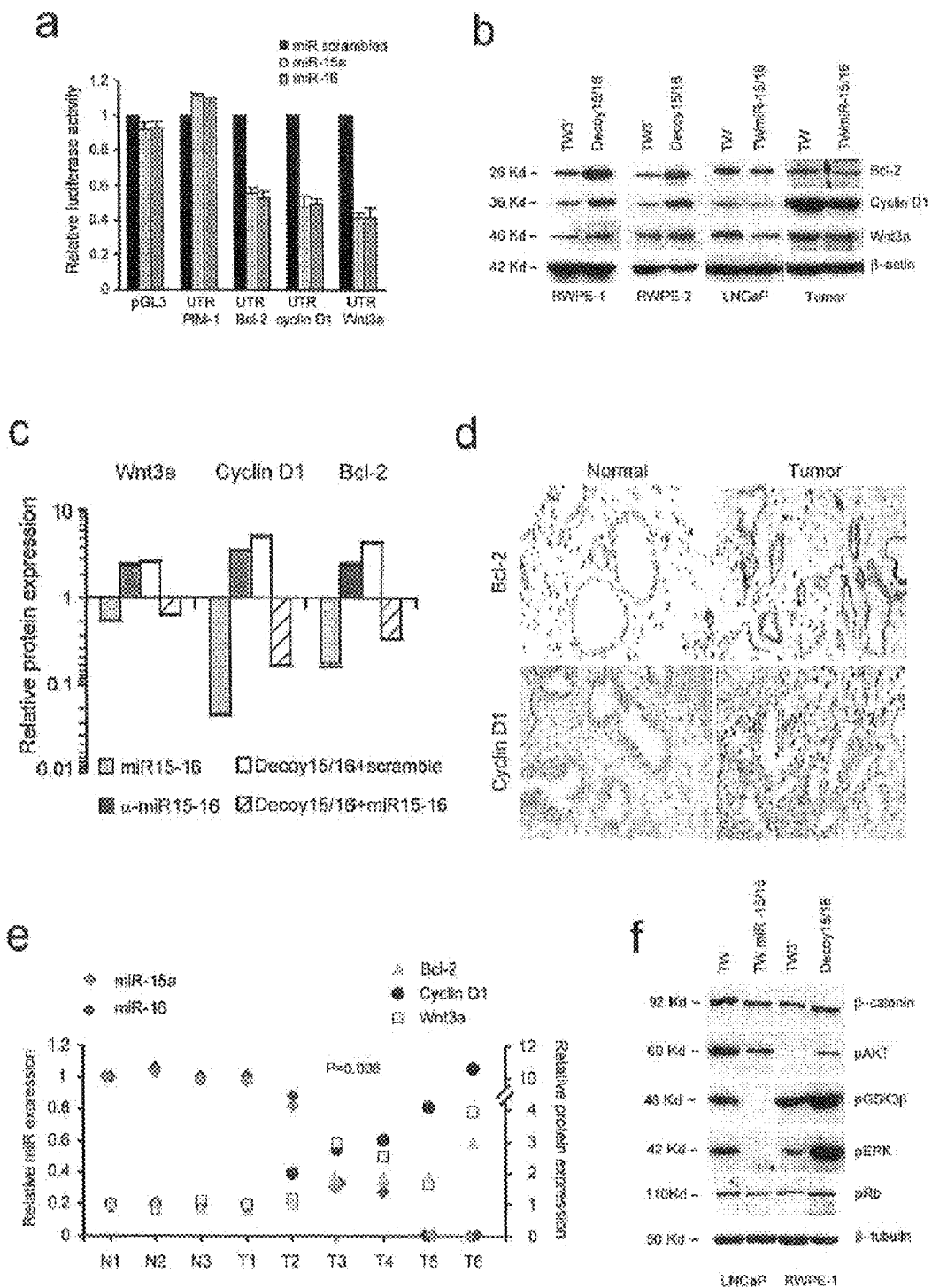

FIG. 4. miR-15a and miR-16 target Cyclin D1 and Wnt3a.

a) pGL3 and pGL3-UTRs vectors were cotransfected with miR-15a, miR-16 or miR scrambled oligos. Luciferase activity was detected 48 hours posttransfection. Data are mean ±s.d. of five independent experiments. b) Western blotting analysis of miR-15a/miR-16 targets in RWPE-1, RWPE-2, LNCaP and miR defective tumoral primary cells (Tumor) transduced with either decoy15/16 or TWmiR-15a/miR-16 and the corresponding control vectors. c) Wild type (grey and blue) and decoy15/16 RWPE-1 (yellow and light blue) cells were transfected with sense oligos specific for both miR-15 and 16 (miR15-16); wild type RWPE-1 cells were also treated with antisense oligos for miR-15 and 16 (α-miR15-16). The reported values were obtained using their respective scramble treated control cells as reference. Data are mean ±s.d. of three independent experiments. d) Bcl-2 and cyclin D1 immunohistochemical staining of normal prostate tissues and miR-15/16 defective tumors. One representative case of three non-tumoral controls and five miR-15/miR-16 defective tumors is shown. e) Inverse correlation between miR-15/16 and target proteins in primary prostate cultures. The miR expression was evaluated by real time PCR, normalizing over a normal sample (N1) used as reference. Protein levels were reported as Western blotting densitometry normalized over β-actin protein expression and then compared to Ni. Nine indicative samples are shown. Spearman correlation analysis was performed between miR and targets levels. A correlation coefficient of −0.81 with a p=0.008 indicates an inverse relationship between miR-15/16 expression and the levels of cyclin D1, Bcl-2 and Wnt3a. f) Western blot analysis of β-catenin, pAKT, pGSK3 β, pERK, pRb in LNCaP and RWPE-1 cells. One representative of three independent experiments is shown.

Figure 5:
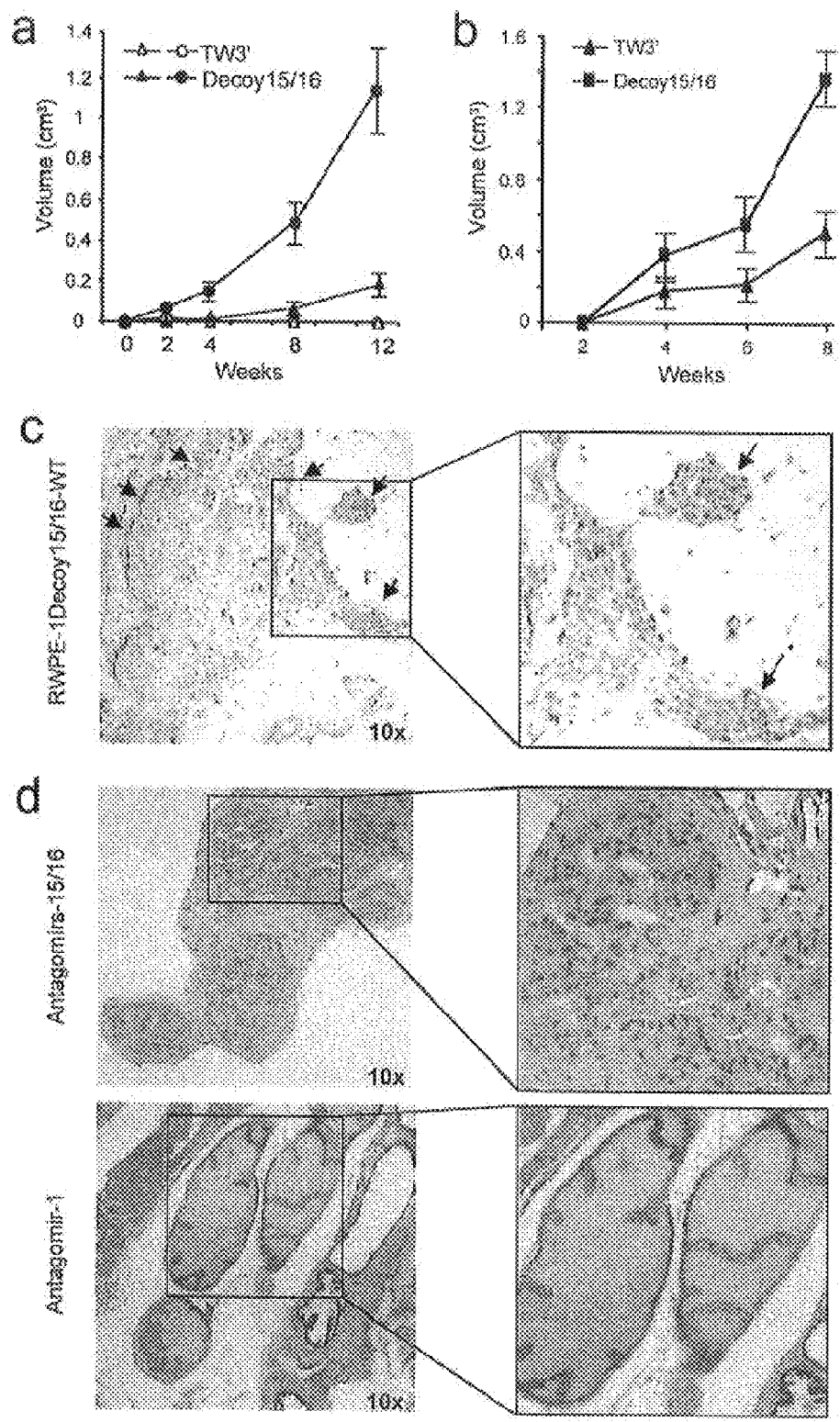

FIG. 5. Effects of miR-15a/miR-16 knockdown on tumor development in vivo.

a) Tumorigenic potential of 4×10$^6$ (triangles) or 10$^7$ (circles) untransformed RWPE-1 cells transduced with decoy15/16 or control TW3' vector. Data are mean±s.d. of five mice analyzed per each group in three independent experiments. b) Tumor size after injection of 4±10$^6$ tumorigenic RWPE-2 cells transduced with TW3' or decoy15/16 vectors. Data are mean±s.d. of five mice analyzed per each group in two independent experiments. c) 2.8×10$^6$ wild type RWPE-1 cells together with 1.2×10$^6$ RWPE-1 decoy15/16 cells were resuspended in matrigel and injected subcutaneously in NOD-SCID mice. After 12 weeks, mice were sacrificed and tumor sections were stained with anti-GFP antibody. Arrows indicate GFP+ cells at the tumor front. Six mice were analyzed in two independent experiments. d) Hematoxylin-eosin staining of mouse prostates treated with antagomir by local injection of either antagomir-15a in combination with antagomir-16 (Antagomir-15/16) or antagomir-1 as a control. Five mice per each group were analyzed in two independent experiments.

Figure 6:
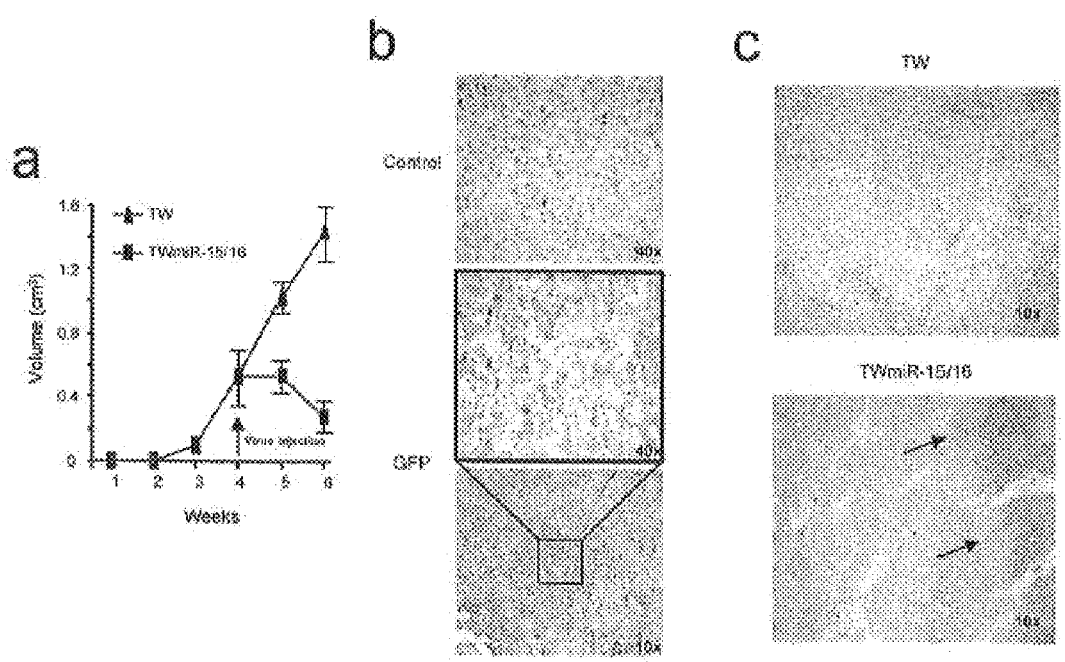

FIG. 6. Therapeutic effect of viral miR-15a/miR-16 delivery on subcutaneous NOD-SCID mouse xenografts.

a) Effect on tumor growth of miR-15a/miR-16 reconstitution. Tumors generated four weeks after injection of 8×10$^6$ LNCaP cells were treated with virus particles containing TW and TWmiR-15a/miR-16 vectors. Data are mean±s.d. of three independent experiments with three mice per each group. b) Immunohistochemical analysis of LNCaP xenografts following injection of TW viral particles as in a). Sections were stained with control or anti-GFP antibodies two weeks after virus treatment. A larger area at low magnification is shown at the bottom. c) Hematoxylin-eosin staining (magnification 10×) of six weeks LNCaP xenografts, two weeks after injection of TW and TWmiR-15a/miR-16 viral particles. Rare living tumor cell islands in a necrotic tumor treated with TWmiR-15/16 vector are indicated by arrows.

Figure 7A:
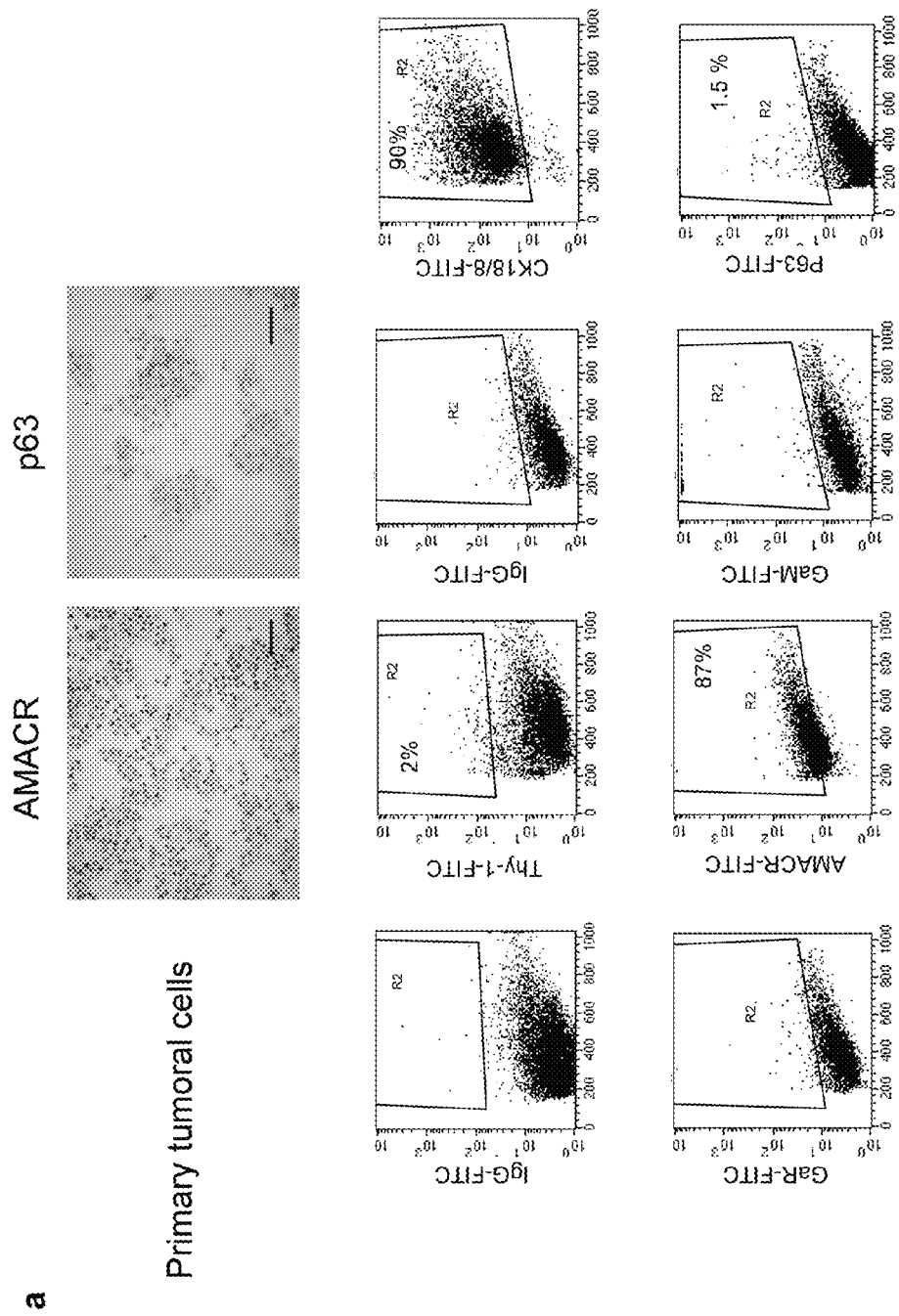
Figure 7B:
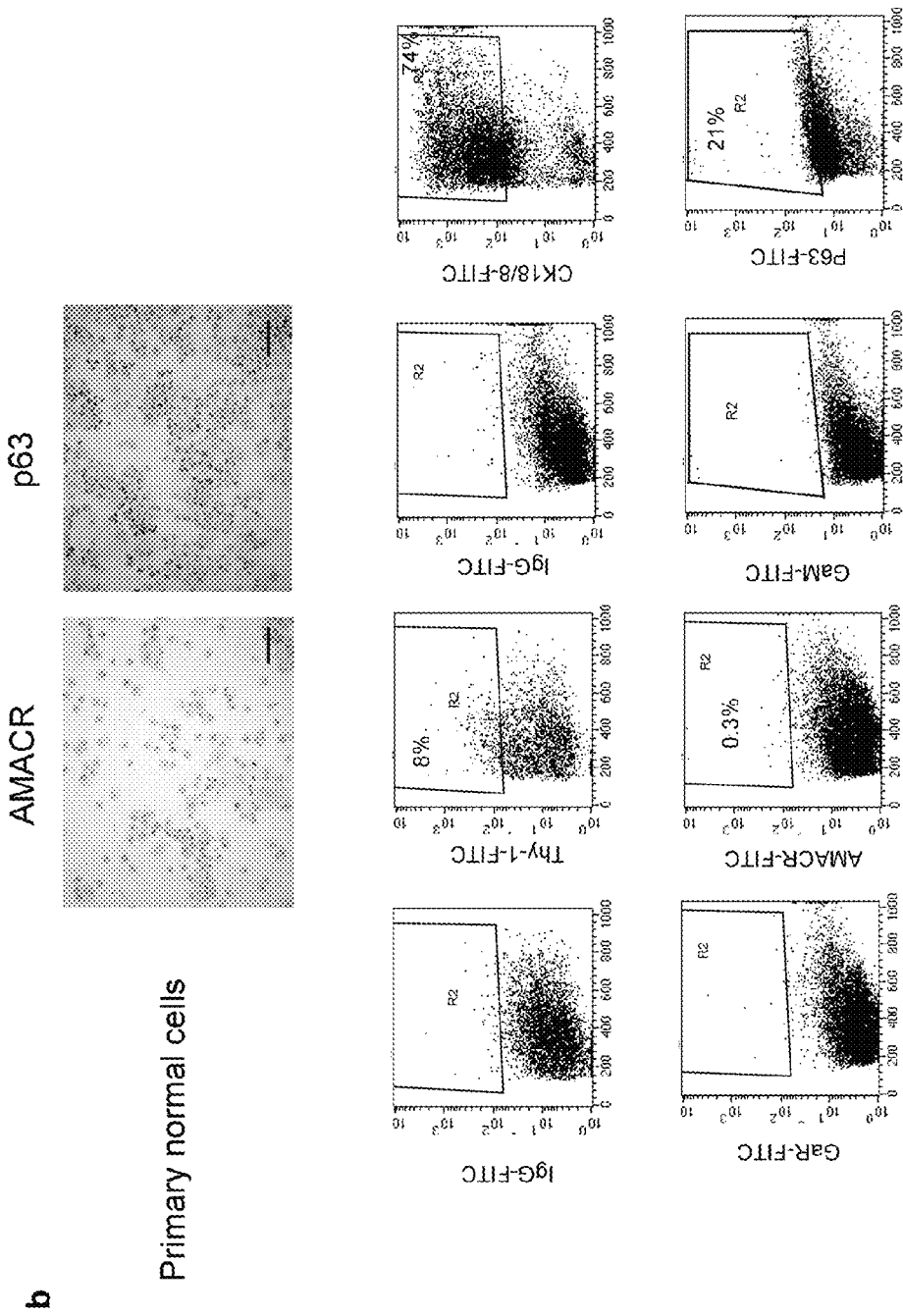

FIG. 7. Characterization of Primary prostate cells

Expression of Thy-1, Cytokeratin 18/8, AMACR and p63 in tumoral (a) and normal (b) prostate primary cells from freshly-isolated surgical prostate specimens as determined by immunocytochemistry on cytospin centrifuged cells and flow cytometry.

Figure 8:
Figure 8:
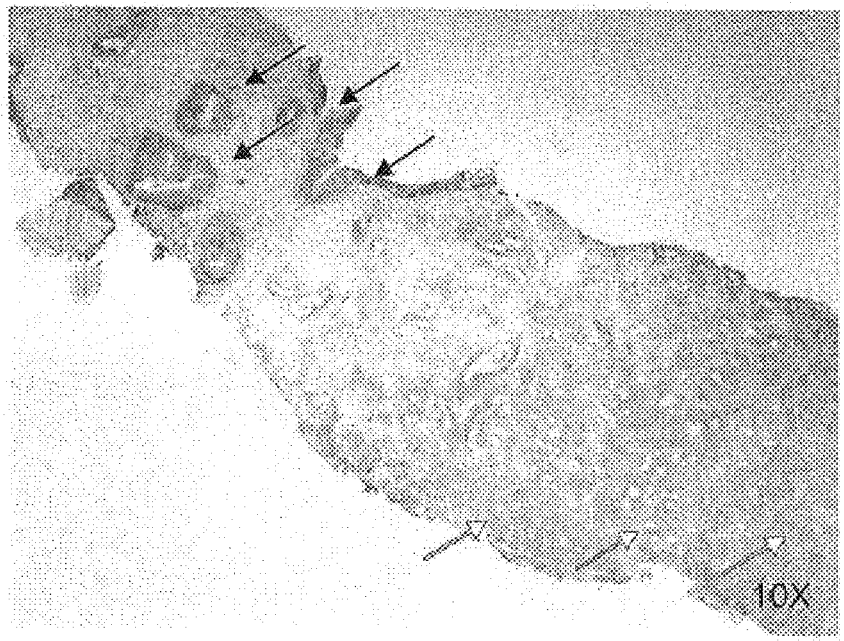

FIG. 8. In situ hybridization for miR-15a and miR-16 miR-15a and miR-16 expression by in situ hybridization in tissue sections, 10× magnification. Both images contain tumoral (red arrows) and non-tumoral (black arrows) tissue.

Figure 9:
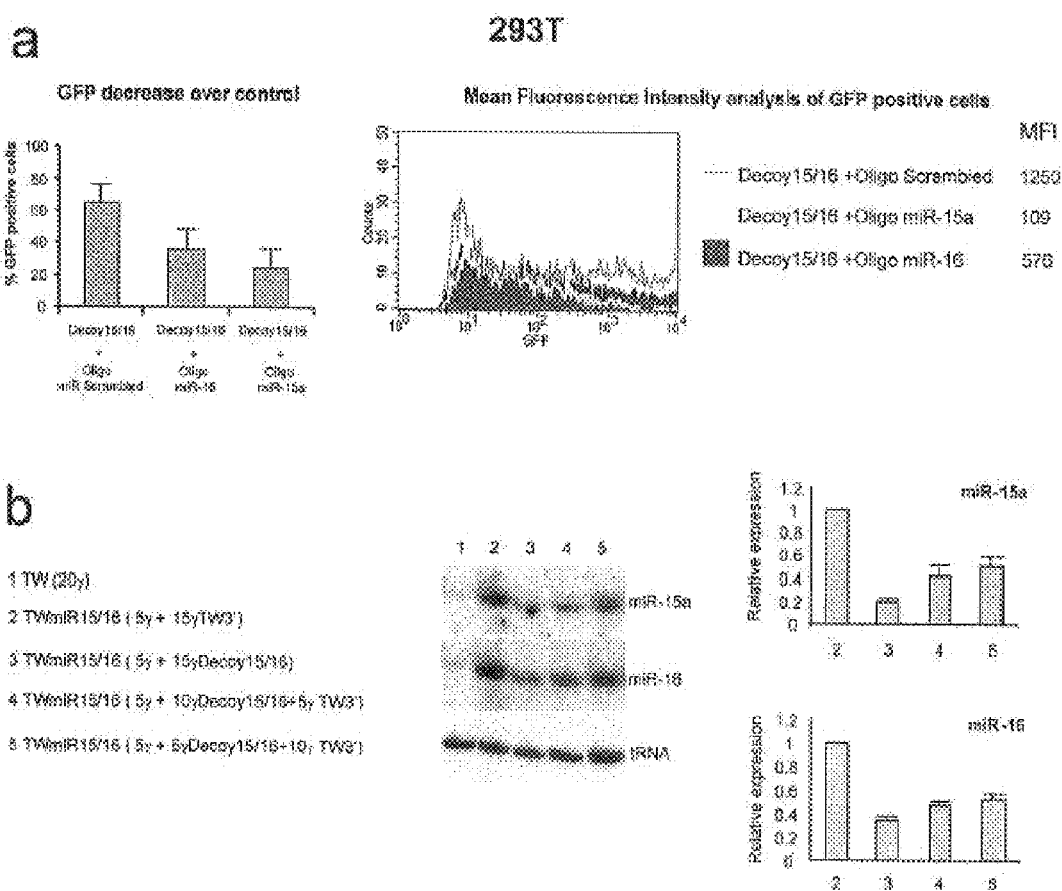

FIG. 9. Validation of decoy15/16 vector a) Percentage of GFP positivity and relative mean fluorescence of 293T cells transfected with decoy15/16 vector in the presence of scrambled, miR-16 or miR-15a oligos. b) Northern blotting analysis of 293T cells cotrasfected with increased ratios of decoy15/16 vector versus expression vector TWmiR-15a/miR-16. The total amount of plasmid DNA was maintained at 20γ using empty vector TW3'. Band relative quantification for miR-15a and miR-16 northern blotting is reported.

Figure 10:
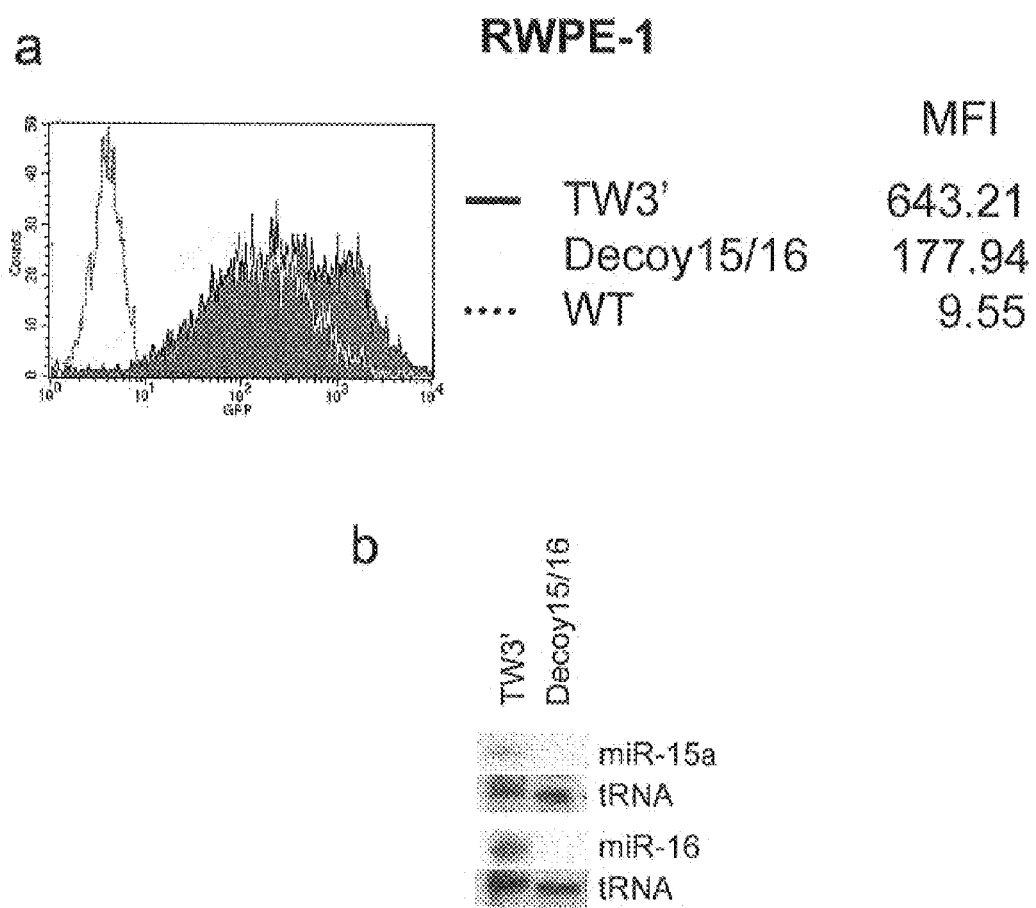

FIG. 10. Decoy15/16 infected RWPE-1 cells showed a significant decrease of both miR-15a and miR-16 a) Flow cytometry analysis of GFP expression in RWPE-1 cells infected with TW3' and decoy15/16 vectors. Mean fluorescence intensity of GFP expression was evaluated comparing RWPE-1 wild type cells to TW3' and decoy15/16 cells. b) RWPE-1 cells infected with TW3' and decoy15/16 vectors were analyzed for endogenous miR expression by Northern blotting.

Figure 11:
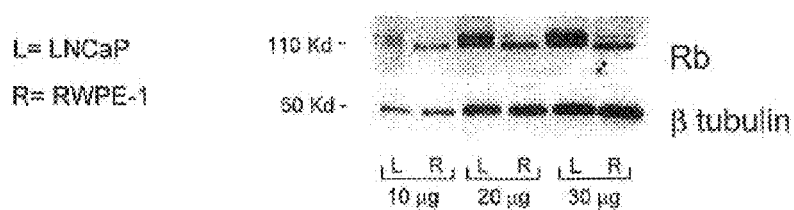
Figure 11:
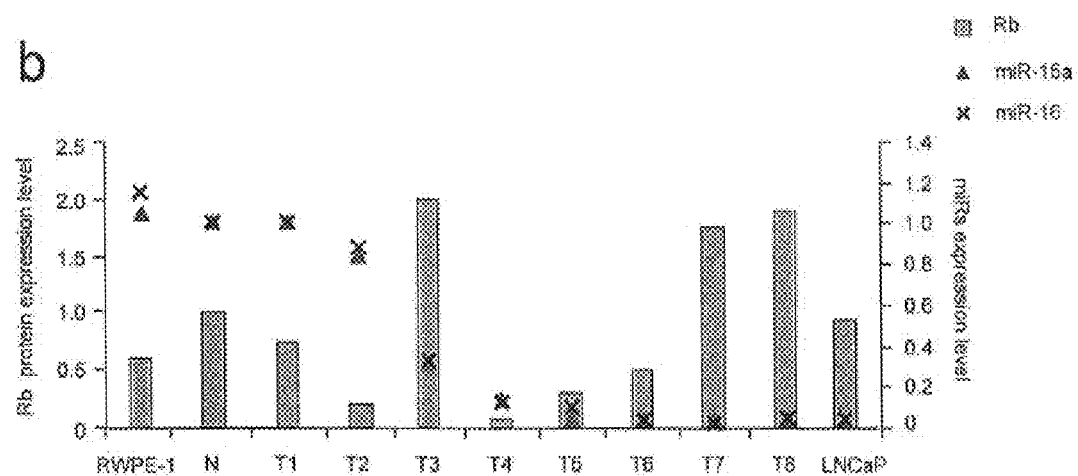

FIG. 11. No correlation between Rb expression and loss of miR-15/16 in prostate cancer cells a) Western blotting analysis of Rb expression in miR-15/miR-16 defective LNCaP and in RWPE-1 cells. b) Rb expression profile in primary prostate tumor cells (T1-T8) as compared to miR-15/miR-16 level, non-tumoral primary cells (N) were used as control reference.

Figure 12:
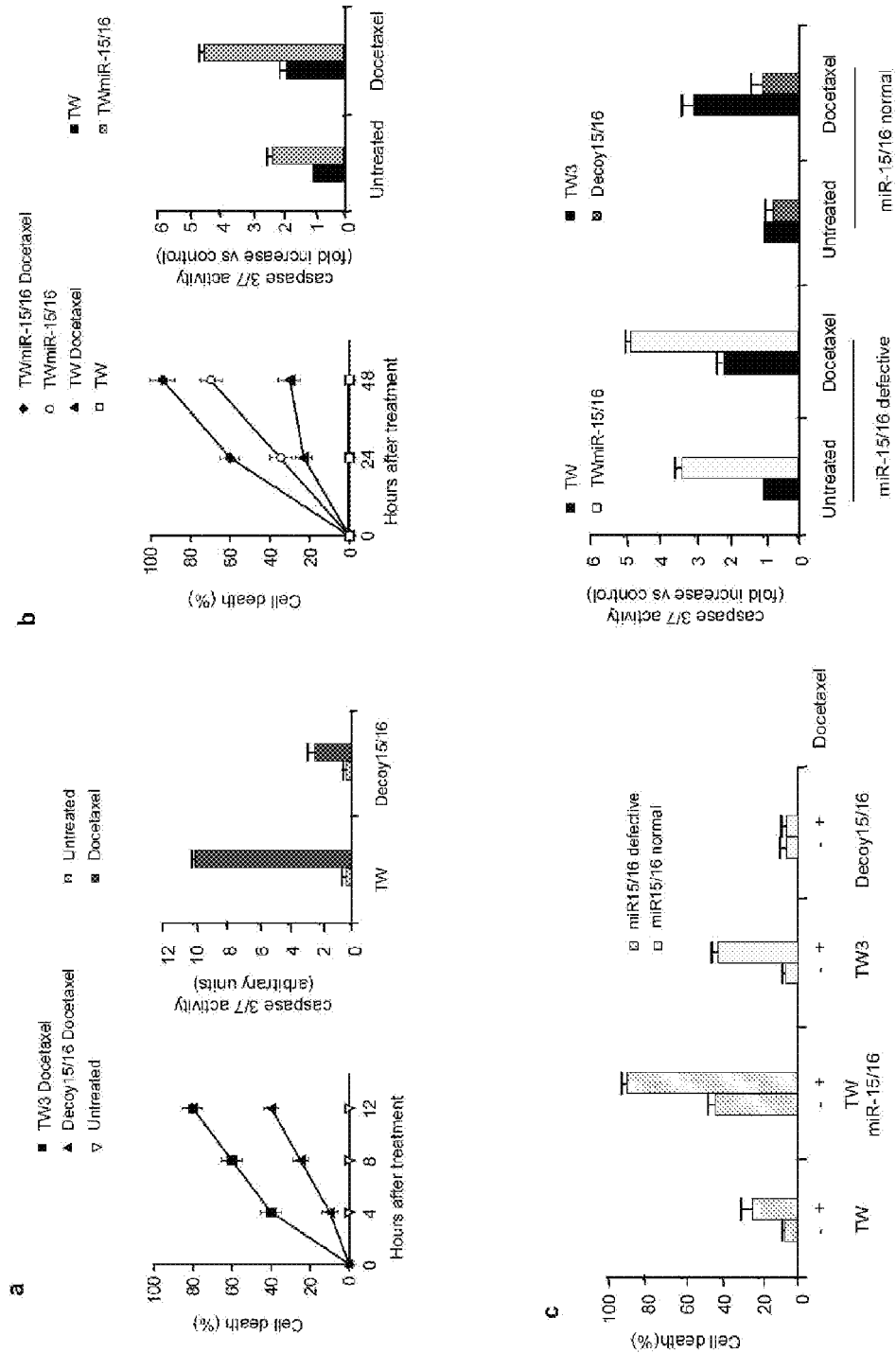

FIG. 12. Effect of miR-15a/miR-16 modulation on the cytotoxic activity of docetaxel a) Evaluation of cell death and caspase activation in RWPE-1 cells infected with TW3' or decoy15/16 vectors and treated with 10 ng/ml of docetaxel. Caspase activation was measured after 4 h of treatment. b) Evaluation of cell death and caspase activation in LNCaP cells infected with TW or TWmiR-15a/miR-16 vectors and exposed to 10 ng/ml of docetaxel. c) Evaluation of cell death and caspase activation in miR15a/miR-16 defective or non-defective (normal) primary tumor cells transduced as indicated and treated with 10 ng/ml docetaxel. Cell death was measured after 24 h exposure to docetaxel. Caspase activation in LNCaP and primary tumor cells was measured after 18 h of treatment. Data are mean±s.d. of at least three independent experiments for each group.

Figure 13:
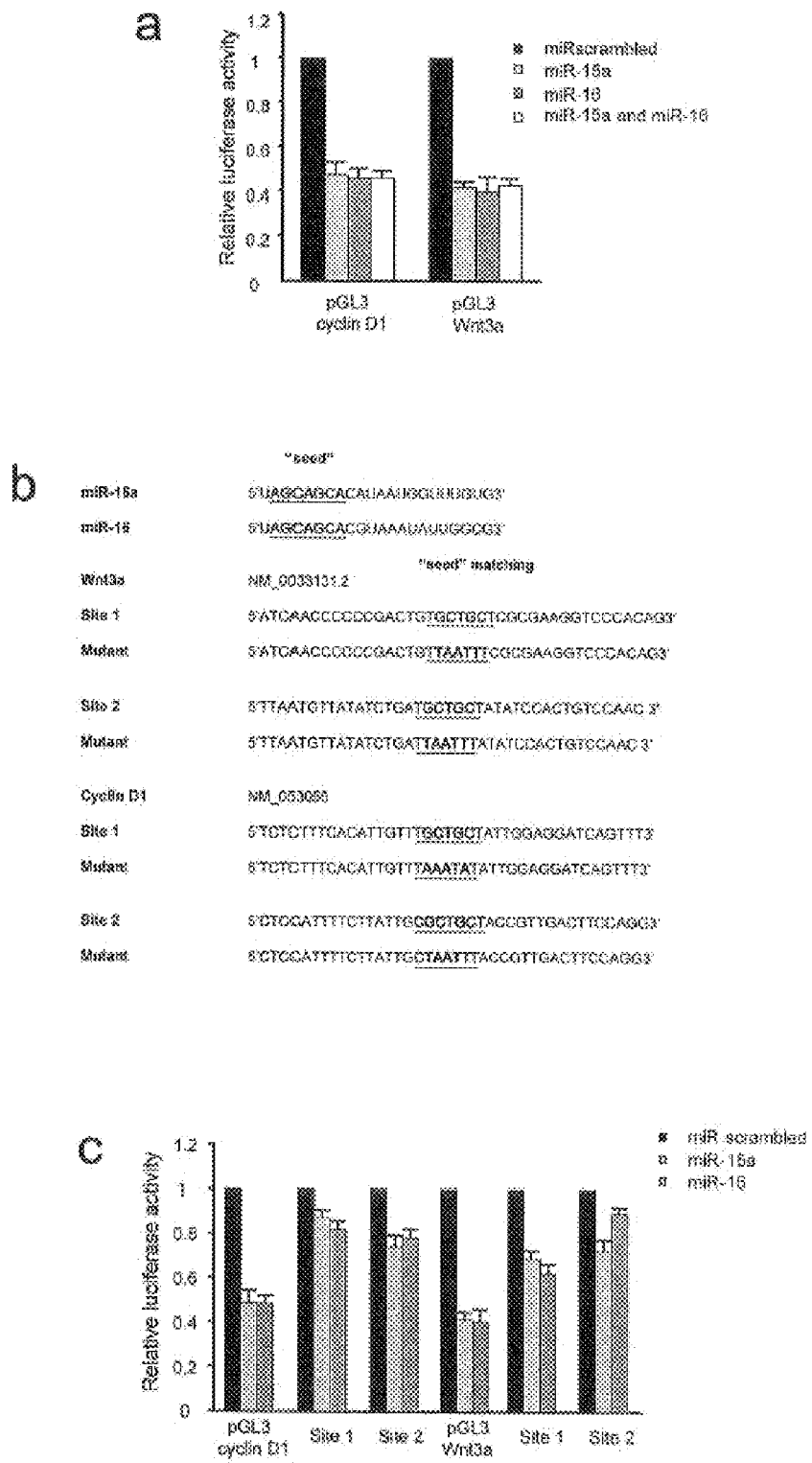

FIG. 13. Binding site evaluation for miR-15a and miR-16 a) pGL3 and pGL3-3'UTRs vectors were cotransfected with miR scrambled, miR-15a, miR-16 or with a mixture of miR-15a and miR-16 oligos. Luciferase activity was detected at day 2 posttransfection. b) Sequences and introduced mutations of the miR-15a and miR-16 binding sites. Sequences of mir-15 and mir-16 are given in SEQ ID NOs:4 and 5, respectively, and the remaining sequences are given in SEQ ID NOs:26-33, sequentially. c) Luciferase assay was performed using pGL3-UTRs bearing mutations in the putative miR target sites.

Figure 14:
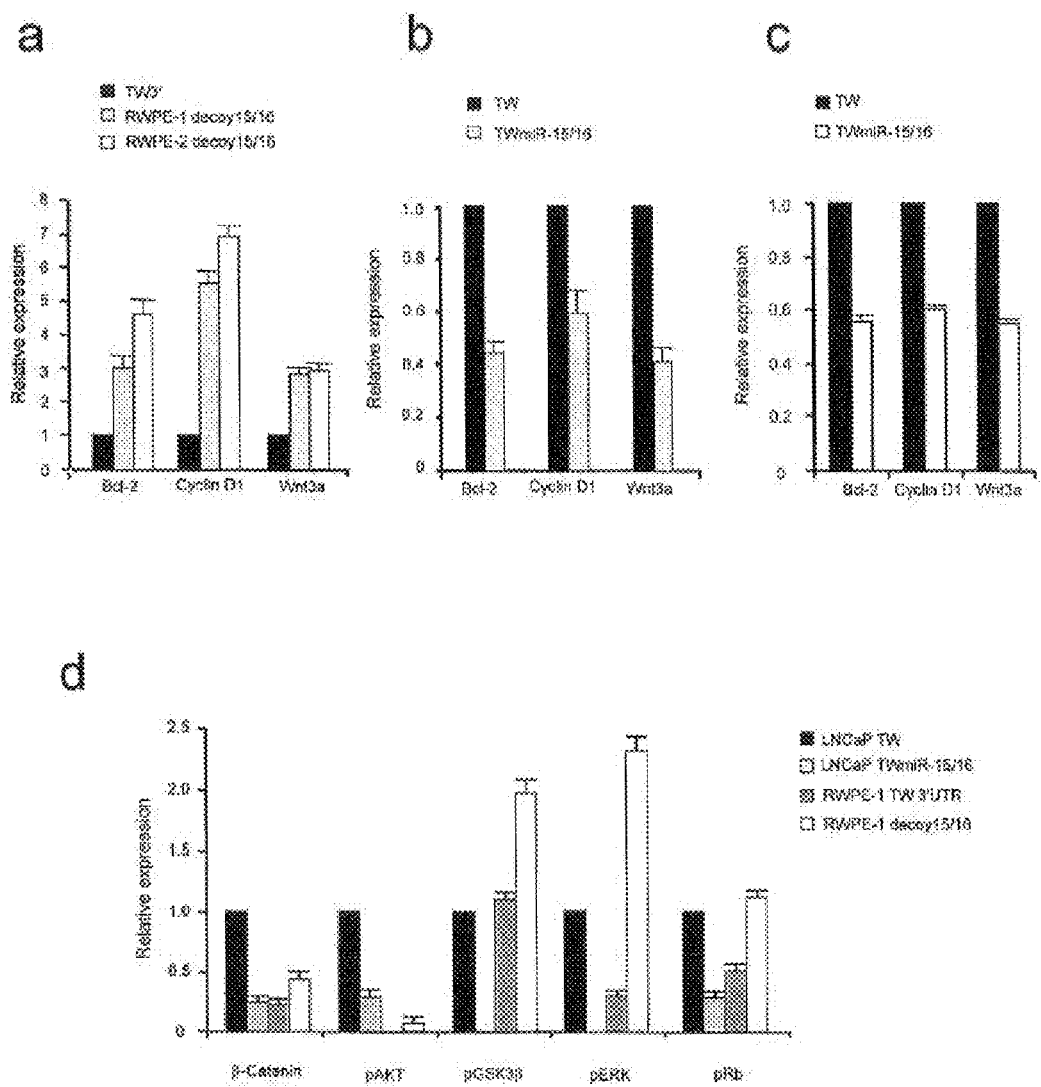

FIG. 14. Relative protein quantification of Western blotting analysis a-c) Relative protein quantification of miR-15a/miR-16 targets in RWPE-1 and RWPE-2 cells (a), LNCaP cells (b) or miR defective primary tumoral cells transduced as indicated (c). d) Relative protein quantification of β-catenin, pAKT, pGSK3 β, pERK, pRb. Values are obtained by normalizing each sample with the corresponding expression of β-tubulin as compared with the level measured in LNCaP cells. Data are mean±s.d. of three independent experiments.

Figure 15:
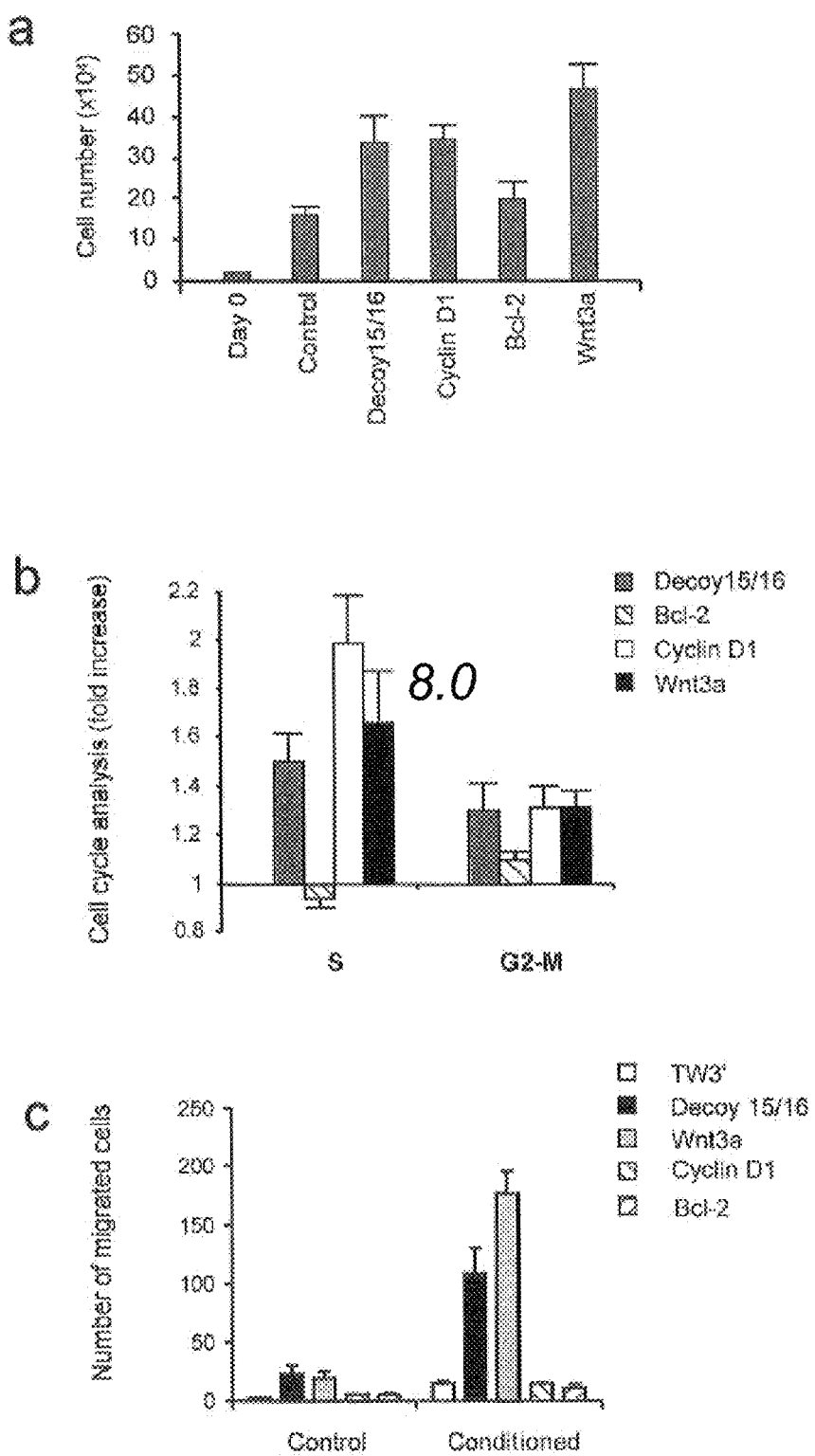

FIG. 15. Cyclin D1, Wnt3a and Bcl-2 gene transfer into RWPE-1 cells a) Cell growth of RWPE-1 cells transduced with cyclin D1, Wnt3a and Bcl-2 genes. Control value was obtained by the combined mean number of TW3' and TW transduced cells. Histogram bars represent the cell number obtained after 4 days of culture. All samples were 20,000 cells at day 0. b) Cell cycle analysis as measured by cytofluorimetric profiling of BrdU/7AAD-stained RWPE-1 cells transduced with decoy15/16, cyclin D1, Wnt3a or Bcl-2. Values were reported as fold increase over empty vector transduced cells (TW3'and TW vectors). Data are mean±s.d. of three independent experiments. c) Migration assay for RWPE-1 TW3', decoy15/16, cyclin D1, Wnt3a and Bcl-2 cells maintained in standard culture medium (Control) or in prostate cancer fibroblast-conditioned medium (Conditioned). Data are mean±s.d. of four independent experiments.

Figure 16:
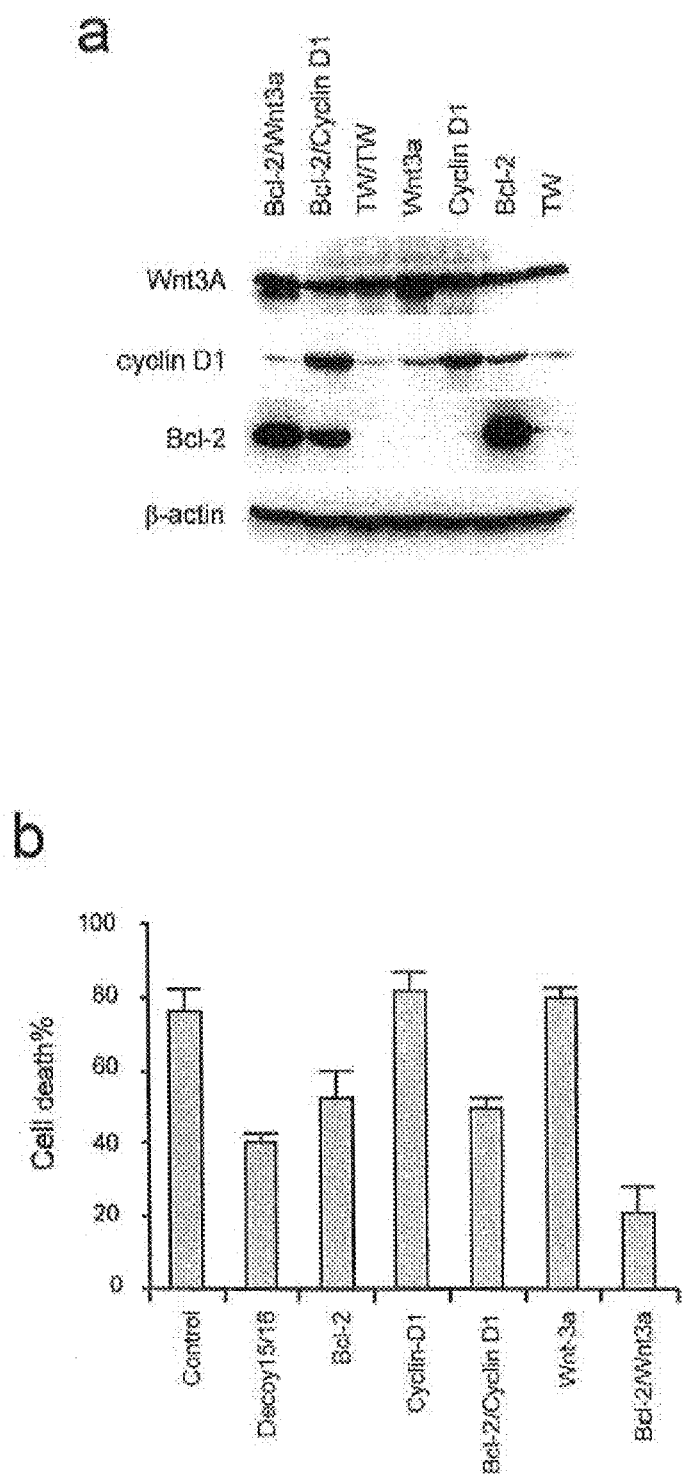

FIG. 16. Effect of Bcl-2, Cyclin D1, Wnt3a gene modulation on the cytotoxic activity of docetaxel a) Western blotting analysis of RWPE-1 transduced with Bcl-2, cyclin D1, Wnt3a and empty vector (TW), alone or in double combination. b) Evaluation of cell death in RWPE-1 cells transduced as indicated and treated for 12 h with 10 ng/ml docetaxel. Control is the mean death value of TW3', TW and TW/TW transduced cells. Data are mean±s.d. of three independent experiments.

Figure 17:
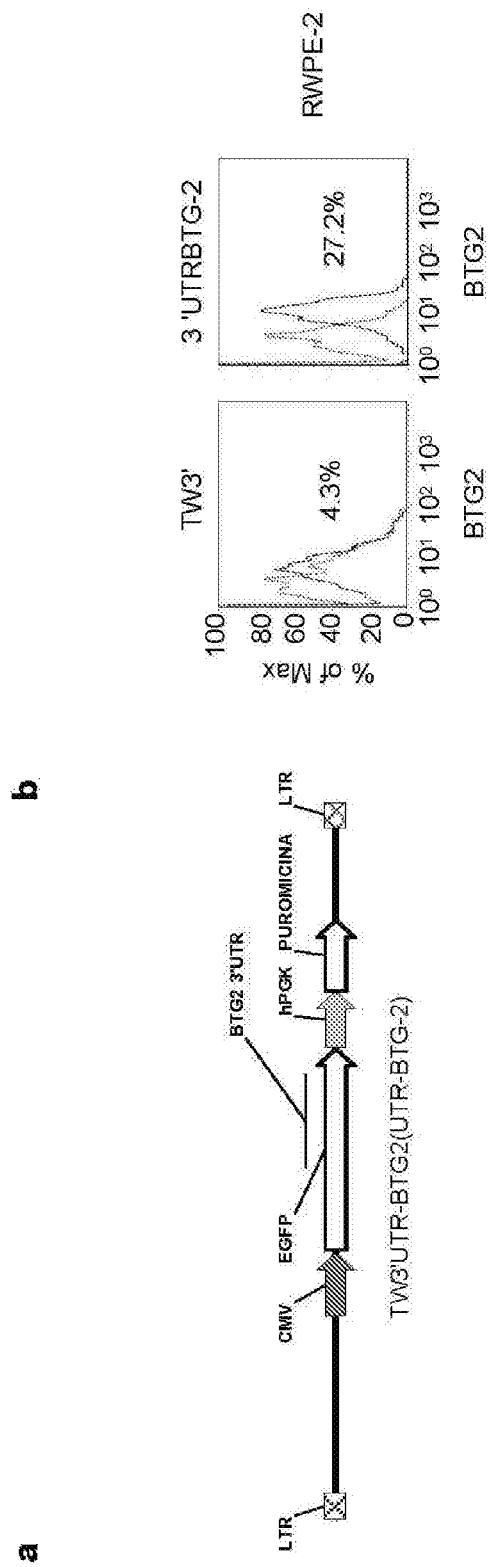
Figure 17:
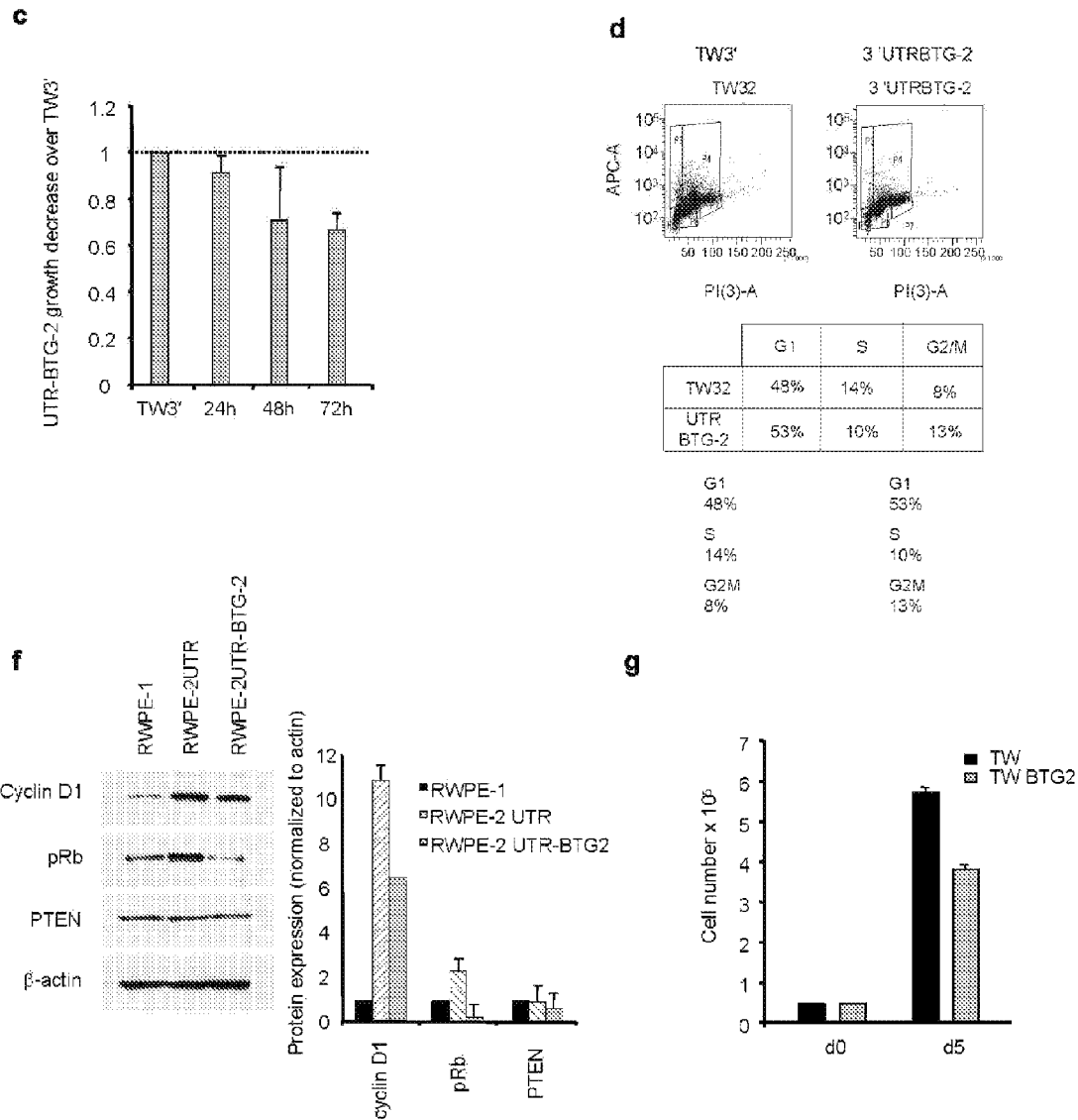

FIG. 17: BTG-2 derepression impairs tumor cell growth.

a) Schematic description of the functional elements in the TW3'UTR BTG-2 vector. CMV: cytomegalovirus immediate early promoter; PGK: phosphoglycerate kinase gene promoter, PURO: puromycin resistance gene.b) Flow cytometry profiles of RWPE-2 cells infected with TW3' and TW3'UTR BTG-2 viruses. BTG-2 expression is shown 48 h postinfection. c) RWPE-2 cells transduced with TW3'UTR BTG-2 impairs cell growth over TW3' infected population. After day 3 the TW3'UTR BTG-2 transduced cells undergo a massive conuterselection.d) Cell cycle analysis by cytofluorimetric profiling of BrdU/7AAD-stained RWPE-2 cells transduced with TW3' or TW3'UTR BTG-2 vector. One representative experiment was reported. f) Western blot analysis of Cyclin D1, pRb, PTEN, p63 and sprouty in RWPE-2 cells. RWPE-1 cells were used as normal control cell line. One representative of three independent experiments is shown. g) Cell growth of PC-3 cells transduced with BTG-2 gene. Histogram bars represent the cell number obtained after 5 days of culture. After day 5 the BTG-2 transduced cells undergo a massive counterselection.

Figure 18:
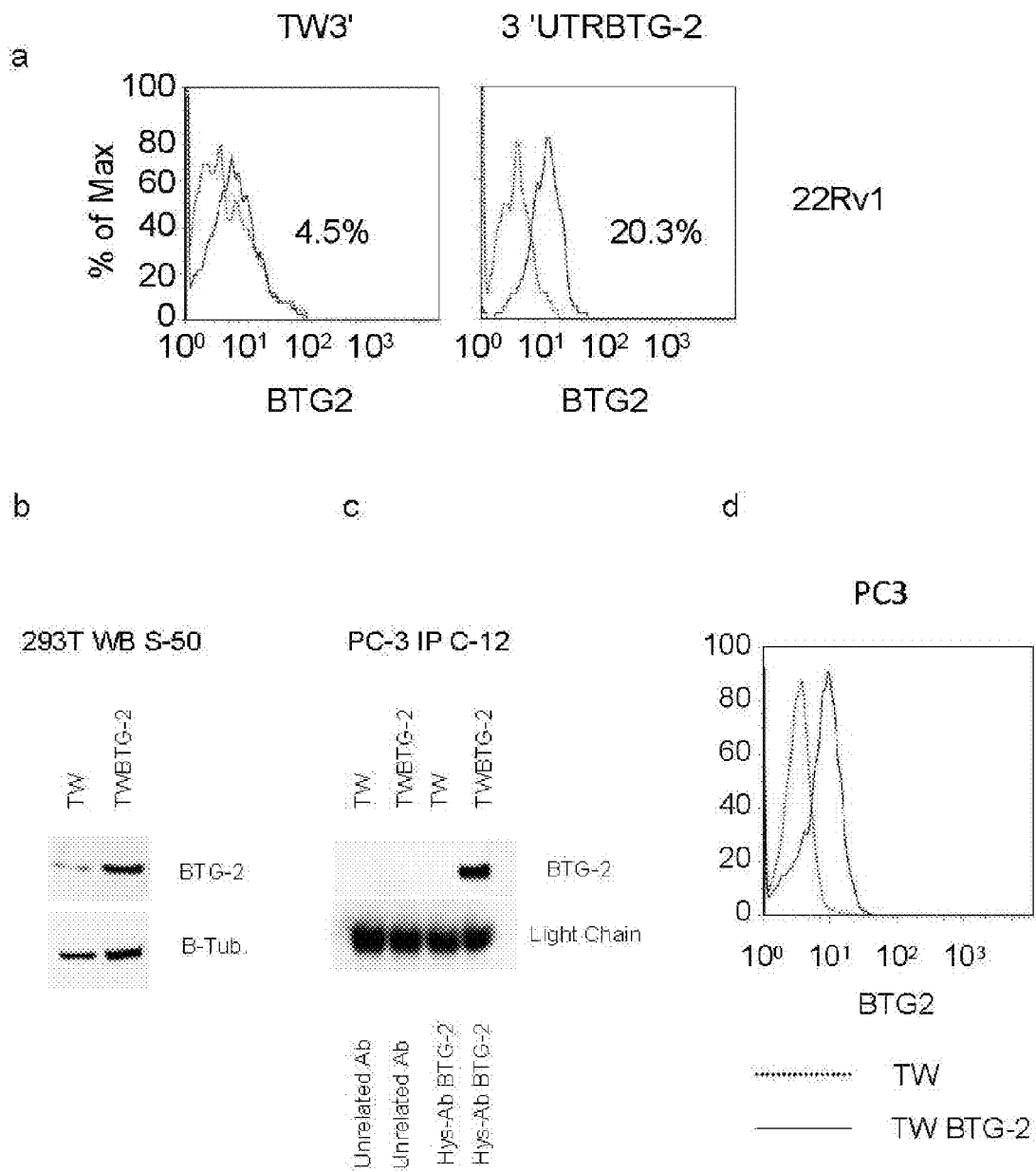

FIG. 18: Control experiments.

a) BTG-2 flow cytometry profile of 22Rv1 cells transduced with TW3'UTR BTG-2. C-12 antibody was used. b) Western blotting on 293T cell transduced with BTG-2 gene. S-20 antibody was used. c) Immunoprecipitazion of BTG-2 protein in PC-3 TW-BTG-2 transduced cells. BTG-2 protein was immunoprecipitated with C-12 antibody and detected for western blotting with antibody used in Passeri D. Mol Cell Biol. 2006 July.d) Flow cytometry analysis (FACS) of PC-3 transduced with TW and TWBTG-2 vectors.

Figure 19:
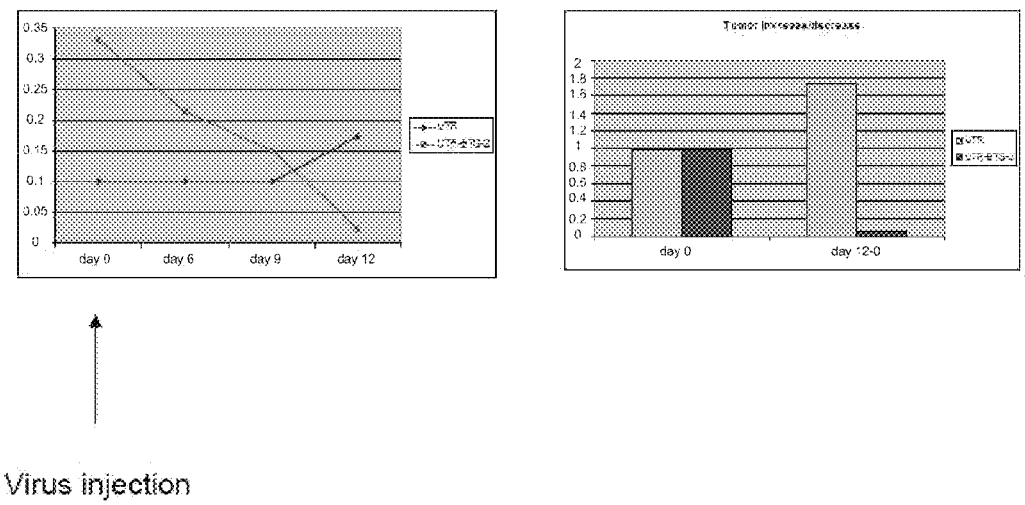
Figure 19:
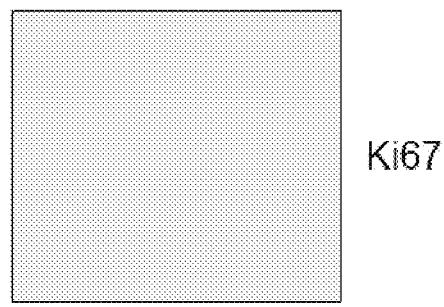
Figure 19:
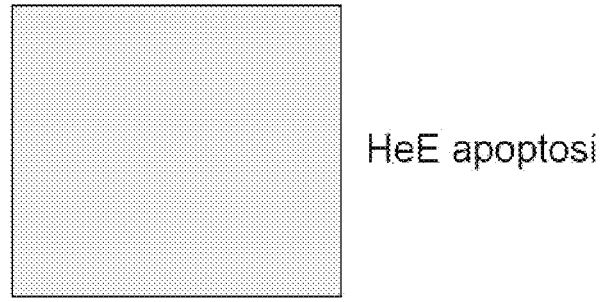

FIG. 19: In vivo BTG-2 derepression impairs tumor mass proliferation.

Effect on tumor growth of miR-21 sequestration. Tumors generated four weeks after injection of 8×106 RWPE-2 cells were treated with virus particles containing TW3' and TW3'UTR BTG-2. vectors. Data are mean±s.d. of three independent experiments with three mice per each group.

EXAMPLE 1

Methods

Cells. LNCaP, RWPE-1 and RWPE-2 cell lines were obtained from ATCC and cultivated in the recommended medium. Tissue dissociation and isolation of primary prostate cells were performed as described [41] with some modifications (see Supplementary Methods). Tumoral and non-tumoral prostate surgical specimens were cultured in collagen-coated plate with BRFF-HPC1 medium (AthenaES, Baltimore Md.). The purity of human prostate primary cell preparation was confirmed by immunocytochemistry and FACS analysis through the expression of the stromal marker Thy-1 and cytokeratins (>85%). Tissues were obtained from radical prostatectomy at the Department of Urology, S. Giovanni Bosco Hospital of Turin, Italy. All samples were collected with informed consent of the patients.

Immunohistochemistry and in situ Hybridization.

Immunohistochemistry experiments were performed on 2 μm thick formalin-fixed paraffin-embedded tissue sections. After dewaxing, sections were permeabilized for 30 min with TBS containing 0.4% Triton X-100 and blocked for 30 min with TBS containing 5% BSA. Then, sections were incubated overnight at 4° C. with the primary antibodies. Mouse anti-Bcl-2 (1:100) was from BioGenex (San Ramon, Calif.); mouse anti-cyclin D1 (1:20) from Dako Corp. (Carpintera, Calif.); rabbit anti-EGFP (1:200) from Invitrogen (Carlsbad, Calif.). After washing with TBS, sections were incubated for 1 hr at RT with the biotinylated anti-mouse or anti-rabbit secondary antibody (1:500, Jackson Lab, Maine) and treated with streptavidin conjugated with HRP (DAKO Corp., Carpintera, Calif.). Finally, the signal was detected using diaminobenzidine (DAB) as chromogen. Sections were counterstained with hematoxylin, dehydrated and mounted with xylene.

LNA-modified probes biotinylated at 5'-end (Exiqon), were used to detect the in situ hybridization signal for miR-15a and miR-16 on formalin-fixed paraffin-embedded prostate tissue. In situ hybridization was performed as described by Nelson and colleagues[42] with some modifications (see Supplementary Methods).

Western and Northern blotting.

Protein extracts were prepared by resuspending cell pellets in 1% NP40 lysis buffer (20 mM Tris/HCl pH 7.2, 200 mM NaCl, 1% NP40) with Protease and Phosphatase Inhibitor Cocktails I and II (Sigma-Aldrich). Equal amounts of proteins were used for SDS-PAGE. Samples were analyzed by standard immunoblot procedure with anti-Bcl-2, anti-β-catenin, anti-pAKT (Ser-473), anti-pGSK3β (Ser9), anti-pRb (Ser807-811) (Cell Signalling Technology, Danvers, Mass.), anti-cyclin D1, anti-Wnt3a, anti-pERK, and anti-Rb (Santa Cruz) antibodies. Anti-β-actin (Oncogene Research Products, San Diego, Calif.) or anti-β-tubulin (Sigma) monoclonal antibodies were used as loading control. Northern blotting was performed with antisense probe for mature miRs as reported [20].

Soft-Agar Colony and Motility Assay.

For the soft-agar assay, TW3' and decoy15/16 RWPE-1 cells were resuspended in culture medium supplemented with 0.4% agar and plated at a density of 100, 250, 500 cells/well in duplicate in a 24-well plate, previously coated with a 3-mm layer of the same modified medium. Cells were cultured for two weeks and then photographed. Three separated experiments were performed for each cellular density. Chemotaxis was tested in modified Boyden chambers containing porous (8-μm), uncoated polycarbonate membranes (Corning Incorporated, Nagon Park Acton, Mass.), as described in Supplementary Methods.

Generation of Lentiviral Vectors and Gene Transfer.

For TWmiR-15a/miR-16 generation, miR-15a/miR-16-1 precursor DNA was PCR-amplified from human genomic DNA. The amplified fragment spanning 724 bp (NCBI36: ch13:49519256:49523338) was subcloned into the lentiviral vector TWEEN [20] under the CMV promoter. miR transgene expression was assayed by real time PCR using the appropriate oligonucleotides from Applied Biosystems.

The TW3'UTR vector was obtained by modifying the EGFP 3'UTR of the TWEEN vector through the insertion of a multicloning site (XhoI-XbaI) that allowed the subcloning of antisense miR sequences. Then the EGFP modified 3'UTR cassette was inserted under the CMV promoter control. Moreover, a puromycin resistance gene was inserted under the PGK promoter control to allow the selection of transduced cells.

For decoy-15/16 vector generation, tandem sequences complementary to miR-15a separated by a 18 bp unrelated spacer were synthesized as oligonucleotides (Invitrogen) and then inserted into XhoI-XbaI multicloning site in TW3'UTR vector. Given the high homology between miR-15a and miR-16 especially in their "seed" sequence (residues 2-8), "decoy" sequences can match to miR-16 (FIGS. 9 and 10). This design, using multiple copies of complementary targets, was intended to optimize repression of the transgene in the presence of the miRNAs [5]. The sequestering capacity of the decoy vector was further validated by Northern blotting analysis of miR-15a and miR-16 in 293T cells co-transfected with TWmiRNA15/16 and decreasing concentrations of Decoy15/16 vector (1:3, 1:2, 1:1). To maintain an equal total amount (20 μg) of plasmid transfection in all conditions, we added variable doses of TW3' vector to replace or complement the Decoy15/16. The TW vector (20 μg) and a combination of TWmiR15/16 (5 μg) and TW3' (15 μg) vectors were used as negative and positive controls, respectively (FIG. 9b).

Recombinant lentiviral particles were obtained as described [43]. Cells were infected with $1\times10^6$ TU particles of viruses, as previously indicated [43]. For in vivo experiments, the viral supernatant was concentrated 250-fold. To obtain high-titre vector stocks, virus was ultracentrifuged [43] and injected in 200 μl of PBS directly into tumor xenografts of NOD-SCID mice. Bcl-2, cyclin D1 and Wnt3a genes were subcloned into the TWEEN vector. Double exogenous expression of Bcl2/cyclin D1 and Bcl-2/Wnt3a was obtained by infecting with Bcl-2 virus particles the RWPE-1 cells stably transduced with either cyclin D1 or Wnt3a. Selection of double infected cells was obtained by flow cytometry sorting with FACSaria (Becton Dickinson), setting the sorting gate on cells brighter then those with single infection. The same procedure was followed for obtaining empty vector control cells.

Reporter Assays.

3'UTR segments of Bcl-2, cyclin D1 and Wnt3a were amplified by PCR from normal human genomic DNA and subcloned into the 3'UTR of the firefly luciferase coding sequence into pGL3-Promoter (Promega), see Supplementary Methods. Then K562 ($5\times10^4$ cells per well) were transfected using Lipofectamine 2000 (Invitrogen) following the manufacturer's instructions. The transfection mix included: (a) 0.8 μg of pGL3-3'UTR plasmid and 50 ng of the control vector pRL-TK (Promega); (b) 25 μmol of either non-targeting RNA control (scrambled) or miR-15a or miR-16 oligonucleotides (Ambion). Forty-eight hours post-transfection, firefly and renilla luciferase activities were measured using the Dual Luciferase Assay kit (Promega). Transfection efficiencies were normalized by calculating the ratio of firefly to renilla. For each construct the relative luciferase activities were calculated by dividing the values obtained in the transfection of miR-15a and miR-16 by those of miR scrambled. Each experiment was performed in duplicate and replicated five times.

Target Screening.

In this study, we used three publicly available search engines for target prediction: TargetScan (Release 2.1), http://genes.mit.edu/targetscan [4, 44, 45]; miRanda, http://www-.microrna.org [46]; and PicTar, http://pictar.bio.nyu.edu [47]. The putative targets common to the different algorithms were obtained by sequentially inputting TargetScan hits to PicTar and finally to miRanda. The p-value for any target in this list was computed by TargetScan and a threshold value of <0.1 was then set for positive selection. This procedure yielded a list of 61 top-scoring candidates of which only a few could directly promote cell proliferation.

RNA Extraction and Quantitative Real Time PCR.

Total RNA was extracted with acid phenol methods. Fifty nanograms of RNA were reverse transcribed with M-MLV reverse transcriptase (Invitrogen) and cDNA was diluted 1:10 in the PCR reactions. Housekeeping gene reverse transcription was performed using random primers, while miR specific looped-primers were used for miR-15a and miR-16 reactions. TaqMan microRNA assays (Applied Biosystems) for miR-15a and miR-16 were used for PCR amplification. Normalization was performed using snRNA U6 and rRNA S18 as references (RNU6B TaqMan microRNA assay and S18 TaqMan assay on demand, Applied Biosystems). Since we obtained comparable results with both housekeeping genes, we performed all experiments using S18 as a reference. Calibration was performed using cDNA samples from normal prostate primary cells or the RWPE-1 cell line. Values are expressed in terms of $2^{-\Delta\Delta C_T}$ where $\Delta\Delta C_T = \Delta C_{Tsample} - \Delta C_{Tcalibrator}$; $\Delta C_T$ was the difference in threshold cycles between the miR and S18 amplicons, and $C_T$ was a parameter given by ABI PRISM 7700 Sequence Detector software by negative correlation with an internal reference dye (ROX).

Cytofluorimetric and Viability Assays.

For cell cycle determination, $2.5 \times 10^5$ RWPE-1TW3' and RWPE-1decoy15/16 cells were analyzed with the BD Pharmingen BrdU Flow Kit staining protocol. Cells were seeded in 6 wells plate for 24 h. Then BrdU was added in culture medium and maintained for 1 h at 37° C. in incubator. Fixation and permeabilization of the cells was performed with BD Cytofix/Cytoperm Buffer following the protocol indication. Cells were stained with anti-BrdU-APC for 20 minutes at room temperature and treated with 7-AAD before FACS analysis. BrdU-unlabelled cells from the same population were used as negative control. Cells were analyzed with LSR II (BD). Cell death was evaluated by trypan blue staining, PI staining and flow cytometry analysis, Apo-percentage assay (Biocolor) and Cell Titer kit (Promega). Caspase activation was detected using APO-one Homogeneous Caspase3/7 Assay Kit (Promega).

Statistical Analysis.

Data are presented as the mean±s.d. Results of BrdU assays were analyzed by two-way ANOVA and Bonferroni post-tests. Migration assay was analyzed with Student's t-test. Spearman correlation analysis was performed between miR and corresponding targets levels.

Supplementary Methods

Primary Cells Isolation and Characterization

Benign and neoplastic tissue specimens were taken from the prostate base in the transition zone and the suspicious areas in the peripheral zone, respectively. The tumoral and non-tumoral nature of each sample was confirmed by histo-pathological examination. Freshly-isolated surgical tumor specimens were collected and treated with collagenase for enzymatic dissociation. The homogenate suspension was maintained in culture in collagen-coated plate with a specific medium that allowed the propagation of primary prostate cells (BRFF-HPC1 medium, AthenaES, Baltimore, Md.). In this condition, cells grew in monolayer assuming a round-shape aspect visible under the microscope.

To determine the number of luminal cells and those contaminating fibroblasts, cells were stained for cytokeratin 18 (Clone5D3 by NovoCastra, used 1:10) and Thy-1 (Clone 5E10 by Becton Dickinson, used 1:50), respectively. The percentage of tumor cells was evaluated with anti-AMACR (1:50, Sanova Pharma, Vienna, Austria), while normal basal cells were detected with anti-p63 (1:50, BioGenex). For flow cytometry, Thy-1 staining was performed in PBS at 4° C. for 1 h, while the other antibodies were used after fixation and permeabilization with parafolmaldehyde 2% and Triton 0.1%. For immunocytochemistry on cytospin preparation, cells were fixed for 10 min with 4% paraformaldehyde, abundantly rinsed in PBS and permeabilized for 5 min with 0.2% Triton X-100. Nonspecific binding was blocked by treatment with 1% BSA for 1 hour and, finally, cells were incubated at RT for 1 hour with primary antibodies. After washing, cells were incubated for 1 hr with the biotinylated secondary antibodies (1:500, Jackson Lab) and treated with streptavidin-HRP (DAKO Corp.). The signal was detected using diaminobenzidine (DAB) as chromogen.

Cells were counterstained with hematoxylin, dehydrated and mounted with xylene. Only cultures with >85% enrichment of prostatic epithelial cells were used for further experiments. To reduce the fibroblast contamination, we treated the cell culture plate with a diluted (1 g/L) trypsin solution for 1-2 minutes once or twice. Prostate epithelial cells are more resistant to this treatment because they rapidly grow in round compact areas, while contaminating fibroblasts are still isolated and detach more easily from the culture dish.

Conditioned Medium and Motility Assay.

Two $\times 10^4$ RWPE-1 TW3' and decoy15/16 cells were suspended in 200 µl of PRF-SFM (Phenol Red Free-Serum Free Medium, Invitrogen) and plated into upper wells. Lower wells contained 500 µl of cell culture medium (Supplemented Keratinocyte medium) or PRF-SFM-Conditioned Medium (PRF-SFM-CM), prepared by growing human prostate cancer fibroblasts in PRF-SFM for 48 h; conditioned medium was collected, filtered and kept in −20° C. until use.

To study chemotaxis, Supplemented Keratinocyte medium and PRF-SFM-CM were added to lower wells only. After 72 h, the cells in the upper wells were removed, whereas the cells that migrated to the lower wells were fixed and stained in Coomassie Blue solution (0.25 g of Coomassie blue: 45 ml water: 45 ml methanol:10 ml glacial acetic acid) for 5 min. Chambers were washed with water. The levels of invasion were assessed by counting the number of cells present in 10 fields on the lower surface of the membrane, under light microscope (20×).

Reporter Assays and Constructs

The miR-15a/miR-16 target genes UTRs were cloned in the Xba I site of pGL3 promoter, immediately downstream from the stop codon of the luciferase coding sequence. For Bcl-2, a 3'UTR of 1329 bp fragment was amplified, corresponding to residues 2446-3774 of Genbank Acc No M14745. For cyclin D1 3'UTR, a 1036 bp fragment was amplified (residues 3011-4078 of No NM_053056). For Wnt3a 3'UTR, a 906 bp fragment was amplified (residues 2026-2932 of No NM_033131.2). For 3'UTR cyclin D1 and Wnt3a mutagenesis, a five nucleotide mutation was inserted in the "seed" sequences interacting with miR-15a and miR-16 (see FIG. 13). Modified and HPLC purified oligonucleotides (Invitrogen) were used for amplification and mutagenesis, performed with Pfu enzyme following the in vitro mutagenesis kit protocol (Invitrogen). Transfection efficiencies of luciferase assays were normalized by calculating the ratio firefly/renilla. For each construct the relative luciferase activities were obtained by dividing the values obtained in the transfection of miR-15a and miR-16 by those of the non targeting miR scrambled. Each experiment was performed in duplicate and replicated five times.

In situ Hybridization

Two µm-thin sections were cut at the microtome, mounted onto poli-lysine-coated glass slides and processed for the hybridization. Briefly, slides were deparaffinized in xylene and hydrated by consecutive dipping in serial dilution of ethanol (100%, 75%, 50%, 25%). Sections were then treated for 5 min with 0.2N HCl, washed in phosphate-buffered saline (PBS, pH 7.4), digested with 40 µg/ml of proteinase K for 25 min at 37° C., and post-fixed for 10 minutes with 10% formaldehyde in PBS. Following fixation, sections were acetylated for 10 min in acetic anhydride/triethanolamine (0.25% v/v acetic anhydride/0.1 M triethanolamine, pH8). Slides were then prehybridized in an oven at 50° C. for 2 hrs in hybridization buffer (65% formamide, 0.075 M sodium citrate (5×SSC), 0.1% Tween-20, adjusted to pH 6.0 with 9.2 mM citric acid, 50 µg/ml heparin, 100 µg/ml yeast tRNA).

Thereafter, slides were hybridized in incubation chambers overnight at 50° C. using 1 µl from a 25 µM stock of probe in 1000 µl of prewarmed hybridization buffer. The day after, sections were washed twice in 5×SSC, followed by 3 washes of 20 min at 50° C. in 50% formamide/2×SSC. Slides were then rinsed 5 times in TBS/0.1% Tween-20 (TBST), and blocked for 1 hr in 4% BSA/TBST. A monoclonal anti-biotin antibody (Vector, U.K.) was applied on sections for 16 hrs at 4° C. After washing, sections were incubated for 1 hr with an alkaline phosphatase-conjugated anti-mouse IgG (Jackson Laboratories, Maine, USA). After secondary incubation, sections were washed twice 10 min each in staining buffer (100 mM Tris, 50 mM $MgCl_2$, 100 mM NaCl, pH 9.5), followed by NBT/BCIP developing solution (Dako Cytomation, CA, USA) for 30 min at RT. After color development, slides were rinsed in TBS, $ddH_2O$ and were dehydrated by passing through a series of alcohols (50%, 75%, 95%, 100%) and xylene and coverslipped in PermaMount.

In vivo Assay

Six-eight weeks old male NOD-SCID mice (Charles River Laboratory, Wilmington, Mass.) were used for examining the tumorigenicity of RWPE-1 decoy15/16 and RWPE-2 decoy15/16 cells, and for evaluation of cytotoxic activity of miR-15/miR-16 in LNCaP xenografts. A total of 200 µl of cell suspension in Matrigel (1:1, vol/vol) was subcutaneously injected into the dorsal surface of mice. The number of cells injected was $4×10^6$ or $10^7$ for RWPE-1, $4×10^6$ for RWPE-2, and $8×10^6$ for LNCaP cells. Tumor incidence three weeks after subcutaneous injection in NOD-SCID mice of $8×10^6$ LNCaP cells in Matrigel was ~90%.

Six week old male BALB/c mice received a single dose of mixed antagomirs selective for miR-15 and 16 by intraprostatic injection through a transverse incision in the lower abdomen. Saline buffer and the unrelated cardio-specific antagomir targeting miR-1 were used as controls. Abdominal wall muscles were incised, and the bladder and seminal vesicles were delivered through the incision to expose the prostate. Antagomirs were injected via a 0.3 mm needle directly into the anterior prostate. The incision was closed using a running suture of 4-0 silk. Antagomirs were administered at the final dose of 80 mg/Kg of body weight in 0.2 ml per injection. Mice were not treated with testosterone during the experiments and were sacrificed after 5 weeks post injection.

Results miR-15a/miR-16 Expression in Prostate Tissues

We first examined whether the low expression of the miR-15a/miR-16-1 cluster observed in chronic lymphocytic leukemia was a feature shared by prostate cancer. Therefore, we analyzed miR-15a and miR-16 expression in 20 patients with stage II-III prostate cancer. Freshly isolated surgical tumor specimens were collected and cultivated in a medium that allowed the propagation of prostate primary cells (see Supplementary Methods and FIG. 7). Non-tumoral samples from the same patients were used as a control reference.

Figure 1:
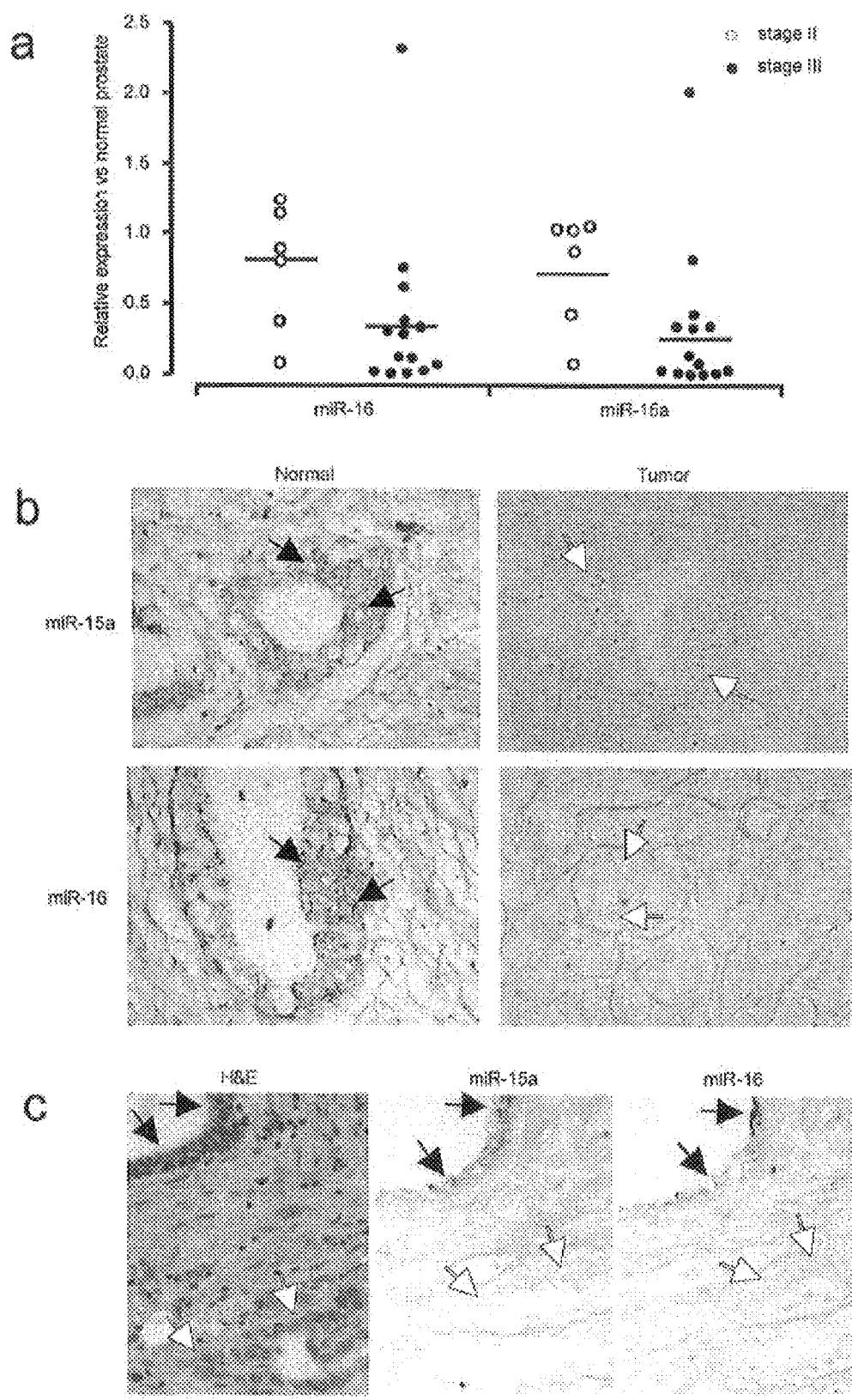
FIG. 1. miR-15a and miR-16 are frequently downregulated in prostate tumors.

Real-time PCR showed a consistent downregulation of both miR-15a and miR-16 in about 80% of the tumor samples analyzed with respect to their normal counterparts, particularly in more advanced tumors (FIG. 1a and Table 1). To confirm that such a low expression in primary cultures mirrored the miR levels of prostate tumors, tissue sections prepared from 15 additional cases were examined by in situ hybridization with miR-15a and miR-16 probes. In 12 (miR-15a) and 13 (miR-16) of the 15 patients analyzed, these miRs were absent or weakly expressed in cancer epithelial cells, while their normal counterpart displayed a marked staining for both miRs (FIG. 1b,c and FIG. 8).

Scoring was performed using a semiquantitative system. The staining intensity for both normal and tumor cells included 4 scores: no staining (score 0), weak staining (score 1), moderately positive (score 2), and strongly positive (score 3). In the vast majority (9/15 for miR-15a and 8/15 for miR-16) of cases, tumor cells were completely negative (score 0) or displayed a weak staining (3/15 for miR-15a and 5/15 for miR-16; score 1) while the remaining (3 for miR-15a and 2 for miR-16) cases showed a moderate staining (score 2) of tumor cells. Both basal and luminal non neoplastic cells showed diffuse and constant miR expression, ranging from moderately (12/15 for miR-15a and 9/15 for miR-16) to strongly positive (3/15 for miR-15a and 6/15 for miR-16). Overall, the majority of the tumor samples analyzed showed an overt decrease in the level of both miRs as compared to the normal tissue, one of the prerequisites for the definition of classical tumor suppressor genes.

Stable Expression of a miR-15almiR-16 Decoy in RWPE-1 Recapitulates the Tumor Phenotype In order to explore the role of miR downregulation in the molecular mechanisms that regulate prostate cancer, we investigated the involvement of miR-15a/miR-16 loss in the course of tumorigenesis and exploited a depletion strategy in the untransformed and growth factor dependent prostate cell line RWPE-1, immortalized with human papilloma virus 18 [18]. For this purpose, we engineered a lentiviral vector named TW3'UTR (TW3'), in which we inserted multiple antisense sequences for miRs silencing to create a TW3'UTR decoy miR-15a/miR-16 vector (decoy15/16) (FIG. 2a). This vector produces a stable EGFP transgene with multiple matching sequences for both miRs into 3' untranslated region (3'UTR). The vector also includes a puromycin resistance cassette to selectively isolate transduced cells.

Decoy transcript silencing was validated by Northern blotting and flow cytometry analysis, which showed a specific fluorescence reduction consistent with miR-15a/miR-16 binding to the EGFP 3'UTR (FIG. 9a, 9b). Along with diminished EGFP-derived fluorescence (FIG. 10a), we observed a significant decrease of both miRs in decoy15/16 infected RWPE-1 cells (FIGS. 2b and 10b), whose levels became slightly higher than those detected in 13q14-deleted LNCaP prostate cancer cell line[19]. A similar decrease in miR-15a/miR-16 expression was observed in primary prostate tumor cells expressing normal levels of both miRs (FIG. 2b).

We next analyzed the growth kinetics of prostate cells upon loss of miR-15a/miR-16. RWPE-1 cells infected with decoy15/16 (RWPE-1decoy15/16) showed a considerable increase in the growth rate as compared to control cells infected with empty vector TW3'UTR (RWPE-1TW3') (FIG. 2c). Likewise, downregulation of miR-15a/miR-16 in primary prostate tumor cells resulted in enhanced growth and considerably prolonged survival in culture as compared with control cells (FIG. 2c and data not shown). Such accelerated growth correlated with a significant increase in the percentage of cells at the S/G2-M phases of the cell cycle (FIG. 2d), indicating that targeting of miR-15a and miR-16 is able to enhance prostate cell proliferation. Thus, there is a causal relationship between miR-15a/miR-16 loss of expression and deregulated growth in untransformed prostate cells.

Anchorage-independent growth is regarded as an in vitro surrogate to determine the tumorigenic capacities of transformed cells. We analyzed the effect of miR-15a/miR-16 depletion on the ability of RWPE-1 cells to form colonies in soft-agar. Differently from wild-type and control vector-transduced cells, RWPE-1 decoy15/16 cells were able to grow and give rise to colonies that exhibited anchorage independent growth (FIG. 2e). To investigate the possible effect of miR-15a/miR-16 downregulation on prostate cell migration, we performed a motility assay with RWPE-1 decoy15/16 and RWPE-1TW3' cell lines on Boyden chambers containing porous polycarbonate membranes and maintained in two different conditions, either in conventional or in cancer fibroblast-conditioned medium. Unlike control cells, RWPE-1decoy15/16 cells revealed intrinsic migration capacity in standard medium, and enhanced invasion and motility in cancer fibroblast-conditioned medium (FIG. 2f). These data established a direct correlation between miRs silencing, increased proliferation and migration.

Reconstitution of miR-15a and miR-16 Expression Induces Growth Arrest and Apoptosis in Prostate Tumor Cells To determine the consequence of miR-15a/miR-16 restoration in prostate cancer cells, the miR-15a/miR-16-1 cluster was amplified by PCR from human genomic DNA and subcloned into the TWEEN[20] lentiviral vector (TWmiR-15a/miR-16) (FIG. 3a). Then miR-defective LNCaP cells were transduced with this vector to obtain a near-physiological expression of miR-15a and miR-16, as evaluated by real time PCR (FIG. 3b). The RWPE-1 cell line was infected in parallel as a control reference to check for possible toxicity deriving from miR-15a/miR-16 overexpression. miR transduced LNCaP cells underwent growth arrest and apoptosis, while RWPE-1 did not show any sign of toxicity (FIGS. 3c,d). After gene transfer, the few surviving TWmiR-15a/miR-16 LNCaP cells underwent massive counterselection that was not observed in LNCaP cells transduced with control vector or in TWmiR-15a/miR-16 RWPE-1 cells (FIG. 3e), suggesting that loss of miR-15a/miR-16 creates addiction in transformed cells.

The tumor suppressor Rb is located 1.7 Mb upstream of miR-15/16 in the 13q14 region [11] [21]. To rule out that the absence of Rb may contribute to the tumor phenotype of 13q14 deleted LNCaP cells, we investigated Rb expression in LNCaP cells lacking miR-15/16. Western blotting analysis showed that miR-defective LNCaP cells did not lose the expression of Rb (FIG. 11a), indicating that they represent a useful system to study the involvement of miR-15/16 deletion in prostate cancer progression. Moreover, the analysis of primary prostate cells did not show a significant correlation between Rb and miR-15/16 levels (FIG. 11b), suggesting that the loss of miR-15/16 is often independent of the absence of Rb.

Docetaxel is the standard treatment for androgen-independent prostate tumors [2]. The ability of miR-15a and miR-16 to target Bcl-2 may influence the pharmacological response of prostate cells. Hence, we reasoned that abrogation of this regulatory circuit through loss of miR-15a/miR-16 expression in prostate cancer might enhance chemoresistance and reduce the efficacy of medical treatments. To validate our hypothesis, we analyzed the chemosensitivity of RWPE-1 cells transduced with decoy15/16 cells. Upon targeting of miR-15a/miR-16, RWPE-1 became more resistant to docetaxel treatment and behaved similarly to miR-15a/miR-16-defective LNCaP cells, both in terms of caspase activation and cytotoxic response (FIG. 12a,b). In order to determine the possible additive effect of miRs and chemotherapy, we evaluated the cytotoxic activity of docetaxel on miR-15a/miR-16 reconstituted LNCaP cells.

miR-15a/miR-16 expressing prostate cancer cells were massively killed by docetaxel exposure, while the empty vector-transduced population was scarcely sensitive (FIG. 12b). To confirm the data obtained in cell lines, we performed similar experiments on primary cells from miR-defective primary tumors. Purified primary prostate cells from tumoral and control tissues were transduced with TWmiR-15a/miR-16 or TW empty vector. Transgenic miR expression was evaluated by real time PCR (FIG. 3f). Restoration of miR-15a/miR-16 expression dramatically impacted on the viability of primary prostate tumor cells, while normal cells did not suffer from toxicity upon miR overexpression (FIG. 3g). These data suggest a miR-elicited pro-apoptotic effect in tumoral cells that might be exploited to sensitize cells to chemotherapeutic regimens.

To verify this possibility, prostate primary cells transduced with miR-15a/miR-16 were treated with docetaxel. As for LNCaP cells, the combination of miRs and chemotherapy was dramatically effective in killing miR-15a/16 defective primary prostate cancer cells (FIG. 12c). In contrast, early stage primary prostate cancer cells expressing miR-15a/16 acquired resistance to docetaxel upon targeting of miR-15a/16 (FIG. 12c), indicating a clear dependence on miR-15a/miR-16 expression for chemosensitization. Thus, reconstitution of miR-15a/miR-16 in defective prostate cancer cells induces a considerable cytotoxic activity that is further increased by the combined use of chemotherapy.

miR-15a/miR-16 Target the Cyclin D1 and Wnt3a 3'UTR miR-15 and miR-16 can directly target Bcl-2 mRNA and thus induce apoptosis in chronic lymphocytic leukemia cells [16]. However, based on the increased proliferation and invasiveness observed in untransformed prostate cells depleted of miR-15a and miR-16, we speculated that additional targets of these miRs could be involved in such a malignant phenotype. Therefore, we ran a computer-assisted search that generated a list of >400 potential targets, which we refined by applying increasing stringency in the selection criteria (see Methods). Among the possible candidates, we analyzed further cyclin D1, Wnt3a and Pim-1, three genes whose functions were directly associated with cancer progression and invasion [22-24].

Cyclin D1 and Wnt3a showed a particularly high prediction ranking, while Pim-1 displayed a higher estimated false discovery rate (Table 2). To validate our targets, we subcloned the 3'UTR of these genes at the 3' of the cDNA encoding luciferase in an expression construct and performed cotransfection experiments with miR-15a/miR-16. We narrowed our analysis to 1 kb regions harbouring the putative miR-15a/miR-16 target sites. The Bcl-2 3'UTR was tested in parallel as positive control. Luciferase assay was performed by cotransfecting pGL3-3'UTR vectors along with synthetic miR-15a, miR-16 and a control miR with a scrambled sequence.

We observed a consistent reduction in reporter activity only when positive control and putative target vectors were assayed in combination with either miR-15a or miR-16, but not with scrambled oligos (FIG. 4a). The luciferase activity decrement indicated a direct interaction of both miR-15a and miR-16 with cyclin D1 and Wnt3a 3'UTRs to the same extent as measured for Bcl-2, while Pim-1 UTR could be confirmed as a non-targeted region (FIG. 4a and FIG. 13a). As an endeavour to refine the identification of regulatory sites, we mutated the "seed" sequence of the putative target sites in the cyclin D1 and Wnt3a 3'UTRs (FIG. 13b).

3'UTR mutations rendered the constructs immune to regulation by miR-15a/miR-16, evidencing the specific binding of both miRs to the cyclin D1 and Wnt3a mRNAs (FIG. c).

To further validate our findings, we evaluated the variation in the target gene proteins upon modulation of miR-15a/miR-16. Protein lysates were prepared from cells transduced so as to increase (TWmiR-15a/miR-16) or decrease (decoy15/16) the levels of miR-15a/miR-16 with respect to a control (TW or TW3'). For the depletion experiments, we examined the levels of target proteins in RWPE-1 cells and their transformed derivative RWPE-2. Western blot analysis consolidated the data obtained with the reporter gene assays for Bcl-2, Wnt3a and cyclin D1, showing a significant increase in their protein levels upon expression of the decoy15/16 (FIG. 4b, FIG. 14a). These data were also confirmed in a complementary approach using TWmiR-15a/miR-16 to increase the levels of miR-15a and miR-16 in LNCaP and miR defective primary tumor cells, resulting in a sensible decrease of all the three proteins (FIG. 4b, FIG. 14b,c).

To consolidate the data obtained with lentiviral vectors, sense and antisense oligos specific for miR-15 and miR-16 were delivered into wild type RWPE-1 cells. As expected, miR-15 and 16 oligos reduced the expression of Bcl-2, cyclin D1 and Wnt3a, while cells treated with antisense oligos showed a target protein up-regulation comparable to RWPE-1 Decoy15/16 cells (FIG. 4c), which was reverted following transfection with miR-15 and 16 oligos (FIG. c). We next analyzed miR-15a/miR-16 defective prostate tumors for expression of Bcl-2, cyclin D1 and Wnt3a. The availability of reliable reagents for two of the three targets allowed the immunohistochemical analysis of Bcl-2 and cyclin D1, which were found upregulated in miR-15a/miR-16 defective prostate tumors (FIG. 4d). Moreover, the immunoblot analysis of primary prostate cultures indicated a significant inverse correlation ($P=0.008$) between miR-15/16 expression and target protein levels (FIG. 4e).

Wnt3a signalling promotes the increase in β-catenin protein levels and the activation of other survival and proliferation pathways through the phosphorylation of ERK and Akt [25, 26]. Accordingly, the analysis of TWmiR-15a/miR-16 LNCaP and RWPE-1decoy15/16 cells showed that the presence of miR-15a and miR-16 was associated with a decreased expression of β-catenin and a reduced phosphorylation of AKT and ERK (FIG. 4f and FIG. 14d). Moreover, the increased expression of cyclin D1 in RWPE-1decoy15/16 cells correlated with an increased phosphorylation of Rb, whereas the exogenous expression of miR15/16 in LNCaP cells produced an opposite effect (FIG. 4f and FIG. 14d).

Thus, miR-15a and miR-16 act by targeting the mRNAs of Bcl-2, cyclin D1 and Wnt3a, which promote prostate cell survival, proliferation and invasion.

In order to clarify the role of the single target genes in prostate cancer progression, we infected RWPE-1 cells with virus particles containing transgenes for Bcl-2, cyclin D1 and Wnt3a. Both cyclin D1 and Wnt3a upregulation considerably increased prostate cell growth and the percentage of cells at the S/G2-M phase of the cell cycle, while exogenous expression of Bcl-2 did not alter significantly cell growth or cell cycle profile (FIG. 15a, b). The in vitro migration analysis revealed that Wnt3a promotes the invasion and motility of RWPE-1 cells, which was not affected by exogenous expression of Bcl-2 or cyclin D1 (FIG. 15c), suggesting that the increase expression Wnt3a and cyclin D1 mediate the accelerated growth after miR-15a and miR-16 downregulation, while Wnt3a upregulation is responsible for the enhanced migration.

To investigate the contribution of the three targets of miR-15a and miR-16 in docetaxel resistance, Bcl-2, cyclin D1 and Wnt3a transduced RWPE-1 cells were treated with the chemotherapeutic drug. After single gene transduction, only Bcl-2 cells was able to protect prostate cells from docetaxel (FIGS. 16a,b). Moreover, the concomitant upregulation of Bcl-2 and Wnt3a synergistically counteract the cytotoxic activity of docetaxel (FIG. 16a,b), suggesting that both targets mediated the enhanced survival that follows the loss of miR-15a and miR-16.

Targeting of miR-15a/miR-16 Promotes Tumorigenesis and Tumor Progression

To further elucidate the significance of miR-15a/miR-16 loss as a critical step in cancer development and progression, NOD-SCID mice were used as an in vivo model for prostate cancer xenografts. Since miR silencing proved sufficient to enhance the proliferation of RWPE-1 cells and conferred a growth and migratory behaviour reminiscent of neoplasms, we investigated whether the loss of function of miR-15a and miR-16 would endow the non-tumorigenic cell line RWPE-1 with the ability to form tumors in NOD-SCID mice. RWPE-1 transduced with either decoy15/16 or empty vector were injected subcutaneously into 4 week old male mice. RWPE-1 decoy15/16 were able to consistently produce slow growing tumors, whereas RWPE-1 TW3' did never develop into a tumoral mass (FIG. 5a).

To determine the possible synergism with other oncogenic lesions, we devised a similar experiment with the RWPE-2 cell line transduced with decoy15/16 vector. RWPE-2 cells are able to produce small tumors in vivo, as they have been transformed by insertion of the ki-RAS gene into RWPE-1 cells [18]. RWPE-2 cells have the same levels of miR-15a and miR-16 expression of RWPE-1 cells, as revealed by real time PCR (data not shown). When injected into NOD-SCID mice, RWPE-2decoy15/16 produced tumors with a significantly increased volume as compared with TW3' transduced cells (FIG. 5b). We next injected subcutaneously in NOD-SCID mice a combination of wild type (70%) and decoy15/16-transduced (30%) RWPE-1 cells. After tumor formation, we analyzed by immunohistochemistry the localization of decoy15/16-transduced cells through the staining of the GFP reporter. Such analysis revealed that miR-15a/miR-16 downregulation enhances prostate cell invasion, as indicated by the presence of GFP+ cells in the tumor front and in invasive tumor islands (FIG. 5c). Hence, miR-15a/miR-16 downregulation can contribute to prostate cancer transformation, suggesting a causative role in tumor progression.

Antagomir oligonucleotides can efficiently knockdown specific miRNAs in most tissue in vivo for as long as 1 month after injection [5, 27]. To investigate the role of miR-15a/miR-16 downregulation in prostate in vivo, we injected into BALB/c mouse prostate a single dose of mixed antagomirs selective for miR-15a and 16. As controls, mice were injected with either saline buffer or antagomir selective for the unrelated cardio-specific miR-1. Inhibition by antagomir was evaluated using Real time PCR assay from one week to one month post injection, resulting in 40-85% repression of endogenous miR-15a and 16 over antagomir-1 treated mice (data not shown). Five weeks after antagomir injection, histological analysis showed a marked prostatic hyperplasia and a modest acini disruption in antagomir-15/16 treated mice, while control mice did not show any alteration (FIG. 5d), in line with the potential tumor suppressor role played by the cluster miR-15a/miR-16.

Therapeutic Effect of miR-15a/miR-16 Reconstitution on Prostate Tumor Xenografts The tumor suppressor activity of the cluster miR-15a/miR-16 seems required for the homeostatic regulation of the prostate epithelial tissue. Our in vitro experiments showed that miR-15a/miR-16 reconstitution in defective prostate cells resulted in growth arrest and apoptosis. To evaluate the effect of restored miR-15a/miR-16 expression in an in vivo tumoral model, $8 \times 10^6$ LNCaP cells resuspended in Matrigel were injected subcutaneously in NOD-SCID mice. This procedure gave rise to the formation of tumors within 2-3 weeks (FIG. 6a). Four weeks postinjection, tumor xenografts were locally treated with TWmiR-15a/miR-16 or TW control viruses in order to obtain the transduction of the vast majority of the cancer cells resident into the tumor mass (FIG. 6b). TWmiR-15a/miR-16 injected tumors underwent growth arrest within one week from treatment, while similar tumors did not alter their growth after injection with empty-vector virus. Moreover, 2 weeks after virus treatment, we observed a considerable volume regression of TWmiR-15a/miR-16 infected tumors, while control tumors continued to grow exponentially (FIG. 6a). The anti-tumor effect of miR-15a/miR-16 treatment was particularly potent and not confined to tumor reduction, as the histological analysis of the residual masses indicated the presence of diffuse necrosis with rare areas containing surviving cells (FIG. 6c). Thus, in line with the in vitro observations, restoration of miR-15a and miR-16 in defective prostate cancer cells resulted in dramatic tumor regression.

Discussion

Advanced prostate cancer is a severe condition frequently leading to patients' death [1]. The identification of the mechanisms responsible for tumor initiation and progression may contribute significantly to devise more effective therapeutic strategies. Here, we demonstrated that miR-15a and miR-16 are downregulated in a considerable percentage of prostate tumors, particularly in advanced stages. In vitro and in vivo targeting of miR-15a and miR-16 enhances prostate cell survival while promoting cell growth and invasion. Both miRs are able to target Bcl-2, cyclin D1 and Wnt3a, whose protein levels are consequently upregulated when the miRs are downregulated and may contribute to potentiate tumor cell survival, proliferation and invasion.

Bcl-2 protein is barely detectable in normal human prostatic secretory epithelial cells, whereas high levels of this pro-survival oncoprotein are found in neoplastic prostate tissues, particularly in hormone-independent prostatic adenocarcinomas[28-30]. Accumulating evidence indicates the involvement of Bcl-2 in human prostate cancer development [31]. Increased Bcl-2 expression promotes the resistance to chemotherapy[17] and androgen depletion[28]. Thus, Bcl-2 upregulation in miR-15a/miR-16 defective prostate cancer may contribute to tumor progression and resistance to therapy.

Cyclin D1 is an essential regulator of cell cycle progression that interacts with cyclin-dependent kinase (CDK) 4/6 to form an active kinase complex that phosphorylates the retinoblastoma tumor suppressor, enabling the cell to undergo the G1/S phase transition of the cell cycle. About 40-50% of primary carcinoma overexpress cyclin D1, which is clearly implicated in the unrestrained proliferation observed in many tumors [22, 32]. The expression of cyclin D1 significantly predicted cancer-related survival and was associated with the Ki67 proliferative index in prostate cancer patients [22, 33]. Moreover, cyclin D1 expression correlated with prostate tumor grading and staging [33, 34], suggesting that its overexpression may represent a critical oncogenic event for cancer spreading.

Several lines of evidence indicate a possible role of Wnt signalling in the oncogenic process leading to prostate cancer [23, 35]. The activation of the Wnt pathway results in inhibition of β-catenin phosphorylation by GSK3β, with consequent β-catenin accumulation and transcription of a variety of cancer associated genes [23, 36]. In addition, Wnt3a promotes the activation of ERK and AKT with consequent phosphorylation of downstream substrates implicated in cell survival and proliferation [25, 26]. A recent study demonstrated a central roles for AKT and ERK signalling pathways in promoting prostate tumor progression to hormone-refractory state [37]. Moreover, a unique role for the Wnt3a growth factor in inducing androgen receptor-mediated transcription and cell growth in prostate cancer has been demonstrated, suggesting that its aberrant expression may play a critical role in prostate tumor progression[38].

The ability of miR-15a/miR-16 to target Wnt3a may have considerable implications in prostate cancer. Upon Wnt3a upregulation, miR-defective tumors accumulate β-catenin and activate a series of signalling events involved in cancer development and progression, such as the AKT and ERK pathways. Hence, it is reasonable to assume that loss of miR-15a/miR-16 during prostate carcinogenesis might represent an important oncogenic step mediated by Bcl-2, cyclin D1 and Wnt3a overexpression. Higher levels of Bcl-2 and Wnt3a may increase prostate cell growth by inhibiting apoptosis in unfavourable conditions, as in case of anti-androgen or cytotoxic therapies. Both cyclin D1 and Wnt3a are able to promote the proliferation of prostate cells upon silencing of miR-15a and miR-16, while the single increase in Wnt3a expression seems responsible for the enhanced migration and invasiveness typical of the advanced stages. Although it is theoretically possible that other targets may be involved in the oncogenic activities promoted by the loss of miR-15/miR-16, Bcl-2, cyclin D1 and Wnt3a play a key role in prostate cancer progression and represent the most likely target candidates for the tumor suppressor activity of this miR cluster.

The data presented here has considerable therapeutic significance for advanced prostate cancer. Clinical trials aimed at assessing the therapeutic potential of antisense oligodeoxynucleotides targeting Bcl-2 gene expression in prostate cancer have been undertaken [39]. The reintroduction of miR-15a/miR-16 could be theoretically more effective due to the simultaneous targeting of Bcl-2, cyclin D1 and Wnt3a, three major proteins involved in resistance to apoptosis and cancer cell proliferation.

In our experimental models, delivery of miR-15a and miR-16 in prostate cancer xenografts was able to induce a dramatic tumor regression. The cytotoxic effect of these miRs on both LNCaP and primary prostate tumor cells was striking, and further increased in the presence of docetaxel. Thus, although advanced prostate tumors are extremely heterogeneous in the clinical setting, it is likely that miR-15a and miR-16 can have a considerable therapeutic potential, both as single agents or in combination with chemotherapeutic drugs.

Advanced molecular therapies aimed at downmodulating the level of a given miR in model organisms have been successfully established [5, 27], while siRNA-based strategies for the introduction of artificial RNA guide strands in the RNA-induced signalling complex (RISC) proved their efficacy in primates[40]. We thus envision that the aim of restoring miR-15a/miR-16 function for prostate cancer therapy might take advantage of a siRNA mimicker, whereby the guide strand of these miRs might be embedded in a synthetic sequence or in its native pre-miR sequence context.

REFERENCES

All references cited herein are hereby incorporated by reference, unless otherwise apparent.
1. Jemal, A., et al., *Cancer statistics,* 2006. CA Cancer J Clin, 2006. 56(2): p. 106-30.
2. Pienta, K. J. and D. C. Smith, *Advances in prostate cancer chemotherapy: a new era begins.* CA Cancer J Clin, 2005. 55(5): p. 300-18.
3. Loberg, R. D., et al., *Pathogenesis and treatment of prostate cancer bone metastases: targeting the lethal phenotype.* J Clin Oncol, 2005. 23(32): p. 8232-41.
4. Bartel, D. P., *MicroRNAs: genomics, biogenesis, mechanism, and function.* Cell, 2004. 116(2): p. 281-97.
5. Care, A., et al., *MicroRNA-133 controls cardiac hypertrophy.* Nat Med, 2007. 13(5): p. 613-8.
6. Calin, G. A. and C. M. Croce, *MicroRNA signatures in human cancers.* Nat Rev Cancer, 2006. 6(11): p. 857-66.
7. Esquela-Kerscher, A. and F. J. Slack, *Oncomirs—microRNAs with a role in cancer.* Nat Rev Cancer, 2006. 6(4): p. 259-69.
8. Chang, T. C., et al., *Widespread microRNA repression by Myc contributes to tumorigenesis.* Nat Genet, 2007.
9. Calin, G. A., et al., *Human microRNA genes are frequently located at fragile sites and genomic regions involved in cancers.* Proc Natl Acad Sci USA, 2004. 101(9): p. 2999-3004.
10. Calin, G. A., et al., *A MicroRNA signature associated with prognosis and progression in chronic lymphocytic leukemia.* N Engl J Med, 2005. 353(17): p. 1793-801.
11. Calin, G. A., et al., *Frequent deletions and down-regulation of micro-RNA genes miR15 and miR16 at 13q14 in chronic lymphocytic leukemia.* Proc Natl Acad Sci USA, 2002. 99(24): p. 15524-9.
12. Dong, J. T., *Chromosomal deletions and tumor suppressor genes in prostate cancer.* Cancer Metastasis Rev, 2001. 20(3-4): p. 173-93.
13. Dong, J. T., J. C. Boyd, and H. F. Frierson, Jr., *Loss of heterozygosity at 13q14 and 13q21 in high grade, high stage prostate cancer.* Prostate, 2001. 49(3): p. 166-71.
14. Hyytinen, E. R., et al., *Three distinct regions of allelic loss at 13q14, 13q21-22, and 13q33 in prostate cancer.* Genes Chromosomes Cancer, 1999. 25(2): p. 108-14.
15. Calin, G. A., et al., *MicroRNA profiling reveals distinct signatures in B cell chronic lymphocytic leukemias.* Proc Natl Acad Sci USA, 2004. 101(32): p. 11755-60.
16. Cimmino, A., et al., *miR-15 and miR-16 induce apoptosis by targeting BCL2.* Proc Natl Acad Sci USA, 2005. 102 (39): p. 13944-9.
17. Leung, S., et al., *Synergistic chemosensitization and inhibition of progression to androgen independence by antisense Bcl-2 oligodeoxynucleotide and paclitaxel in the LNCaP prostate tumor model.* Int J Cancer, 2001. 91 (6): p. 846-50.
18. Bello, D., et al., *Androgen responsive adult human prostatic epithelial cell lines immortalized by human papillomavirus 18.* Carcinogenesis, 1997. 18(6): p. 1215-23.
19. Nupponen, N. N., et al., *Genetic alterations in prostate cancer cell lines detected by comparative genomic hybridization.* Cancer Genet Cytogenet, 1998. 101(1): p. 53-7.
20. Felli, N., et al., *MicroRNAs 221 and 222 inhibit normal erythropoiesis and erythroleukemic cell growth via kit receptor down-modulation.* Proc Natl Acad Sci USA, 2005. 102(50): p. 18081-6.
21. Yin, Z., et al., *Limiting the location of a putative human prostate cancer tumor suppressor gene at chromosome 13q14.3.* Oncogene, 1999. 18(52): p. 7576-83.
22. Sherr, C. J., *Cancer cell cycles.* Science, 1996. 274(5293): p. 1672-7.
23. Clevers, H., *Wnt/beta-catenin signaling in development and disease.* Cell, 2006. 127(3): p. 469-80.
24. Dhanasekaran, S. M., et al., *Delineation of prognostic biomarkers in prostate cancer.* Nature, 2001. 412(6849): p. 822-6.
25. Almeida, M., et al., *Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT.* J Biol Chem, 2005. 280(50): p. 41342-51.
26. Yun, M. S., et al., *Both ERK and Wnt/beta-catenin pathways are involved in Wnt3a-induced proliferation.* J Cell Sci, 2005. 118(Pt 2): p. 313-22.
27. Krutzfeldt, J., et al., *Silencing of microRNAs in vivo with 'antagomirs'.* Nature, 2005. 438(7068): p. 685-9.
28. Raffo, A. J., et al., *Overexpression of bcl-2 protects prostate cancer cells from apoptosis in vitro and confers resistance to androgen depletion in vivo.* Cancer Res, 1995. 55(19): p. 4438-45.
29. Colombel, M., et al., *Detection of the apoptosis-suppressing oncoprotein bcl-2 in hormone-refractory human prostate cancers.* Am J Pathol, 1993. 143(2): p. 390-400.
30. Gleave, M., et al., *Progression to androgen independence is delayed by adjuvant treatment with antisense Bcl-2 oligodeoxynucleotides after castration in the LNCaP prostate tumor model.* Clin Cancer Res, 1999. 5(10): p. 2891-8.
31. McDonnell, T. J., et al., *Expression of the protooncogene bcl-2 in the prostate and its association with emergence of androgen-independent prostate cancer.* Cancer Res, 1992. 52(24): p. 6940-4.
32. Donnellan, R. and R. Chetty, *Cyclin D1 and human neoplasia.* Mol Pathol, 1998. 51(1): p. 1-7.
33. Aaltomaa, S., M. Eskelinen, and P. Lipponen, *Expression of cyclin A and D proteins in prostate cancer and their relation to clinopathological variables and patient survival.* Prostate, 1999. 38(3): p. 175-82.
34. Drobnjak, M., et al., *Overexpression of cyclin D1 is associated with metastatic prostate cancer to bone.* Clin Cancer Res, 2000. 6(5): p. 1891-5.
35. Chesire, D. R. and W. B. Isaacs, *Beta-catenin signaling in prostate cancer: an early perspective.* Endocr Relat Cancer, 2003. 10(4): p. 537-60.
36. Yardy, G. W. and S. F. Brewster, *Wnt signalling and prostate cancer.* Prostate Cancer Prostatic Dis, 2005. 8(2): p. 119-26.
37. Gao, H., et al., *Combinatorial activities of Akt and B-Raf/Erk signaling in a mouse model of androgen-independent prostate cancer.* Proc Natl Acad Sci USA, 2006. 103(39): p. 14477-82.
38. Verras, M., et al., *Wnt3a growth factor induces androgen receptor-mediated transcription and enhances cell growth in human prostate cancer cells.* Cancer Res, 2004. 64(24): p. 8860-6.
39. Tolcher, A. W., et al., *A phase II, pharmacokinetic, and biological correlative study of oblimersen sodium and docetaxel in patients with hormone-refractory prostate cancer.* Clin Cancer Res, 2005. 11 (10): p. 3854-61.
40. Zimmermann, T. S., et al., *RNAi-mediated gene silencing in non-human primates.* Nature, 2006. 441(7089): p. 111-4.

41. Navone, N. M., M. Olive, and P. Troncoso, *Isolation and culture of prostate cancer cell lines*. Methods Mol Med, 2004. 88: p. 121-32.
42. Nelson, P. T., et al., *RAKE and LNA-ISH reveal microRNA expression and localization in archival human brain*. Rna, 2006. 12(2): p. 187-91.
43. Bonci, D., et al., *'Advanced' generation lentiviruses as efficient vectors for cardiomyocyte gene transduction in vitro and in vivo*. Gene Ther, 2003.10(8): p. 630-6.
44. Lewis, B. P., et al., *Prediction of mammalian microRNA targets*. Cell, 2003. 115(7): p. 787-98.
45. Lewis, B. P., C. B. Burge, and D. P. Bartel, *Conserved seed pairing, often flanked by adenosines, indicates that thousands of human genes are microRNA targets*. Cell, 2005. 120(1): p. 15-20.
46. John, B., et al., *Human MicroRNA targets*. PLoS Biol, 2004. 2(11): p. e363.
47. Krek, A., et al., *Combinatorial microRNA target predictions*. Nat Genet, 2005. 37(5): p. 495-500.
48. Tashiro E et al. Tashiro E, Tsuchiya A, Imoto M. Functions of cyclin D1 as an oncogene and regulation of cyclin D1 expression. Cancer Sci. 2007 May;98(5):629-35. Epub Mar. 14, 2007. Review.
49. Tashiro E, Maruki H, Minato Y, Doki Y, Weinstein I B, Imoto M. Overexpression of cyclin D1 contributes to malignancy by up-regulation of fibroblast growth factor receptor 1 via the pRB/E2F pathway. Cancer Res. Jan. 15, 2003;63(2):424-31
50. Aaltomaa S, Eskelinen M, Lipponen P. Expression of cyclin A and D proteins in prostate cancer and their relation to clinopathological variables and patient survival. Prostate. Feb. 15, 1999;38(3):175-82.
51. Yoshino T, Shiina H, Urakami S, Kikuno N, Yoneda T, Shigeno K, Igawa M. Bcl-2 expression as a predictive marker of hormone-refractory prostate cancer treated with taxane-based chemotherapy. Clin Cancer Res. Oct. 15, 2006;12(20 Pt 1):6116-24
52. CANCER RESEARCH 63, 424-431, Jan. 15, 2003, Overexpression of Cyclin D1 Contributes to Malignancy by Up-Regulation of Fibroblast Growth Factor Receptor 1 via the pRB/E2F Pathway1 Etsu Tashiro, Hiroko Maruki, Yusuke Minato, Yuichiro Doki, I. Bernard Weinstein, and Masaya Imoto2
53. CANCER RESEARCH 52, 571-577, Feb. 1, 1992 Basic Fibroblast Growth Factor in Human Prostate Cancer Cells1 Takahisa Nakamoto, Chawnshang Chang, Ankun Li, and Gerald W. Chodak2
54. Clin Lymphoma Myeloma. 2006 May;6(6):455-7. Bcl-2 gene expression as a predictor of outcome in diffuse large B-cell lymphoma. Shivakumar L, Armitage J O.
55. CANCER RESEARCH 52, 571-577, Feb. 1, 1992 Basic Fibroblast Growth Factor in Human Prostate Cancer Cells1 Takahisa Nakamoto, Chawnshang Chang, Ankun Li, and Gerald W. Chodak2
56. Overexpression of Cyclin D1 Is Associated with Metastatic Prostate Cancer to Bone Marija Drobnjak, 2 Iman Osman, Howard I. Scher, Melissa Fazzari, and Carlos Cordon-Cardo3
57. The Role of Cell Cycle Regulatory Protein, Cyclin D1, in the Progression of Thyroid Cancer. Songtao Wang, M. D., Ph.D., Ricardo V. Lloyd, M. D., Ph.D., Michael J. Hutzler, M. D., Marjorie S. Safran, M. D., Nilima A. Patwardhan, M. D., Ashraf Khan, M. D. Mod Pathol 2000; 13(8):882-887
58. Treatment options in androgen-independent prostate cancer. Cancer Invest. 1999;17(2):137-44. Lara P N Jr, Meyers F J. Review
59. Int J Cancer. Jul. 20, 2004;110(6):800-6. Progression to androgen-independent LNCaP human prostate tumors: cellular and molecular alterations. Zhou J R, Yu L, Zerbini L F, Libermann T A, Blackburn G L
60. Antiangiogenic therapy and tumor progression. Blagosklonny M V. Cancer Cell. 2004 January;5(1): 13-7.
61. Vascular endothelial growth factor: basic science and clinical progress. Ferrara N. Endocr Rev. 2004 August;25 (4):581-611.
62. Roles of HMGA proteins in cancer. Fusco A, Fedele M. Nat Rev Cancer. 2007 December;7(12):899-910.
63. MicroRNA-133 controls cardiac hypertrophy. Care A, et al Nat Med. 2007 May;13(5):613-8. Epub Apr. 29, 2004.

EXAMPLE 2

BTG2 is a prototype member of the BTG/Tob family of antiproliferative proteins, initially identified as early growth response genes induced by growth factors and tumor promoters. BTG2 has subsequently been characterized as a pan-cell cycle modulator and a major effector of p53-induced proliferation arrest due to its ability to inhibit the expression of cyclin D1 and the phosphorylation of Rb (Boiko AD 2006). Repression of BTG2 cooperates with Ras activation in inducing cell transformation, indicating BTG2 as a tumor suppressor gene. BTG2 may also be involved in the direct induction of apoptosis in tumor cells, as its mouse ortholog TIS21 participates to mitochondrial depolarization and cell death by binding to the prolyl isomerase Pin1 (Hong J W 2005). BTG2 has lately been demonstrated to enhance chemotherapy-induced death of cancer cells by controlling the generation of oxidation products (Lim, Y B 2008 and Example 2, Refs-1-8).

MicroRNA-21 (miR-21) has been found to be upregulated in microarray studies involving breast, colon, lung, pancreas, prostate and stomach tumors (Volinia et al., 2006). MiR-21 knockdown induces apoptosis in glioblastoma cells (Chan et al., 2005) and sensitizes cholangiocytes to chemotherapeutic agents (Meng et al., 2007), while its overexpression inhibits apoptosis in myeloma cells (Loffler et al., 2007). MiR-21 has been shown to target and down-regulate the expression of the tumor suppressors tropomyosin 1 (Zhu et al., 2007), phosphatase and tensin homolog (PTEN) (Meng et al., 2007), and programmed cell death 4 (PDCD4) and to promote cell invasion and metastasis (Asangani et al., 2007). Moreover, interfering with miR-21 activity inhibits tumor growth in vivo and in vitro (Si et al., 2007), demonstrating the importance of this gene in regulating tumorigenesis.

We have shown that miR-21 expression is elevated in prostate cancer and identified BTG2 as a target of miR-21. We have shown that miR-21 overexpression reduces BTG2 levels and increases the growth of prostate cancer cells. In particular, we show that infection of prostate cancer cells with a lentiviral vector that specifically abrogates the action of miR-21 on BTG2 transcripts results in increased BTG2 expression and inhibits the growth of tumor cells in vitro and in vivo. The use of such vectors allowed to demonstrate that the deregulated expression of miR-21 contributes to the expansion of prostate tumors through the specific silencing of BTG2.
Elevated BTG2 Expression Decreases Prostate Cancer Cell Tumorigenicity.

Exogenous expression of BTG2 in prostate cancer cell lines results in decreased rates of cell proliferation (FIGS. 17 and 18). We sought to investigate the role of miR-21-mediated BTG2 modulation by producing a model system in which the expression of BTG2 was regulated in an endogenous fashion by specifically interfering with miR-21 action on BTG2 3'UTR.

Therefore, we engineered a lentiviral vector in which we inserted the 3'UTR of BTG2, the miR-21 binding sites in the 3'UTR of EGFP (Enhanced Green Fluorescent Protein) and a puromycin resistance cassette to selectively isolate transduced cells (FIG. 17a). This vector was called TWEEN-3'-UTR-BTG2 (TW3'UTRBTG2) and was used to produce a stable EGFP transgene with a chimera 3'UTR able to bind miR-21 and to control BTG2 transcription in RWPE-2 cells. Chimera transcript targeting was validated by flow cytometry analysis of BTG2 levels in RWPE-2 cells transduced with TW3'UTRBTG2, which showed significantly increased BTG2 levels in EGFP-expressing cells.

The effect of TW3'UTRBTG2 on restoring endogenous levels of BTG2 was validated also on 22Rv1 prostate cancer cells. Elevated BTG2 expression resulted in decreased growth rates in TW3'UTRBTG2-infected cells which was due mainly to a decrease of cells in the S phase of the cell cycle (FIGS. 17c-d). According to the decreased proliferative activity of TW3'UTRBTG2-infected cells, we found significantly reduced levels of cyclin D1 and pRb, whereas the expression of PTEN, another known miR-21 target, remained unchanged (FIG. 17e). Levels of Cyclin D1 and pRb detected in TW3'UTRBTG2-infected cells approximated those found in the non-transformed prostate cell line RWPE-1 (which differs from RWPE-2 for the presence of oncogenic Ras) (FIG. 17e), suggesting that miR-21-mediated BTG2 silencing provides an important contribution to cellular transformation.

BTG2 upregulation impairs tumor growth rate in vivo. To investigate the influence of endogenous BTG2 modulation on tumor progression, we injected RWPE-2 cells subcutaneously into NOD-SCID mice and we treated the established prostate tumors with virus particles containing TW3' or TW3'UTRBTG2 vectors. Tumor size was evaluated starting from the time of virus injection for 12 days. While vector-treated tumors showed a constant growth rate, TW3'UTRBTG2-treated tumors showed a significant growth reduction starting from the time of virus injection (FIG. 19a).

In TW3'UTRBTG2-treated tumors, we found increased BTG2 levels compared to controls and areas of apoptotic cells, as revealed by H&E or TUNEL staining. These results indicate that restoration of endogenous BTG2 expression using such vectors specifically blocks miR-21 targeting and results in decreased aggressiveness and increased apoptosis of tumor cells in vivo.

Material and Methods

Cells and Antibodies.

RWPE-1, RWPE-2, LNCaP, 22Rv1, CaHPV10, PC3 and DU145 cell lines were obtained from ATCC and cultivated in the recommended medium. Tissue dissociation and isolation of primary prostate cells were performed as described [43]. Normal and neoplastic prostate surgical specimens were cultured in collagen-coated plates with BRFF-HPC1 medium (AthenaES, Baltimore, Md.), where cells grew in monolayer assuming a round-shape aspect. To determine the number of luminal cells and contaminating fibroblasts in tumor specimens, cells were stained for cytokeratin 18 (Clone5D3, NovoCastra) and Thy-1 (Clone 5E10, Becton Dickinson) respectively. The percentage of tumor cells was evaluated with anti-AMACR (Sanova Pharma, Vienna, Austria), while normal basal cells were detected with anti-p63 (BioGenex). For flow cytometry, Thy-1 staining was performed in PBS at 4° C. for 1 h, while the other antibodies were used after fixation and permeabilization with 2% parafolmaldehyde and 0.1% Triton X-100. The purity of human prostate primary cell preparation was confirmed by immunocytochemistry and only cultures with >85% enrichment of prostatic epithelial cells were used for subsequent experiments. Tissues were obtained from radical prostatectomy at the Department of Urology, S. Giovanni Bosco Hospital, Turin, Italy. All samples were collected with the informed consent of the patients. Antibodies against BTG2 were obtained as in Example 2, Ref.6 (Farioli-Vecchioli S. FASEB J. 2007 July; 21(9):2215-25. Epub Mar. 19, 2007).

Generation of Lentiviral Vectors and Gene Transfer.

For TWmiR-21 generation (TWmiR-21), miR-21 precursor DNA was PCR-amplified from human genomic DNA. The amplified fragment spanning 724 bp (MI0000077 genome context Coordinates (NCBI36 17: 55273409-55273480 [+]) was subcloned into the lentiviral vector TWEEN [22] under the CMV promoter. miRNA transgene expression was assayed by real time PCR using the appropriate oligonucleotides from Applied Biosystems. The TW3'UTR vector was obtained by modifying the EGFP 3'UTR of the TWEEN vector through the insertion of a multicloning site (XhoI-XbaI) that allowed the subcloning of the sequences of interest. Then the EGFP modified 3'UTR cassette was inserted under the CMV promoter control.

Moreover, a puromycin resistance gene was inserted under the PGK promoter control to allow the selection of transduced cells. To generate the TW3'UTRBTG2 vector, about 400 bp of 3'BTG-2UTR, containing miR-21 binding site, was subcloned into XhoI-XbaI multicloning site in TW3'UTR vector. This design was intended to optimize repression of the transgene in the presence of the miR21 and simultaneously derepression of endogenous BTG-2 mRNA. In fact from TW3'UTRBTG2 vector is generated an artificial transcript composed of EGFP with a 3'modified UTR containing a fragment of BTG-2 3'UTRs The sequestering/derepressing capacity of this vector was validated as reported in FIG. 4. In this figure all the experiments report derepression of BTG-2 protein translation underlying no activity on other miR-21 target genes such as PTEN. (FIG. 17). Recombinant lentiviral particles were obtained as described [46] by infecting cells with $1 \times 10^6$ (TU)/ml viral particles. For in vivo experiments, the viral supernatant was concentrated 250-fold by ultracentrifugation and injected directly into tumor xenografts of NOD-SCID mice.

Reporter Assays.

3'UTR segments of BTG2 was amplified by PCR from normal human genomic DNA and subcloned into the 3'UTR of the firefly luciferase coding sequence into pGL3-Promoter (Promega). Then K562 ($5 \times 10^4$ cells per well) were transfected using Lipofectamine 2000 (Invitrogen) following the manufacturer's instructions. Transfection mix included: (a) 0.8 μg of pGL3-3'UTR plasmid and 50 ng of the control vector pRL-TK (Promega); (b) 25 μmol of either non-targeting RNA control (scrambled) or miR-21 oligonucleotide (Ambion). Forty-eight hours post-transfection, firefly and renilla luciferase activities were measured using the Dual Luciferase Assay kit (Promega). Transfection efficiencies were normalized by calculating the ratio firefly/renilla. For each construct the relative luciferase activities were calculated by dividing the values obtained in the transfection of miR-21 by those of miR scrambled. Each experiment was performed in duplicate and replicated five times.

Flow Cytometry and Viability Assays.

For cell cycle determination, $2.5 \times 10^5$ RWPE-2TW3' and RWPE-2BTG2-3'UTR cells were analyzed with the BD Pharmingen BrdU Flow Kit staining protocol. Cells were seeded in 6 wells plate for 24 h. Then BrdU was added in culture medium and maintained for 1 h at 37° C. in incubator.

Fixation and permeabilization of the cells was performed with BD Cytofix/Cytoperm Buffer following the protocol indication. Cells were stained with anti-BrdU-APC for 20 minutes at room temperature and treated with 7-AAD before FACS analysis. BrdU-unlabelled cells from the same population were used as negative control. Cells were analyzed with LSR II (BD). Cell growth and death was evaluated by trypan blue staining, Apo-percentage assay (Biocolor) and Cell Titer kit (Promega).

Statistical analysis. Data are presented as the mean±s.d. Results of BrdU assays were analyzed by two-way ANOVA and Bonferroni post-tests.

Discussion

The functional consequence of miR-21 overexpression in prostate epithelial cells was an increase in proliferative ability which paralleled an inhibition of BTG2 expression. However, miR21 targets genes with apoptotic and regulatory functions such as PDCD4 and PTEN (Example 2, Ref 8-11) which could contribute to the phenotype of miR-21-overexpressing prostate cells. To define the role of miR-21-mediated BTG2 silencing we engineered a lentiviral vector, which acts as a decoy by specifically releasing miR-21 repression of BTG2 (i.e. "de-repressing" BTG2 expression). In this way, we could study the effect of restoring endogenous BTG2 expression rather than expressing exogenous BTG2 in prostate cells. This experimental system recapitulates more closely a situation in which BTG2 could be restored through the use of therapeutic tools and provides indications on the efficacy of such strategy in vivo. In fact, we found that cells in which BTG2 expression has been derepressed through the use of the UTR-BTG2 vector reverted to a less aggressive phenotype, as shown by reduced growth rates in vitro and decreased aggressiveness in vivo.

BTG2 has been previously shown to exert its tumor suppressor activity by linking the p53 and the Rb pathways through a control circuit that is lost during neoplastic transformation (Boiko 2006). This mechanism seems to be implicated also in prostate tumorigenesis, as shown by the down-regulation of cyclin D1 and pRb that resulted from BTG2 derepression. Interestingly, cyclin D1 and pRb levels in BTG2-derepressed prostate cancer cells returned more similar to those found in non-transformed prostate epithelial cells. Altogether, these observations suggest that BTG2 lies at a central point in the control of prostate tumorigenesis as it links Ras, p53 and Rb pathways resulting in final control of cell growth.

Inhibition of miR-21 action on BTG2 in vivo by the UTR-BTG2 vector results in decrease of tumor aggressiveness, which is apparently due to the formation of apoptotic areas within the tumor mass. This observation is in accordance with recent observations by Lim et al. that BTG2 enhances the susceptibility of neoplastic cells to apoptosis, suggesting that the proapoptotic action of BTG2 may contribute to its role as a tumor suppressor.

In conclusion, we have shown (for the first time) that miR-21 promotes prostate tumorigenesis by post-transcriptionally targeting BTG2 thus increasing prostate cell proliferation and survival. Use of the above described vector system reduced tumor growth in vivo by interfering with this regulatory loop (by specifically abrogating miR-21 action on BTG2 transcripts). These vectors, therefore allowed us to demonstrate that modulation of the miR-21/BTG2 axis may have therapeutic relevance for prostate cancer treatment. The use of this vector system is also widely applicable for other miRs and 3'UTRs of genes to be investigated.

The previously described decoy vectors repress the total amount of microRNA, whereas the 3'UTR-mediated vectors sequester only some of the target microRNA and derepresses the protein of interest. The TW3'UTR vector is similar to that described in Example 1.

The TW3'UTR vector was obtained by modifying the EGFP 3'UTR of the TWEEN vector through the insertion of a multicloning site (XhoI-XbaI) that allowed the subcloning of the sequences of interest. Then the EGFP modified 3'UTR cassette was inserted under the CMV promoter control. Moreover, a puromycin resistance gene was inserted under the PGK promoter control to allow the selection of transduced cells (as before). To generate the TW3'UTRBTG2 vector, about 400 bp of 3'BTG-2UTR, containing mir-21 binding site, was subcloned into XhoI-XbaI multicloning site in TW3'UTR vector.

This design was intended to optimize repression of the transgene in the presence of miR21 and simultaneously derepress endogenous BTG-2 mRNA. TW3'UTRBTG2 vector generates an artificial transcript (chimera) composed of EGFP 3'modified UTR containing a fragment of BTG-2 3'UTR. The chimera transcripts quantitatively compete with endogenous BTG2 for mir-21 biding (and therefore repression). The repression of other genes repressed by mir2l is not significantly affected, see FIG. 17b, f), where derepression of BTG-2 protein translation was not shown in the other mir-21 target genes such as PTEN, p63 and sprouty2.

BTG-2 upregulation can be detected by cytofluorimetric assays. Western blotting revealed signal cascade activation after BTG-2 overstimulation. BTG-2 induces inhibition of proliferation, Cyclin D1 repression, and a reduction in Rb phosphorylation.

This kind of vector can be used to derepress only the gene of interest and not other targets of the same miRs. This is of great interest in the miRNA field because miRNAs have many targets and their function can vary with cell type. For the first time, we demonstrated that it is possible derepress only a target gene, maintaining the same levels for the others.

Not all miRNA can be classified as tumor suppressors or oncomirs. More importantly, miRNAs can differentiate their role between tissues and pathologies. Since miRNA could have multiple targets, groups of then can be useful for tumor regression, but other subgroups may actually promote cancer progression.

References For Example 2

1—Rouault, J.-P., Falette, N., Guehenneux, F., Guillot, C., Rimokh, R., Wang, Q., Berthet, C., Moyret-Lalle, C., Savatier, P., Pain, B., Shaw, P., Berger, R., Samarut, J., Magaud, J.-P., Ozturk, M., Samarut, C. and Puisieux, A. (1996) Identification of BTG2, an antiproliferative p53-dependent component of the DNA damage cellular response pathway. Nature Genet. 14, 482-486.

2—Cortes, U., Moyret-Lalle, C., Falette, N., Duriez, C., Ghissassi, F. E., Barnas, C., Morel, A. P., Hainaut, P., Magaud, J. P. and Puisieux, A. (2000) BTG gene expression in the p53-dependent and -independent cellular response to DNA damage. Mol. Carcinog. 27, 57-64

3—Bradbury, A., Possenti, R., Shooter, E. M. and Tirone, F. (1991) Molecular cloning of PC3, a putatively secreted protein whose mRNA is induced by nerve growth factor and depolarization. Proc. Natl Acad. Sci. USA 88, 3353-3357.

4—Fletcher, B. S., Lim, R. W., Varnum, B. C., Kujubu, D. A., Koski, R. A. and Herschman, H. R. (1991) Structure and expression of TIS21, a primary response gene induced by growth factors and tumor promoters. J. Biol. Chem. 266, 14511-14518.

5—Cmarik, J. L., Herschman, H. and Colburn, N. H. (1994) Preferential primary-response gene expression in promotion-resistant versus promotion-sensitive JB6 cells. Mol. Carcinog. 11, 115-124.

6—Farioli-Vecchioli S, Tanori M, Micheli L, Mancuso M, Leonardi L, Saran A, Ciotti M T, Ferretti E, Gulino A, Pazzaglia S, Tirone. (2007 July) Inhibition of medulloblastoma tumorigenesis by the antiproliferative and pro-differentiative gene PC3. F.FASEB J.; 21(9):2215-25. Epub Mar. 19, 2007

7—Ficazzola, M A, Fraiman M, Gitlin J, Woo K, Melamed J, Rubin M A, Walden P D. (2001 August) Antiproliferative B cell translocation gene 2 protein is down-regulated post-transcriptionally as an early event in prostate carcinogenesis. Carcinogenesis. 22(8): 1271-9.

8—Gabriely G, Wurdinger T, Kesari S, Esau C C, Burchard J, Linsley P S, Krichevsky A M. (Jun. 30, 2008) MiR-21 Promotes Glioma Invasion by Targeting MMP Regulators. Mol Cell Biol. 28(17): 5369-80.

9—Dillhoff M, Liu J, Frankel W, Croce C, Bloomston M. (Jul. 19, 2008) MicroRNA-21 is Overexpressed in Pancreatic Cancer and a Potential Predictor of Survival. J Gastrointest Surg. 12(12): 2171-6.

10—Singh S K, Kagalwala M N, Parker-Thornburg J, Adams H, Majumder S. (May 8, 2008) REST maintains self-renewal and pluripotency of embryonic stem cells. Nature 453(7192):223-7.

11—Inhibitory effects of anti-miRNA oligonucleotides (AMOs) on A549 cell growth. Fei J, Lan F, Guo M, Li Y, Liu Y. (2008 November) J Drug Target 16(9):688-93.

12—Lee, Daniel Y et al: PLOS One February 2009 Vol 4 Issue 2.

The invention claimed is:

1. A method of diagnosing metastatic status of a cancerous prostate tissue or cancerous prostate tumor, said method comprising:
   detecting levels of expression of miR 15a and miR 16-1 in one or more cells from the cancerous prostate tissue or cancerous prostate tumor,
   wherein miR 15a has the sequence set forth in SEQ ID NO:4 and miR 16-1 has the sequence set forth in SEQ ID NO:5, and wherein the detecting step comprises performing Northern hybridization or in situ hybridization, using at least one miR 15a specific probe comprising sequence specific for SEQ ID NO:4 and at least one miR 16-1 specific probe comprising sequence specific for SEQ ID NO:5;
   whereby prostate cancer metastasis is diagnosed when detected levels of miR 15a and miR 16-1 are down-regulated in the cells from the cancerous prostate tissue or cancerous prostate tumor as compared to normal prostate cells, primary prostate tumor cells or benign prostate tissue; and
   wherein the at least one miR 15a specific probe and the at least one miR16-1 specific probe are each 100% specific for the seed sequence AGCAGCA.

2. A method of diagnosing metastatic status of a cancerous prostate tissue or prostate tumor and treating cancerous prostate tissue or prostate tumor, said method comprising the steps of:
   (a) detecting levels of expression of miR 15 and miR 16 in one or more cells from the cancerous prostate tissue or prostate tumor, whereby prostate cancer metastasis is diagnosed when miR 15 and miR 16 are down-regulated in cancerous prostate tumor cells or tissue as compared to normal cells, primary tumor cells or tissue or benign prostate tissue;
   wherein the miR 15 is miR 15a and wherein the miR 16 is miR 16-1;
   wherein the detecting step comprises:
      (i) performing quantitative real-time polymerase chain reaction, using at least one miR 15a specific primer comprising sequence specific for SEQ ID NO:4 and at least one miR 16-1 specific primer comprising sequence specific for SEQ ID NO:5; or
      (ii) performing Northern hybridization or in situ hybridization, using at least one miR 15a specific probe comprising sequence specific for SEQ ID NO:4 and at least one miR 16-1 specific probe comprising sequence specific for SEQ ID NO:5; and
   (b) administering antisense RNA to a patient in need thereof or causing antisense RNA to be expressed in a patient in need thereof, wherein the antisense RNA is complementary to all or part of the 3'untranslated region (UTR) of Cyclin D1, Wnt3a, and/or bFGF protein mRNA;
thereby diagnosing the metastatic status and treating the cancerous prostate tissue or prostate tumor.

3. The method of claim 2, wherein the antisense RNA is miR 15 or miR 16.

4. The method of claim 2, wherein the antisense RNA is miR 15a or miR 16-1.

5. The method of claim 2, wherein the antisense RNA comprises the seed sequence AGCAGCA.

6. The method of claim 2, wherein the antisense RNA has the sequence of SEQ ID NO:4 or SEQ ID NO:5.

7. The method of claim 2, further comprising the step of:
   (c) administering to the patient in need thereof a treatment regimen of surgery including at least partial removal of cancerous tissue, chemotherapy, hormone treatment, and/or radiation treatment.

8. The method of claim 7, wherein the hormone treatment comprises androgen ablation.

* * * * *

SEQUENCE LISTING

```
<160> NUMBER OF SEQ ID NOS: 33

<210> SEQ ID NO 1
<211> LENGTH: 3665
<212> TYPE: DNA
<213> ORGANISM: Homo sapiens

<400> SEQUENCE: 1
ggcttggggc agccgggtag ctcggaggtc gtggcgctgg gggctagcac cagcgctctg      60
tcgggaggcg cagcggttag gtggaccggt cagcggactc accggccagg gcgctcggtg     120
ctggaatttg atattcattg atccgggttt tatccctctt cttttttctt aaacattttt     180
ttttaaaact gtattgtttc tcgttttaat ttattttttgc ttgccattcc ccacttgaat     240
cgggccgacg gcttggggag attgctctac ttccccaaat cactgtggat tttggaaacc     300
agcagaaaga ggaaagaggt agcaagagct ccagagagaa gtcgaggaag agagacgg      360 ggtcagagag agcgcgcggg cgtgcgagca gcgaaagcga caggggcaaa gtgagtgacc     420
tgcttttggg ggtgaccgcc ggagcgcggc gtgagccctc cccttggga tcccgcagct      480 gaccagtcgc gctgacggac agacagacag acaccgcccc cagcccagc taccacctcc      540 tcccggccg gcggcggaca gtggacgcgg cggcgagccg cgggcagggg ccggagcccg      600
cgcccggagg cggggtggag ggggtcgggg ctcgcggcgt cgcactgaaa cttttcgtcc      660
aacttctggg ctgttctcgc ttcggaggag ccgtggtccg cgcggggaa gccgagccga      720 gcggagccgc gagaagtgct agctcgggcc gggaggagcc gcagccggag gaggggagg      780 aggaagaaga gaaggaagag gagaggggc cgcagtggcg actcggcgct cggaagccgg      840
gctcatggac gggtgaggcg gcggtgtgcg cagacagtgc tccagccgcg cgcgctcccc      900
aggccctggc ccgggcctcg ggccggggag gaagagtagc tcgccgaggc gccgaggaga      960
gcgggccgcc ccacagcccg agccggagag ggagcgcgag ccgcgccggc cccggtcggg     1020
cctccgaaac catgaacttt ctgctgtctt gggtgcattg gagccttgcc ttgctgctct     1080
acctccacca tgccaagtgg tcccaggctg cacccatggc agaaggagga gggcagaatc     1140
atcacgaagt ggtgaagttc atggatgtct atcagcgcag ctactgccat ccaatcgaga     1200
ccctggtgga catcttccag gagtaccctg atgagatcga gtacatcttc aagccatcct     1260
gtgtgcccct gatgcgatgc ggggctgct gcaatgacga gggcctggag tgtgtgccca     1320
ctgaggagtc caacatcacc atgcagatta tgcggatcaa acctcaccaa ggccagcaca     1380
taggagagat gagcttccta cagcacaaca aatgtgaatg cagaccaaag aaagatagag     1440
```

-continued

```
caagacaaga aaaaaatca gttcgaggaa agggaagggg gcaaaaacga aagcgcaaga      1500
aatcccggta taagtcctgg agcgtgtacg ttggtgcccg ctgctgtcta atgccctgga      1560
gcctccctgg cccccatccc tgtgggcctt gctcagagcg gagaaagcat ttgtttgtac      1620
aagatccgca gacgtgtaaa tgttcctgca aaaacacaga ctcgcgttgc aaggcgaggc      1680
agcttgagtt aaacgaacgt acttgcagat gtgacaagcc gaggcggtga gccgggcagg      1740
aggaaggagc ctccctcagg gtttcgggaa ccagatctct caccaggaaa gactgataca      1800
gaacgatcga tacagaaacc acgctgccgc caccacacca tcaccatcga cagaacagtc      1860
cttaatccag aaacctgaaa tgaaggaaga ggagactctg cgcagagcac tttgggtccg      1920
gagggcgaga ctccggcgga agcattcccg ggcgggtgac ccagcacggt ccctcttgga      1980
attggattcg ccattttatt tttcttgctg ctaaatcacc gagcccggaa gattagagag      2040
ttttatttct gggattcctg tagacacacc cacccacata catacattta tatatatata      2100
tattatatat atataaaaat aaatatctct attttatata tataaaatat atatattctt      2160
tttttaaatt aacagtgcta atgttattgg tgtcttcact ggatgtattt gactgctgtg      2220
gacttgagtt gggaggggaa tgttcccact cagatcctga cagggaagag gaggagatga      2280
gagactctgg catgatcttt tttttgtccc acttggtggg gccagggtcc tctcccctgc      2340
ccaggaatgt gcaaggccag ggcatggggg caaatatgac ccagttttgg gaacaccgac      2400
aaacccagcc ctggcgctga gcctctctac cccaggtcag acggacagaa agacagatca      2460
caggtacagg gatgaggaca ccggctctga ccaggagttt ggggagcttc aggacattgc      2520
tgtgctttgg ggattccctc cacatgctgc acgcgcatct cgcccccagg ggcactgcct      2580
ggaagattca ggagcctggg cggccttcgc ttactctcac ctgcttctga gttgcccagg      2640
agaccactgg cagatgtccc ggcgaagaga agagacacat tgttggaaga agcagcccat      2700
gacagctccc cttcctggga ctcgccctca tcctcttcct gctccccttc ctggggtgca      2760
gcctaaaagg acctatgtcc tcacaccatt gaaaccacta gttctgtccc cccaggagac      2820
ctggttgtgt gtgtgtgagt ggttgacctt cctccatccc ctggtccttc ccttcccttc      2880
ccgaggcaca gagagacagg gcaggatcca cgtgcccatt gtggaggcag agaaaagaga      2940
aagtgtttta tatacggtac ttatttaata tcccttttta attagaaatt aaaacagtta      3000
atttaattaa agagtagggt tttttttcag tattcttggt taatatttaa tttcaactat      3060
ttatgagatg tatcttttgc tctctcttgc tctcttattt gtaccggttt ttgtatataa      3120
aattcatgtt tccaatctct ctctccctga tcggtgacag tcactagctt atcttgaaca      3180
gatatttaat tttgctaaca ctcagctctg ccctccccga tcccctggct ccccagcaca      3240
cattcctttg aaataaggtt tcaatataca tctacatact atatatatat ttggcaactt      3300
gtatttgtgt gtatatatat atatatatgt ttatgtatat atgtgattct gataaaatag      3360
acattgctat tctgttttt atatgtaaaa acaaaacaag aaaaaataga gaattctaca      3420
tactaaatct ctctccttt ttaatttaa tatttgttat catttattta ttggtgctac      3480
tgtttatccg taataattgt ggggaaaaga tattaacatc acgtctttgt ctctagtgca      3540
gttttcgag atattccgta gtacatattt attttaaac aacgacaaag aaatacagat      3600
atatcttaaa aaaaaaaag cattttgtat taagaatt aattctgatc tcaaaaaaaa      3660
aaaaa                                                                  3665
```

<210> SEQ ID NO 2
<211> LENGTH: 4150

<212> TYPE: DNA
<213> ORGANISM: Homo sapiens

<400> SEQUENCE: 2

| | | | | | |
|---|---|---|---|---|---|
| cttgaatctt | ggggcaggaa | ctcagaaaac | ttccagcccg | ggcagcgcgc | gcttggtgca | 60 |
| agactcagga | gctagcagcc | cgtcccctc | cgactctccg | gtgccgccgc | tgcctgctcc | 120 |
| cgccaccta | ggaggcgcgg | tgccaccac | tactctgtcc | tctgcctgtg | ctccgtgccc | 180 |
| gaccctatcc | cggcggagtc | tccccatcct | cctttgcttt | ccgactgccc | aaggcacttt | 240 |
| caatctcaat | ctcttctctc | tctctctctc | tctctctctc | tctctctctc | tctctctctc | 300 |
| tctctctctc | gcagggtggg | gggaagagga | ggaggaattc | tttccccgcc | taacatttca | 360 |
| agggacacaa | ttcactccaa | gtctcttccc | tttccaagcc | gcttccgaag | tgctcccggt | 420 |
| gcccgcaact | cctgatccca | acccgcgaga | ggagcctctg | cgacctcaaa | gcctctcttc | 480 |
| cttctccctc | gcttccctcc | tcctcttgct | acctccacct | ccaccgccac | ctccacctcc | 540 |
| ggcacccacc | caccgccgcc | gccgccaccg | gcagcgcctc | ctcctctcct | cctcctcctc | 600 |
| ccctcttctc | tttttggcag | ccgctggacg | tccggtgttg | atggtggcag | cggcggcagc | 660 |
| ctaagcaaca | gcagccctcg | cagcccgcca | gctcgcgctc | gccccgccgg | cgtccccagc | 720 |
| cctatcacct | catctcccga | aaggtgctgg | gcagctccgg | ggcggtcgag | gcgaagcggc | 780 |
| tgcagcggcg | gtagcggcgg | cgggaggcag | gatgagcgca | cgcggtgagg | gcgcggggca | 840 |
| gccgtccact | tcagcccagg | gacaacctgc | cgccccagcg | cctcagaaga | gaggacgcgg | 900 |
| ccgccccagg | aagcagcagc | aagaaccaac | cggtgagccc | tctcctaaga | gacccagggg | 960 |
| aagacccaaa | ggcagcaaaa | acaagagtcc | ctctaaagca | gctcaaaaga | aagcagaagc | 1020 |
| cactggagaa | aaacgccaa | gaggcagacc | taggaaatgg | ccacaacaag | ttgttcagaa | 1080 |
| gaagcctgct | caggaggaaa | ctgaagagac | atcctcacaa | gagtctgccg | aagaggacta | 1140 |
| gggggcgcca | acgttcgatt | tctacctcag | cagcagttgg | atcttttgaa | gggagaagac | 1200 |
| actgcagtga | ccacttattc | tgtattgcca | tggtctttcc | actttcatct | ggggtggggt | 1260 |
| ggggtgggt | gggggagggg | ggggtggggt | gggagaaat | cacataaccct | taaaaaggac | 1320 |
| tatattaatc | accttctttg | taatcccttc | acagtcccag | gtttagtgaa | aaactgctgt | 1380 |
| aaacacaggg | gacacagctt | aacaatgcaa | cttttaatta | ctgttttctt | ttttcttaac | 1440 |
| ctactaatag | tttgttgatc | tgataagcaa | gagtgggcgg | gtgagaaaaa | ccgaattggg | 1500 |
| tttagtcaat | cactgcactg | catgcaaaca | agaaacgtgt | cacacttgtg | acgtcgggca | 1560 |
| ttcatatagg | aagaacgcgg | tgtgtaacac | tgtgtacacc | tcaaatacca | ccccaaccca | 1620 |
| ctccctgtag | tgaatcctct | gtttagaaca | ccaaagataa | ggactagata | ctactttctc | 1680 |
| ttttcgtat | aatcttgtag | acacttactt | gatgattttt | aacttttat | ttctaaatga | 1740 |
| gacgaaatgc | tgatgtatcc | tttcattcag | ctaacaaact | agaaaaggtt | atgttcattt | 1800 |
| ttcaaaaagg | gaagtaagca | aacaaatatt | gccaactctt | ctatttatgg | atatcacaca | 1860 |
| tatcagcagg | agtaataaat | ttactcacag | cacttgtttt | caggacaaca | cttcattttc | 1920 |
| aggaaatcta | cttcctacag | agccaaaatg | ccatttagca | ataaataaca | cttgtcagcc | 1980 |
| tcagagcatt | taaggaaact | agacaagtaa | aattatcctc | tttgtaattt | aatgaaaagg | 2040 |
| tacaacagaa | taatgcatga | tgaactcacc | taattatgag | gtgggaggag | cgaaatctaa | 2100 |
| atttcttttg | ctatagttat | acatcaattt | aaaaagcaaa | aaaaaaaaag | gggggggcaa | 2160 |
| tctctctctg | tgtctttctc | tctctctctt | cctctccctc | tctcttttca | ttgtgtatca | 2220 |

| | | | | |
|---|---|---|---|---|
| gtttccatga | aagacctgaa | taccacttac | ctcaaattaa | gcatatgtgt | tacttcaagt | 2280 |
| aatacgtttt | gacataagat | ggttgaccaa | ggtgcttttc | ttcggcttga | gttcaccatc | 2340 |
| tcttcattca | aactgcactt | ttagccagag | atgcaatata | tccccactac | tcaatactac | 2400 |
| ctctgaatgt | tacaacgaat | ttacagtcta | gtacttatta | catgctgcta | tacacaagca | 2460 |
| atgcaagaaa | aaaacttact | gggtaggtga | ttctaatcat | ctgcagttct | ttttgtacac | 2520 |
| ttaattacag | ttaaagaagc | aatctcctta | ctgtgtttca | gcatgactat | gtatttttct | 2580 |
| atgttttttt | aattaaaaat | ttttaaaata | cttgtttcag | cttctctgct | agatttctac | 2640 |
| attaacttga | aaatttttta | accaagtcgc | tcctaggttc | ttaaggataa | ttttcctcaa | 2700 |
| tcacactaca | catcacacaa | gatttgactg | taatatttaa | atattaccct | ccaagtctgt | 2760 |
| acctcaaatg | aattctttaa | ggagatggac | taattgactt | gcaaagacct | acctccagac | 2820 |
| ttcaaaagga | atgaacttgt | tacttgcagc | attcatttgt | tttttcaatg | tttgaaatag | 2880 |
| ttcaaactgc | agctaaccct | agtcaaaact | attttttgtaa | aagacatttg | atagaaagga | 2940 |
| acacgttttt | acatactttt | gcaaaataag | taaataataa | ataaaataaa | agccaacctt | 3000 |
| caaagaaact | tgaagctttg | taggtgagat | gcaacaagcc | ctgcttttgc | ataatgcaat | 3060 |
| caaaaatatg | tgtttttaag | attagttgaa | tataagaaaa | tgcttgacaa | atattttcat | 3120 |
| gtattttaca | caaatgtgat | ttttgtaata | tgtctcaacc | agatttattt | taaacgcttc | 3180 |
| ttatgtagag | tttttatgcc | tttctctcct | agtgagtgtg | ctgacttttt | aacatggtat | 3240 |
| tatcaactgg | gccaggaggt | agtttctcat | gacggctttt | gtcagtatgg | cttttagtac | 3300 |
| tgaagccaaa | tgaaactcaa | aaccatctct | cttccagctg | cttcagggag | gtagtttcaa | 3360 |
| aggccacata | cctctctgag | actggcagat | cgctcactgt | tgtgaatcac | caaggagct | 3420 |
| atggagagaa | ttaaaactca | acattactgt | taactgtgcg | ttaaataagc | aaataaacag | 3480 |
| tggctcataa | aaataaaagt | cgcattccat | atctttggat | gggccttttta | gaaacctcat | 3540 |
| tggccagctc | ataaaatgga | agcaattgct | catgttggcc | aaacatggtg | caccgagtga | 3600 |
| tttccatctc | tggtaaagtt | acacttttat | ttcctgtatg | ttgtacaatc | aaaacacact | 3660 |
| actacctctt | aagtcccagt | atacctcatt | tttcatactg | aaaaaaaaag | cttgtggcca | 3720 |
| atggaacagt | aagaacatca | taaaattttt | atatatatag | tttatttttg | tgggagataa | 3780 |
| attttatagg | actgttcttt | gctgttgttg | gtcgcagcta | cataagactg | gacatttaac | 3840 |
| ttttctacca | tttctgcaag | ttaggtatgt | ttgcaggaga | aaagtatcaa | gacgtttaac | 3900 |
| tgcagttgac | tttctccctg | ttcctttgag | tgtcttctaa | ctttattctt | tgttctttat | 3960 |
| gtagaattgc | tgtctatgat | tgtactttga | atcgcttgct | tgttgaaaat | atttctctag | 4020 |
| tgtattatca | ctgtctgttc | tgcacaataa | acataacagc | ctctgtgatc | cccatgtgtt | 4080 |
| ttgattcctg | ctctttgtta | cagttccatt | aaatgagtaa | taaagtttgg | tcaaaacaga | 4140 |
| aaaaaaaaa | | | | | | 4150 |

<210> SEQ ID NO 3
<211> LENGTH: 2031
<212> TYPE: DNA
<213> ORGANISM: Homo sapiens

<400> SEQUENCE: 3

| | | | | |
|---|---|---|---|---|
| catttgcatg | gccccgcccc | ctgagtgaca | cggctggcgc | gggcgggccc | gtcccccctg | 60 |
| cccctgggtc | gctcttttta | agctcccctg | agccggtgct | gcgctcctct | aattgggact | 120 |
| ccgagccggg | gctatttctg | gcgctggcgc | ggctccaaga | aggcatccgc | atttgctacc | 180 |

-continued

```
agcggcggcc gcggcggagc caggccggtc ctcagcgccc agcaccgccg ctcccggcaa    240
cccggagcgc gcaccgcagg ccggcggccg agctcgcgca tcccagccat cactcttcca    300
cctgctcctt agagaaggga agatgagtga gtcgagctcg aagtccagcc agcccttggc    360
ctccaagcag gaaaaggacg gcactgagaa gcggggccgg ggcaggccgc gcaagcagcc    420
tccggtgagt cccgggacag cgctggtagg gagtcagaag gagcccagcg aagtgccaac    480
acctaagaga cctcggggcc gaccaaaggg aagcaaaaac aagggtgctg ccaagacccg    540
gaaaaccacc acaactccag gaaggaaacc aaggggcaga cccaaaaaac tggagaagga    600
ggaagaggag ggcatctcgc aggagtcctc ggaggaggag cagtgaccca tgcgtgccgc    660
ctgctcctca ctggaggagc agcttccttc tgggactgga cagctttgct ccgctcccac    720
cgcccccacc ccttcccag gcccaccatc accaccgcct ctggccgcca ccccatctt    780 ccacctgtgc cctcaccacc acactacaca gcacaccagc cgctgcaggg ctcccatggg    840
ctgagtgggg agcagttttc ccctggcctc agttcccagc tcccccgcc cacccacgca    900 tacacacatg ccctcctgga caaggctaac atcccactta gccgcaccct gcacctgctg    960
cgtccccact cccttggtgg tggggacatt gctctctggg cttttggttt ggggcgccc   1020 tctctgctcc ttcactgttc cctctggctt cccatagtgg ggcctgggag ggttcccctg   1080
gccttaaaag gggcccaagc cccatctcat cctggcacgc cctactccac tgccctggca   1140
gcagcaggtg tggccaatgg agggggtgc tggccccag gattccccca gccaaactgt   1200 cttttgtcacc acgtggggct cacttttcat ccttccccaa cttccctagt ccccgtacta   1260
ggttggacag ccccttcgg ttacaggaag gcaggagggg tgagtcccct actccctctt   1320
cactgtggcc acagccccct tgccctccgc ctgggatctg agtacatatt gtggtgatgg   1380
agatgcagtc acttattgtc caggtgaggc ccaagagccc tgtggccgcc acctgaggtg   1440
ggctggggct gctcccctaa ccctactttg cttccgccac tcagccattt ccccctcctc   1500
agatggggca ccaataacaa ggagctcacc ctgcccgctc caaccccc tcctgctcct   1560 ccctgccccc caaggttctg gttccatttt tcctctgttc acaaactacc tctggacagt   1620
tgtgttgttt tttgttcaat gttccattct tcgacatccg tcattgctgc tgctaccagc   1680
gccaaatgtt catcctcatt gcctcctgtt ctgcccacga tcccctcccc caagatactc   1740
tttgtgggga agaggggctg gggcatggca ggctgggtga ccgactaccc cagtcccagg   1800
gaaggtgggg ccctgcccct aggatgctgc agcagagtga gcaaggggc ccaaatcgac   1860 cataaagggt gtaggggcca cctcctcccc ctgttctgtt ggggaggggt agccatgatt   1920
tgtcccagcc tggggctccc tctctggttt cctatttgca gttacttgaa taaaaaaat   1980 atccttttct ggaaaaaaaa aaaaaaaaa aaaaaaaaa aaaaaaaaa a              2031
```

<210> SEQ ID NO 4
<211> LENGTH: 22
<212> TYPE: RNA
<213> ORGANISM: Homo sapiens

<400> SEQUENCE: 4
uagcagcaca uaaugguuug ug                                              22

<210> SEQ ID NO 5
<211> LENGTH: 22
<212> TYPE: RNA
<213> ORGANISM: Homo sapiens

-continued

```
<400> SEQUENCE: 5
uagcagcacg uaaauauugg cg                                                   22

<210> SEQ ID NO 6
<211> LENGTH: 22
<212> TYPE: DNA
<213> ORGANISM: artificial
<220> FEATURE:
<223> OTHER INFORMATION: anti-miR-15

<400> SEQUENCE: 6
cacaaaccat tatgtgctgc ta                                                   22

<210> SEQ ID NO 7
<211> LENGTH: 22
<212> TYPE: DNA
<213> ORGANISM: artificial
<220> FEATURE:
<223> OTHER INFORMATION: anti-miR-16

<400> SEQUENCE: 7
cgccaatatt tacgtgctgc ta                                                   22

<210> SEQ ID NO 8
<211> LENGTH: 23
<212> TYPE: RNA
<213> ORGANISM: Homo sapiens

<400> SEQUENCE: 8
guaguaguau guuuguaagc uau                                                  23

<210> SEQ ID NO 9
<211> LENGTH: 4304
<212> TYPE: DNA
<213> ORGANISM: Homo sapiens

<400> SEQUENCE: 9
cacacggact acaggggagt tttgttgaag ttgcaaagtc ctggagcctc cagagggctg          60
tcggcgcagt agcagcgagc agcagagtcc gcacgctccg gcgaggggca gaagagcgcg         120
agggagcgcg gggcagcaga agcgagagcc gagcgcggac ccagccagga cccacagccc         180
tccccagctg cccaggaaga gccccagcca tggaacacca gctcctgtgc tgcgaagtgg         240
aaaccatccg ccgcgcgtac cccgatgcca acctcctcaa cgaccgggtg ctgcgggcca         300
tgctgaaggc ggaggagacc tgcgcgccct cggtgtccta cttcaaatgt gtgcagaagg         360
aggtcctgcc gtccatgcgg aagatcgtcg ccacctggat gctggaggtc tgcgaggaac         420
agaagtgcga ggaggaggtc ttcccgctgg ccatgaacta cctggaccgc ttcctgtcgc         480
tggagcccgt gaaaaagagc cgcctgcagc tgctggggc cacttgcatg ttcgtggcct         540
ctaagatgaa ggagaccatc cccctgacgg ccgagaagct gtgcatctac accgacaact         600
ccatccggcc cgaggagctg ctgcaaatgg agctgctcct ggtgaacaag ctcaagtgga         660
acctggccgc aatgaccccg cacgatttca ttgaacactt cctctccaaa atgccagagg         720
cggaggagaa caaacagatc atccgcaaac acgcgcagac cttcgttgcc ctctgtgcca         780
cagatgtgaa gttcatttcc aatccgcct ccatggtggc agcggggagc gtggtggccg         840
cagtgcaagg cctgaacctg aggagcccca acaacttcct gtcctactac cgcctcacac         900
gcttcctctc cagagtgatc aagtgtgacc cggactgcct ccgggcctgc caggagcaga         960
tcgaagccct gctggagtca gcctgcgcc aggcccagca gaacatggac cccaaggccg        1020
```

```
ccgaggagga ggaagaggag gaggaggagg tggacctggc ttgcacaccc accgacgtgc    1080
gggacgtgga catctgaggg cgccaggcag gcgggcgcca ccgccacccg cagcgagggc    1140
ggagccggcc ccaggtgctc ccctgacagt ccctcctctc cggagcattt tgataccaga    1200
agggaaagct tcattctcct tgttgttggt tgttttttcc tttgctcttt ccccttcca    1260 tctctgactt aagcaaaaga aaagattac ccaaaaactg tctttaaaag agagagagag    1320
aaaaaaaaaa tagtatttgc ataaccctga gcggtggggg aggagggttg tgctacagat    1380
gatagaggat tttataccc aataatcaac tcgtttttat attaatgtac ttgtttctct    1440
gttgtaagaa taggcattaa cacaaaggag gcgtctcggg agaggattag gttccatcct    1500
ttacgtgttt aaaaaaagc ataaaaacat tttaaaaaca tagaaaaatt cagcaaacca    1560
tttttaaagt agaagagggt tttaggtaga aaaacatatt cttgtgcttt tcctgataaa    1620
gcacagctgt agtggggttc taggcatctc tgtactttgc ttgctcatat gcatgtagtc    1680
actttataag tcattgtatg ttattatatt ccgtaggtag atgtgtaacc tcttcacctt    1740
attcatggct gaagtcacct cttggttaca gtagcgtagc gtgcccgtgt gcatgtcctt    1800
tgcgcctgtg accaccaccc caacaaacca tccagtgaca aaccatccag tggaggtttg    1860
tcgggcacca gccagcgtag cagggtcggg aaaggccacc tgtcccactc ctacgatacg    1920
ctactataaa gagaagacga aatagtgaca taatatattc tattttata ctcttcctat    1980 ttttgtagtg acctgtttat gagatgctgg ttttctaccc aacggccctg cagccagctc    2040
acgtccaggt tcaacccaca gctacttggt tgtgttctt cttcatattc taaaaccatt    2100
ccatttccaa gcactttcag tccaataggt gtaggaaata gcgctgtttt tgttgtgtgt    2160
gcagggaggg cagttttcta atggaatggt ttgggaatat ccatgtactt gtttgcaagc    2220
aggactttga ggcaagtgtg ggccactgtg gtggcagtgg aggtggggtg tttgggaggc    2280
tgcgtgccag tcaagaagaa aaaggtttgc attctcacat tgccaggatg ataagttcct    2340 ttcctttttct ttaaagaagt tgaagtttag gaatcctttg gtgccaactg gtgtttgaaa    2400
gtagggacct cagaggttta cctagagaac aggtggtttt taagggttat cttagatgtt    2460
tcacaccgga aggttttaa acactaaaat atataattta tagttaaggc taaaaagtat    2520
atttattgca gaggatgttc ataaggccag tatgatttat aaatgcaatc tccccttgat    2580
ttaaacacac agatacacac acacacacac acacacacaa accttctgcc tttgatgtta    2640
cagatttaat acagtttatt tttaaagata gatcctttta taggtgagaa aaaaacaatc    2700
tggaagaaaa aaaccacaca aagacattga ttcagcctgt ttggcgtttc ccagagtcat    2760
ctgattggac aggcatgggt gcaaggaaaa ttagggtact caacctaagt tcggttccga    2820
tgaattctta tccctgccc cttcctttaa aaaacttagt gacaaaatag acaatttgca    2880
catcttggct atgtaattct tgtaatttt atttaggaag tgttgaaggg aggtggcaag    2940
agtgtggagg ctgacgtgtg agggaggaca ggcgggagga ggtgtgagga ggaggctccc    3000
gaggggaagg ggcggtgccc acaccgggga caggccgcag ctccattttc ttattgcgct    3060
gctaccgttg acttccaggc acggtttgga aatattcaca tcgcttctgt gtatctcttt    3120
cacattgttt gctgctattg gaggatcagt ttttttgttt acaatgtcat atactgccat    3180
gtactagttt tagttttctc ttagaacatt gtattacaga tgccttttt gtagttttt    3240 ttttttttat gtgatcaatt ttgacttaat gtgattactg ctctattcca aaaaggttgc    3300
tgtttcacaa tacctcatgc ttcacttagc catggtggac ccagcgggca ggttctgcct    3360
```

```
gctttggcgg gcagacacgc gggcgcgatc ccacacaggc tggcgggggc cggccccgag    3420
gccgcgtgcg tgagaaccgc gccggtgtcc ccagagacca ggctgtgtcc ctcttctctt    3480
ccctgcgcct gtgatgctgg gcacttcatc tgatcggggg cgtagcatca tagtagtttt    3540
tacagctgtg ttattctttg cgtgtagcta tggaagttgc ataattatta ttattattat    3600
tataacaagt gtgtcttacg tgccaccacg gcgttgtacc tgtaggactc tcattcggga    3660
tgattggaat agcttctgga atttgttcaa gttttgggta tgtttaatct gttatgtact    3720
agtgttctgt ttgttattgt tttgttaatt acaccataat gctaatttaa agagactcca    3780
aatctcaatg aagccagctc acagtgctgt gtgccccggt cacctagcaa gctgccgaac    3840
caaaagaatt tgcaccccgc tgcgggccca cgtggttggg gccctgccct ggcagggtca    3900
tcctgtgctc ggaggccatc tcgggcacag gcccaccccg ccccacccct ccagaacacg    3960
gctcacgctt acctcaacca tcctggctgc ggcgtctgtc tgaaccacgc ggggccttg     4020
agggacgctt tgtctgtcgt gatggggcaa gggcacaagt cctggatgtt gtgtgtatcg    4080
agaggccaaa ggctggtggc aagtgcacgg ggcacagcgg agtctgtcct gtgacgcgca    4140
agtctgaggg tctgggcggc gggcggctgg gtctgtgcat ttctggttgc accgcggcgc    4200
ttcccagcac caacatgtaa ccggcatgtt tccagcagaa gacaaaaaga caaacatgaa    4260
agtctagaaa taaaactggt aaacccccaa aaaaaaaaa aaaa                      4304

<210> SEQ ID NO 10
<211> LENGTH: 2932
<212> TYPE: DNA
<213> ORGANISM: Homo sapiens

<400> SEQUENCE: 10
agctcccagg gccggccccc cccggcgcgt cacgctctcg gggcggactc ccggccctcc     60
gcgccctctc gcgcggcgat ggccccactc ggatacttct tactcctctg cagcctgaag    120
caggctctgg gcagctaccc gatctggtgg tcgctggctg ttgggccaca gtattcctcc    180
ctgggctcgc agcccatcct gtgtgccagc atcccgggcc tggtcccaa gcagctccgc     240
ttctgcagga actacgtgga gatcatgccc agcgtggccg agggcatcaa gattggcatc    300
caggagtgcc agcaccagtt ccgcggccgc cggtggaact gcaccaccgt ccacgacagc    360
ctggccatct tcgggcccgt gctggacaaa gctaccaggg agtcggcctt tgtccacgcc    420
attgcctcag ccggtgtggc ctttgcagtg acacgctcat gtgcagaagg cacggccgcc    480
atctgtggct gcagcagccg ccaccagggc tcaccaggca agggctggaa gtggggtggc    540
tgtagcgagg acatcgagtt tggtgggatg tgtgtctcgg gagttcgccga cgcccgggag    600
aaccggccag atgcccgctc agccatgaac cgccacaaca cgaggctggg cgcgcaggcc    660
atcgccagcc acatgcacct caagtgcaag tgccacgggc tgtcgggcag ctgcgaggtg    720
aagacatgct ggtggtcgca acccgacttc cgcgccatcg tgacttcct caaggacaag    780
tacgacagcg cctcggagat ggtggtgagg aagcaccggg agtcccgcgg ctgggtggag    840
accctgcggc gcgctacac ctacttcaag gtgcccacgg agcgcgacct ggtctactac    900
gaggcctcgc ccaacttctg cgagcccaac cctgagacgg gctccttcgg cacgcgcgac    960
cgcacctgca acgtcagctc gcacggcatc gacggctgcg acctgctgtg ctgcggccgc    1020
ggccacaacg cgcgagcgga gcgcgccgg gagaagtgcc gctgcgtgtt ccactggtgc    1080
tgctacgtca gctgccagga gtgcacgcgc gtctacgacg tgcacacctg caagtaggca    1140
ccggccgcgg ctcccccctgg acggggcggg ccctgcctga gggtgggctt ttccctgggt    1200
```

```
ggagcaggac tcccacctaa acggggcagt actcctccct gggggcggga ctcctccctg    1260
ggggtggggc tcctacctgg gggcagaact cctacctgaa ggcagggctc ctccctggag    1320
ctagtgtctc ctctctggtg gctgggctgc tcctgaatga ggcggagctc caggatgggg    1380
aggggctctg cgttggcttc tccctgggga cggggctccc ctggacagag gcggggctac    1440
agattgggcg gggcttctct tgggtgggac agggcttctc ctgcggggc gaggcccctc     1500 ccagtaaggg cgtggctctg ggtggcggg gcactaggta ggcttctacc tgcaggcggg     1560
gctcctcctg aaggaggcgg ggctctagga tggggcacgg ctctgggta ggctgctccc     1620 tgagggcgga gcgcctcctt aggagtgggg ttttatggtg gatgaggctt cttcctggat    1680
ggggcagagc ttctcctgac cagggcaagg ccccttccac gggggctgtg ctctgggtg     1740 ggcgtggcct gcataggctc cttcctgtgg gtggggcttc tctgggacca ggctccaatg    1800
gggcggggct tctctccgcg ggtgggactc ttccctggga accgccctcc tgattaaggc    1860
gtggcttctg caggaatccc ggctccagag caggaaattc agcccaccag ccacctcatc    1920 cccaacccc tgtaaggttc catccacccc tgcgtcgagc tgggaaggtt ccatgaagcg     1980
agtcgggtcc ccaacccgtg cccctgggat ccgaggcccc ctctccaagc gcctggcttt    2040
ggaatgctcc aggcgcgccg acgcctgtgc caccccttcc tcagcctggg gtttgaccac    2100
ccacctgacc aggggccta cctgggggaaa gcctgaaggg cctcccagcc cccaaccccca   2160 agaccaagct tagtcctggg agaggacagg gacttcgcag aggcaagcga ccgaggccct    2220
cccaaagagg cccgccctgc ccgggctccc acaccgtcag gtactcctgc cagggaactg    2280
gcctgctgcg ccccaggccc cgcccgtctc tgctctgctc agctgcgccc ccttctttgc    2340
agctgcccag cccctcctcc ctgccctcgg gtctccccac ctgcactcca tccagctaca    2400
ggagagatag aagcctctcg tcccgtccct ccctttcctc cgcctgtcca cagcccctta    2460
agggaaaggt aggaagagag gtccagcccc ccaggctgcc cagagctgct ggtctcattt    2520
gggggcgttc gggaggtttg gggggcatca accccccgac tgtgctgctc gcgaaggtcc    2580
cacagccctg agatgggccg gcccccttcc tggcccctca tggcgggact ggagaaatgg    2640
tccgctttcc tggagccaat ggcccggccc ctcctgactc atccgcctgg cccgggaatg    2700
aatggggagg ccgctgaacc cacccggccc atatccctgg ttgcctcatg gccagcgccc    2760
ctcagcctct gccactgtga accggctccc accctcaagg tgcggggaga agaagcggcc    2820
aggcggggcg ccccaagagc ccaaaagagg gcacaccgcc atcctctgcc tcaaattctg    2880 cgttttggt tttaatgtta tatctgatgc tgctatatcc actgtccaac gg             2932

<210> SEQ ID NO 11
<211> LENGTH: 6774
<212> TYPE: DNA
<213> ORGANISM: Homo sapiens

<400> SEQUENCE: 11
cggccccaga aaacccgagc gagtaggggg cggcgcgcag gagggaggag aactgggggc      60
gcgggaggct ggtgggtgtg gggggtggag atgtagaaga tgtgacgccg cggcccggcg    120
ggtgccagat tagcggacgc ggtgcccgcg gttgcaacgg gatcccgggc gctgcagctt    180
gggaggcggc tctccccagg cggcgtccgc ggagacaccc atccgtgaac cccaggtccc    240
gggccgccgg ctcgccgcgc accagggccc ggcggacaga gagcggccg agcggctcga    300 ggctggggga ccgcgggcgc ggccgcgcgc tgccgggcgg gaggctgggg ggccgggggcc   360
```

-continued

```
ggggccgtgc cccggagcgg gtcggaggcc ggggccgggg ccggggacg gcggctcccc    420
gcgcggctcc agcggctcgg ggatcccggc cgggccccgc agggaccatg gcagccggga    480
gcatcaccac gctgcccgcc ttgcccgagg atggcggcag cggcgccttc ccgcccggcc    540
acttcaagga ccccaagcgg ctgtactgca aaaacggggg cttcttcctg cgcatccacc    600
ccgacggccg agttgacggg gtccgggaga agagcgaccc tcacatcaag ctacaacttc    660
aagcagaaga gagaggagtt gtgtctatca aaggagtgtg tgctaaccgt tacctggcta    720
tgaaggaaga tggaagatta ctggcttcta aatgtgttac ggatgagtgt ttcttttttg    780
aacgattgga atctaataac tacaatactt accggtcaag gaaatacacc agttggtatg    840
tggcactgaa acgaactggg cagtataaac ttggatccaa acaggacct gggcagaaag    900
ctatactttt tcttccaatg tctgctaaga gctgatttta atggccacat ctaatctcat    960
ttcacatgaa agaagaagta tattttagaa atttgttaat gagagtaaaa gaaataaat   1020
gtgtatagct cagtttggat aattggtcaa acaattttt atccagtagt aaaatatgta   1080
accattgtcc cagtaaagaa aaataacaaa agttgtaaaa tgtatattct ccctttata   1140
ttgcatctgc tgttacccag tgaagcttac ctagagcaat gatcttttc acgcatttgc   1200
tttattcgaa aagaggcttt taaaatgtgc atgtttagaa acaaaatttc ttcatggaaa   1260
tcatatacat tagaaaatca cagtcagatg tttaatcaat ccaaaatgtc cactatttct   1320
tatgtcattc gttagtctac atgtttctaa acatataaat gtgaatttaa tcaattcctt   1380
tcatagtttt ataattctct ggcagttcct tatgatagag tttataaaac agtcctgtgt   1440
aaactgctgg aagttcttcc acagtcaggt caattttgtc aaacccttct ctgtacccat   1500
acagcagcag cctagcaact ctgctggtga tgggagttgt attttcagtc ttcgccaggt   1560
cattgagatc catccactca catcttaagc attcttcctg gcaaaaattt atggtgaatg   1620
aatatggctt taggcggcag atgatataca tatctgactt cccaaaagct ccaggatttg   1680
tgtgctgttg ccgaatactc aggacggacc tgaattctga ttttatacca gtctcttcaa   1740
aaacttctcg aaccgctgtg tctcctacgt aaaaaaagag atgtacaaat caataataat   1800
tacacttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatattttc ttaccactgt aaattcaaga agcttttgaa atgctgaata   1980
tttctttggc tgctacttgg aggcttatct acctgtacat ttttggggtc agctcttttt   2040
aacttcttgc tgctctttt cccaaaaggt aaaaatatag attgaaaagt taaaacattt   2100
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg atttttcaat taaatgcaaa   2280
tttgtgtggc aggattttta ttgccattaa catatttttg tggctgcttt ttctacacat   2340
ccagatggtc cctctaactg ggctttctct aatttgtga tgttctgtca ttgtctccca   2400
aagtatttag gagaagccct ttaaaaagct gccttcctct accactttgc tggaaagctt   2460
cacaattgtc acagacaaag attttgttc caatactcgt tttgcctcta ttttctgt   2520
ttgtcaaata gtaaatgata tttgcccttg cagtaattct actggtgaaa acatgcaaa   2580
gaagaggaag tcagaaaac atgtctcaat tcccatgtgc tgtgactgta gactgtctta   2640
ccatagactg tcttacccat cccctggata tgctcttgtt ttttcccctct aatagctatg   2700
gaaagatgca tagaaagagt ataatgtttt aaaacataag gcattcgtct gccattttc   2760
```

```
aattacatgc tgacttccct tacaattgag atttgcccat aggttaaaca tggttagaaa   2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaagtaa  ttttactct gatgtgcaat    3180 acatttgtta ttaaatttat tatttaagat ggtagcacta gtcttaaatt gtataaaata   3240
tcccctaaca tgtttaaatg tccattttta ttcattatgc tttgaaaaat aattatgggg   3300
aaatacatgt tgttattaa  atttattatt aaagatagta gcactagtct taaatttgat   3360
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg aagcaccgg  atggggtag  tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720
tgaaattttt aatcaagata gtgtgcttta ttctgttgta ttttttatta ttttaatata   3780
ctgtaagcca aactgaaata acatttgctg ttttataggt ttgaagaaca taggaaaaac   3840
taagaggttt tgttttatt  tttgctgatg aagagatatg tttaaatatg ttgtattgtt   3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgattttt    4140 aagaaggcag tttgtcaatt ttaatcttgt ggatacctt   atactcttag ggtattattt   4200
tatacaaaag ccttgaggat tgcattctat tttctatatg accctcttga tatttaaaaa   4260
acactatgga taacaattct tcatttacct agtattatga agaatgaag  gagttcaaac   4320 aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
ttagaaatgc cttcatatag acatagtctt tcagacctct actgtcagtt tcatttcta    4560 gctgctttca gggtttatg  aattttcagg caaagcttta atttatacta agcttaggaa   4620
gtatggctaa tgccaacggc agttttttc  ttcttaattc cacatgactg aggcatatat   4680
gatctctggg taggtgagtt gttgtgacaa ccacaagcac tttttttttt tttaaagaaa   4740
aaaaggtagt gaattttaa  tcatctggac tttaagaagg attctggagt atacttaggc   4800
ctgaaattat atatatttgg cttggaaatg tgttttctt  caattacatc tacaagtaag   4860
tacagctgaa attcagagga cccataagag ttcacatgaa aaaatcaat  ttatttgaaa   4920 aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
```

```
acaccactac aaaatcatct tttatatcaa cagaagaata agcataaact aagcaaaagg     5160
tcaataagta cctgaaacca agattggcta gagatatatc ttaatgcaat ccattttctg     5220
atggattgtt acgagttggc tatataatgt atgtatggta ttttgatttg tgtaaaagtt     5280
ttaaaaatca agctttaagt acatggacat ttttaaataa aatatttaaa gacaatttag     5340
aaaattgcct taatatcatt gttggctaaa tagaataggg gacatgcata ttaaggaaaa     5400
ggtcatggag aaataatatt ggtatcaaac aaatacattg atttgtcatg atacacattg     5460
aatttgatcc aatagtttaa ggaataggta ggaaaatttg gtttctattt tcgatttcc      5520 tgtaaatcag tgacataaat aattcttagc ttattttata tttccttgtc ttaaatactg     5580
agctcagtaa gttgtgttag gggattattt ctcagttgag actttcttat atgacatttt     5640
actatgtttt gacttcctga ctattaaaaa taaatagtag atacaatttt cataaagtga     5700
agaattatat aatcactgct ttataactga ctttattata tttatttcaa agttcattta     5760
aaggctacta ttcatcctct gtgatggaat ggtcaggaat tgttttctc atagtttaat      5820 tccaacaaca atattagtcg tatccaaaat aacctttaat gctaaacttt actgatgtat     5880
atccaaagct tctcattttc agacagatta atccagaagc agtcataaac agaagaatag     5940
gtggtatgtt cctaatgata ttatttctac taatggaata aactgtaata ttagaaatta     6000
tgctgctaat tatatcagct ctgaggtaat ttctgaaatg ttcagactca gtcggaacaa     6060
attggaaaat ttaaattttt attcttagct ataaagcaag aaagtaaaca cattaatttc     6120
ctcaacattt ttaagccaat taaaaatata aagatacac accaatatct tcttcaggct      6180
ctgacaggcc tcctggaaac ttccacatat ttttcaactg cagtataaag tcagaaaata     6240
aagttaacat aactttcact aacacacaca tatgtagatt tcacaaaatc cacctataat     6300
tggtcaaagt ggttgagaat atatttttta gtaattgcat gcaaaatttt tctagcttcc     6360
atcctttctc cctcgtttct tctttttttg ggggagctgg taactgatga aatcttttcc     6420 cacctttct cttcaggaaa tataagtggt tttgttggt taacgtgata cattctgtat       6480
gaatgaaaca ttggagggaa acatctactg aatttctgta atttaaaata ttttgctgct     6540
agttaactat gaacagatag aagaatctta cagatgctgc tataaataag tagaaaatat     6600
aaatttcatc actaaaatat gctatttta aatctatttc ctatattgta tttctaatca      6660
gatgtattac tcttattatt tctattgtat gtgttaatga tttatgtaa aaatgtaatt      6720 gcttttcatg agtagtatga ataaaattga ttagtttgtg ttttcttgtc tccc           6774
```

<210> SEQ ID NO 12
<211> LENGTH: 6492
<212> TYPE: DNA
<213> ORGANISM: Homo sapiens

<400> SEQUENCE: 12

```
tttctgtgaa gcagaagtct gggaatcgat ctggaaatcc tcctaatttt tactccctct       60
ccccgcgact cctgattcat tgggaagttt caaatcagct ataactggag agtgctgaag      120
attgatggga tcgttgcctt atgcatttgt tttggtttta caaaaggaa acttgacaga       180 ggatcatgct gtacttaaaa aatacaacat cacagaggaa gtagactgat attaacaata     240
cttactaata ataacgtgcc tcatgaaata aagatccgaa aggaattgga ataaaatttt     300
cctgcatctc atgccaaggg ggaaacacca gaatcaagtg ttccgcgtga ttgaagacac     360
cccctcgtcc aagaatgcaa agcacatcca ataaatagc tggattataa ctcctcttct      420
ttctctgggg gccgtggggt gggagctggg gcgagaggtg ccgttggccc ccgttgcttt     480
```

```
tcctctggga aggatggcgc acgctgggag aacagggtac gataaccggg agatagtgat    540
gaagtacatc cattataagc tgtcgcagag gggctacgag tgggatgcgg gagatgtggg    600
cgccgcgccc ccggggccg cccccgcacc gggcatcttc tcctcccagc ccgggcacac    660
gccccatcca gccgcatccc gggacccggt cgccaggacc tcgccgctgc agaccccggc    720 tgccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcgggacgc tttgccacgg tggtggagga    900
gctcttcagg gacggggtga actggggag gattgtggcc ttctttgagt cggtggggt    960 catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca caacaatt    1380 aacagtcttc aggcaaaacg tcgaatcagc tatttactgc caaagggaaa tatcatttat   1440 ttttacatt attaagaaaa aaagatttat ttatttaaga cagtcccatc aaaactcctg    1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtgggggggaa gtccatgcct ccctggcctg aagaagagac tctttgcata   1800
tgactcacat gatgcatacc tggtgggagg aaaagagttg gaacttcag atggacctag    1860 tacccactga gatttccacg ccgaaggaca gcgatgggaa aaatgccctt aaatcatagg   1920
aaagtatttt tttaagctac caattgtgcc gagaaaagca ttttagcaat ttatacaata   1980
tcatccagta ccttaagccc tgattgtgta tattcatata ttttggatac gcaccccca    2040 actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340 gtagagggt gtggctgggc ctgtcaccct ggggccctcc aggtaggccc gttttcacgt    2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
```

```
taaagaagta acaaaagaag tgacatcttc agcaaataaa ctaggaaatt tttttttctt    2880
ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaatacat gcatctcagc gttttttgt ttttaattgt     3060
atttagttat ggcctataca ctatttgtga gcaaaggtga tcgttttctg tttgagattt    3120
ttatctcttg attcttcaaa agcattctga aaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cgggggcttt ctcatggctg    3540
tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttcttttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata    4740
atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggatttttt ttttaaatta ttatgggaca aaggacattt    5220
```

```
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa ccttttggaa aatctgccgt    6000
gggccctcca gatagctcat ttcattaagt ttttccctcc aaggtagaat ttgcaagagt    6060
gacagtggat tgcatttctt ttggggaagc tttcttttgg tggttttgtt tattatacct    6120
tcttaagttt tcaaccaagg tttgcttttg ttttgagtta ctggggttat ttttgtttta    6180
aataaaaata agtgtacaat aagtgttttt gtattgaaag cttttgttat caagattttc    6240 atactttac cttccatggc tcttttttaag attgatactt ttaagaggtg gctgatattc    6300
tgcaacactg tacacataaa aaatacggta aggatacttt acatggttaa ggtaaagtaa    6360
gtctccagtt ggccaccatt agctataatg gcactttgtt tgtgttgttg gaaaaagtca    6420
cattgccatt aaactttcct tgtctgtcta gttaatattg tgaagaaaaa taaagtacag    6480
tgtgagatac tg                                                        6492

<210> SEQ ID NO 13
<211> LENGTH: 5911
<212> TYPE: DNA
<213> ORGANISM: Homo sapiens

<400> SEQUENCE: 13
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc aggggcgga ggcggaggag ggaccagcgc gggtggggagt gagagagcga     180 gccctcgcgc cccgccggcg catagcgctc ggagcgctct tgcggccaca ggcgcggcgt     240 cctcggcgg gggcggcagc tagcgggagc cgggacgccg gtgcagccgc agcgcgcgga     300
ggaacccggg tgtgccggga gctgggcggc cacgtccgga cgggaccgag accctcgta     360 gcgcattgcg gcgacctcgc cttccccggc cgcgagcgcg ccgctgcttg aaaagccgcg    420
gaacccaagg acttttctcc ggtccgagct cggggcgccc cgcagggcgc acggtacccg    480
tgctgcagtc gggcacgccg cggcgccggg gcctccgcag ggcgatggag cccggtctgc    540
aaggaaagtg aggcgccgcc gctgcgttct ggaggagggg ggcacaaggt ctggagaccc    600
cgggtggcgg acgggagccc tccccccgcc ccgcctccgg ggcaccagct ccggctccat    660
tgttcccgcc cggctggag gcgccgagca ccgagcgccc ccgggagtcg agcgccggcc    720
gcggagctct tgcgacccccg ccaggacccg aacagagccc gggggcggcg ggccggagcc    780
```

-continued

```
ggggacgcgg gcacacgccc gctcgcacaa gccacggcgg actctcccga ggcggaacct    840
ccacgccgag cgagggtcag tttgaaaagg aggatcgagc tcactgtgga gtatccatgg    900
agatgtggag ccttgtcacc aacctctaac tgcagaactg ggatgtggag ctggaagtgc    960
ctcctcttct gggctgtgct ggtcacagcc acactctgca ccgctaggcc gtccccgacc   1020
ttgcctgaac aagcccagcc ctggggagcc cctgtggaag tggagtcctt cctggtccac   1080
cccggtgacc tgctgcagct tcgctgtcgg ctgcgggacg atgtgcagag catcaactgg   1140
ctgcgggacg gggtgcagct ggcggaaagc aaccgcaccc gcatcacagg ggaggaggtg   1200
gaggtgcagg actccgtgcc cgcagactcc ggcctctatg cttgcgtaac cagcagcccc   1260
tcgggcagtg acaccaccta cttctccgtc aatgtttcag atgctctccc ctcctcggag   1320
gatgatgatg atgatgatga ctcctcttca gaggagaaag aaacagataa caccaaacca   1380
aaccccgtag ctccatattg gacatcccca gaaaagatgg aaaagaaatt gcatgcagtg   1440
ccggctgcca agacagtgaa gttcaaatgc ccttccagtg ggaccccaaa ccccacactg   1500
cgctggttga aaaatggcaa agaattcaaa cctgaccaca gaattggagg ctacaaggtc   1560
cgttatgcca cctggagcat cataatggac tctgtggtgc cctctgacaa gggcaactac   1620
acctgcattg tggagaatga gtacggcagc atcaaccaca catccagct ggatgtcgtg   1680
gagcggtccc ctcaccggcc catcctgcaa gcagggttgc ccgccaacaa aacagtggcc   1740
ctgggtagca acgtggagtt catgtgtaag gtgtacagtg accgcagcc gcacatccag   1800
tggctaaagc acatcgaggt gaatgggagc aagattggcc cagacaacct gccttatgtc   1860
cagatcttga agactgctgg agttaatacc accgacaaag agatggaggt gcttcactta   1920
agaaatgtct cctttgagga cgcaggggag tatacgtgct ggcgggtaa ctctatcgga   1980
ctctcccatc actctgcatg gttgaccgtt ctggaagccc tggaagagag gccggcagtg   2040
atgacctcgc ccctgtacct ggagatcatc atctattgca caggggcctt cctcatctcc   2100
tgcatggtgg ggtcggtcat cgtctacaag atgaagagtg gtaccaagaa gagtgacttc   2160
cacagccaga tggctgtgca caagctggcc aagagcatcc ctctgcgcag acaggtaaca   2220
gtgtctgctg actccagtgc atccatgaac tctggggttc ttctggttcg gccatcacgg   2280
ctctcctcca gtgggactcc catgctagca ggggtctctg agtatgagct tcccgaagac   2340
cctcgctggg agctgcctcg ggacagactg gtcttaggca acccctggg agagggctgc   2400
tttgggcagg tggtgttggc agaggctatc gggctggaca aggacaaacc caaccgtgtg   2460
accaaagtgg ctgtgaagat gttgaagtcg gacgcaacag agaaagactt gtcagacctg   2520
atctcagaaa tggagatgat gaagatgatc gggaagcata agaatatcat caacctgctg   2580
ggggcctgca gcaggatgg tcccttgtat gtcatcgtgg agtatgcctc caagggcaac   2640
ctgcgggagt acctgcaggc ccggaggccc ccagggctgg aatactgcta caaccccagc   2700
cacaacccag aggagcagct ctcctccaag gacctggtgt cctgcgccta ccaggtggcc   2760
cgaggcatgg agtatctggc ctccaagaag tgcatacacc gagacctggc agccaggaat   2820
gtcctggtga cagaggacaa tgtgatgaag atagcagact ttggcctcgc acgggacatt   2880
caccacatcg actactataa aaagacaacc aacggccgac tgcctgtgaa gtggatggca   2940
cccgaggcat tatttgaccg gatctacacc caccagagtg atgtgtggtc tttcggggtg   3000
ctcctgtggg agatcttcac tctgggcggc tccccatacc ccggtgtgcc tgtggaggaa   3060
cttttcaagc tgctgaagga gggtcaccgc atggacaagc cagtaactg caccaacgag   3120
ctgtacatga tgatgcggga ctgctggcat gcagtgccct cacagagacc caccttcaag   3180
```

```
cagctggtgg aagacctgga ccgcatcgtg gccttgacct ccaaccagga gtacctggac    3240
ctgtccatgc ccctggacca gtactccccc agctttcccg acacccggag ctctacgtgc    3300
tcctcagggg aggattccgt cttctctcat gagccgctgc cgaggagcc ctgcctgccc     3360 cgacacccag cccagcttgc caatggcgga ctcaaacgcc gctgactgcc acccacacgc    3420
cctccccaga ctccaccgtc agctgtaacc ctcacccaca gccctgctg ggcccaccac     3480 ctgtccgtcc ctgtcccctt tcctgctggc aggagccggc tgcctaccag gggccttcct   3540
gtgtggcctg ccttcacccc actcagctca cctctccctc cacctcctct ccacctgctg   3600
gtgagaggtg caaagaggca gatctttgct gccagccact tcatcccctc ccagatgttg   3660
gaccaacacc cctccctgcc accaggcact gcctggaggg cagggagtgg gagccaatga   3720
acaggcatgc aagtgagagc ttcctgagct ttctcctgtc ggtttggtct gttttgcctt   3780
cacccataag cccctcgcac tctggtggca ggtgccttgt cctcagggct acagcagtag   3840
ggaggtcagt gcttcgtgcc tcgattgaag gtgacctctg ccccagatag gtggtgccag   3900
tggcttatta attccgatac tagtttgctt tgctgaccaa atgcctggta ccagaggatg   3960
gtgaggcgaa ggccaggttg ggggcagtgt tgtggccctg gggcccagcc ccaaactggg   4020
ggctctgtat atagctatga agaaaacaca aagtgtataa atctgagtat atatttacat   4080 gtcttttttaa aagggtcgtt accagagatt tacccatcgg gtaagatgct cctggtggct   4140
gggaggcatc agttgctata tattaaaaac aaaaaagaaa aaaaggaaa atgttttaa     4200 aaaggtcata tatttttttgc tacttttgct gtttttatttt tttaaattat gttctaaacc  4260
tattttcagt ttaggtccct caataaaaat tgctgctgct tcatttatct atgggctgta   4320
tgaaaagggt gggaatgtcc actggaaaga agggacaccc acgggccctg ggctaggtc    4380 tgtcccgagg gcaccgcatg ctcccggcgc aggttccttg taacctcttc ttcctaggtc   4440
ctgcacccag acctcacgac gcacctcctg cctctccgct gcttttggaa agtcagaaaa   4500
agaagatgtc tgcttcgagg gcaggaaccc catccatgca gtagaggcgc tgggcagaga   4560
gtcaaggccc agcagccatc gaccatggat ggtttcctcc aaggaaaccg gtggggttgg   4620
gctggggagg gggcacctac ctaggaatag ccacggggta gagctacagt gattaagagg   4680
aaagcaaggg cgcggttgct cacgcctgta atcccagcac tttgggacac cgaggtgggc   4740
agatcacttc aggtcaggag tttgagacca gcctggccaa cttagtgaaa ccccatctct   4800
actaaaaatg caaaaattat ccaggcatgg tggcacacgc ctgtaatccc agctccacag   4860
gaggctgagg cagaatccct tgaagctggg aggcggaggt tgcagtgagc cgagattgcg   4920
ccattgcact ccagcctggg caacagagaa acaaaaagg aaaacaaatg atgaaggtct    4980
gcagaaactg aaacccagac atgtgtctgc cccctctatg tgggcatggt tttgccagtg   5040
cttctaagtg caggagaaca tgtcacctga ggctagtttt gcattcaggt ccctggcttc   5100
gtttcttgtt ggtatgcctc cccagatcgt ccttcctgta tccatgtgac cagactgtat   5160
ttgttgggac tgtcgcagat cttggcttct tacagttctt cctgtccaaa ctccatcctg   5220
tccctcagga acggggggaa aattctccga atgtttttgg ttttttggct gcttggaatt   5280
tacttctgcc acctgctggt catcactgtc ctcactaagt ggattctggc tcccccgtac   5340
ctcatggctc aaactaccac tcctcagtcg ctatattaaa gcttatattt tgctggatta   5400
ctgctaaata caaagaaag ttcaatatgt tttcatttct gtagggaaaa tgggattgct    5460
gctttaaatt tctgagctag ggattttttg gcagctgcag tgttggcgac tattgtaaaa   5520
```

-continued

```
ttctctttgt tctctctgt aaatagcacc tgctaacatt acaatttgta tttatgttta    5580
aagaaggcat catttggtga acagaactag gaaatgaatt tttagctctt aaaagcattt    5640
gctttgagac cgcacaggag tgtctttcct tgtaaaacag tgatgataat ttctgccttg    5700
gccctacctt gaagcaatgt tgtgtgaagg gatgaagaat ctaaaagtct tcataagtcc    5760
ttgggagagg tgctagaaaa atataaggca ctatcataat tacagtgatg tccttgctgt    5820
tactactcaa atcacccaca aatttcccca aagactgcgc tagctgtcaa ataaaagaca    5880
gtgaaattga cctgaaaaaa aaaaaaaaaa a                                   5911

<210> SEQ ID NO 14
<211> LENGTH: 23
<212> TYPE: RNA
<213> ORGANISM: Homo sapiens

<400> SEQUENCE: 14
uaauguuaua ucugaugcug cua                                            23

<210> SEQ ID NO 15
<211> LENGTH: 23
<212> TYPE: RNA
<213> ORGANISM: Homo sapiens

<400> SEQUENCE: 15 ucaaccccc gacugugcug cuc                                             23

<210> SEQ ID NO 16
<211> LENGTH: 23
<212> TYPE: RNA
<213> ORGANISM: Homo sapiens

<400> SEQUENCE: 16 ccauuucuu auugcgcugc uac                                             23

<210> SEQ ID NO 17
<211> LENGTH: 23
<212> TYPE: RNA
<213> ORGANISM: Homo sapiens

<400> SEQUENCE: 17
cucuuucaca uuguuugcug cua                                            23

<210> SEQ ID NO 18
<211> LENGTH: 23
<212> TYPE: RNA
<213> ORGANISM: Homo sapiens

<400> SEQUENCE: 18
uaauuuaaaa uauuuugcug cua                                            23

<210> SEQ ID NO 19
<211> LENGTH: 23
<212> TYPE: RNA
<213> ORGANISM: Homo sapiens

<400> SEQUENCE: 19
gaagaaucuu acagaugcug cua                                            23

<210> SEQ ID NO 20
<211> LENGTH: 23
<212> TYPE: RNA
<213> ORGANISM: Homo sapiens
```

```
<400> SEQUENCE: 20
ucccucaaua aaaauugcug cug                                              23

<210> SEQ ID NO 21
<211> LENGTH: 23
<212> TYPE: RNA
<213> ORGANISM: Homo sapiens

<400> SEQUENCE: 21
cucaauaaaa auugcugcug cuu                                              23

<210> SEQ ID NO 22
<211> LENGTH: 64
<212> TYPE: DNA
<213> ORGANISM: artificial
<220> FEATURE:
<223> OTHER INFORMATION: antagomir for miRs 15 and 16

<400> SEQUENCE: 22
gcacaaacca ttatgtgctg ctaagagaac ttagagaact tcacaaacca ttatgtgctg      60
ctat                                                                   64

<210> SEQ ID NO 23
<211> LENGTH: 62
<212> TYPE: DNA
<213> ORGANISM: artificial
<220> FEATURE:
<223> OTHER INFORMATION: antagomir for miR 21

<400> SEQUENCE: 23
tcaacatcag tctgataagc taagagaact tagagaactt tcaacatcag tctgataagc      60
ta                                                                     62

<210> SEQ ID NO 24
<211> LENGTH: 22
<212> TYPE: RNA
<213> ORGANISM: Homo sapiens

<400> SEQUENCE: 24
uagcuuauca gacugauguu ga                                               22

<210> SEQ ID NO 25
<211> LENGTH: 2718
<212> TYPE: DNA
<213> ORGANISM: Homo sapiens

<400> SEQUENCE: 25
cagggtaacg ctgtcttgtg gacccgcact tcccacccga gacctctcac tgagcccgag      60
ccgcgcgcga catgagccac gggaagggaa ccgacatgct cccggagatc gccgccgccg     120
tgggcttcct ctccagcctc ctgaggaccc ggggctgcgt gagcgagcag aggcttaagg     180
tcttcagcgg ggcgctccag gaggcactca gagcacta caaacaccac tggtttcccg       240
aaaagccgtc caagggctcc ggctaccgct gcattcgcat caaccacaag atggacccca     300
tcatcagcag ggtggccagc cagatcggac tcagccagcc ccagctgcac cagctgctgc     360
ccagcgagct gaccctgtgg gtggaccccct atgaggtgtc ctaccgcatt ggggaggacg     420
gctccatctg cgtcttgtac gaggaggccc cactggccgc ctcctgtggg ctcctcacct     480
gcaagaacca agtgctgctg ggccggagca gcccctccaa gaactacgtg atggcagtct     540
```

-continued

```
ccagctaggc ccttccgccc ccgccctggg cgccgccgtg ctcatgctgc cgtgacaaca    600
ggccaccaca tacctcaacc tggggaactg tattttaaa tgaagagcta tttatatata    660
ttattttttt ttaagaaagg aggaaaagaa accaaaagtt ttttttaaga aaaaaatcc    720
ttcaagggag ctgcttggaa gtggcctccc caggtgcctt tggagagaac tgttgcgtgc    780
ttgagtctgt gagccagtgt ctgcctatag gaggggagc tgttaggggg tagacctagc     840
caaggagaag tgggagacgt ttggctagca ccccaggaag atgtgagagg gagcaagcaa    900
ggttagcaac tgtgaacaga gaggtcggga tttgccctgg gggaggaaga gaggccaagt    960
tcagagctct ctgtctcccc cagccagaca cctgcatccc tggctcctct attactcagg   1020
ggcattcatg cctggactta acaatacta tgttatcttt tcttttattt ttctaatgag    1080
gtcctgggca gagagtgaaa aggcctctcc tgattcctac tgtcctaagc tgcttttctt   1140
gaaatcatga cttgtttcta attctaccct caggggcctg tagatgttgc tttccagcca   1200
ggaatctaaa gctttgggtt ttctgagggg gggaggagg gaactggagg ttattggggt    1260
taggatggaa gggaactctg cacaaaacct ttgctttgct agtgctgctt tgtgtgtatg   1320
tgtggcaaat aatttggggg tgatttgcaa tgaaattttg ggacccaaag agtatccact   1380
ggggatgttt tttggccaaa actcttcctt ttggaaccac atgaaagtct tgatgctgct   1440
gccatgatcc ctttgagagg tggctcaaaa gctacaggga actccaggtc ctttattact   1500
gccttctttt caaaagcaca actctcctct aaccctcccc tccccttcc cttctggtcg    1560
ggtcatagag ctaccgtatt ttctaggaca agagttctca gtcactgtgc aatatgcccc   1620
ctgggtccca ggagggtctg gaggaaaact ggctatcaga acctcctgat gccctggtgg   1680
gcttagggaa ccatctctcc tgctctcctt gggatgatgg ctggctagtc agccttgcat   1740
gtattccttg gctgaatggg agagtgcccc atgttctgca agactacttg gtattccttgt   1800
agggccgaca ctaaataaaa gccaaacctt gggcactgtt ttttctccct ggtgctcaga   1860
gcacctgtgg gaaaggttgc tgtctgtctc agtacaatcc aaatttgtcg tagacttgtg   1920
caatatatac tgttgtgggt tggagaaaag tggaaagcta cactgggaag aaactcccctt  1980
ccttcaattt ctcagtgaca ttgatgaggg gtcctcaaaa gacctcgagt ttcccaaacc   2040
gaatcacctt aagaaggaca gggctagggc atttggccag gatggccacc ctcctgctgt   2100
tgccccttag tgaggaatct tcaccccact tcctctaccc caggttctc ctccccacag    2160
ccagtcccct ttcctggatt tctaaactgc tcaattttga ctcaaaggtg ctatttacca   2220
aacactctcc ctaccattc ctgccagctc tgcctccttt tcaactctcc acattttgta    2280
ttgccttccc agacctgctt ccagtcttta ttgctttaaa gttcactttg ggcccacaga   2340
cccaagagct aattttctgg tttgtgggtt gaaacaaagc tgtgaatcac tgcaggctgt   2400
gttcttgcat cttgtctgca aacaggtccc tgccttttta gaagcagcct catggtctca   2460
tgcttaatct tgtctctctt ctcttcttta tgatgttcac tttaaaaaca acaaaacccc   2520
tgagctggac tgttgagcag gcctgtctct cctattaagt aaaaataaat agtagtagta   2580
tgtttgtaag ctattctgac agaaaagaca aaggttacta attgtatgat agtgttttta   2640
tatggaagaa tgtacagctt atggacaaat gtacacctttt ttgttacttt aataaaaatg   2700
tagtaggata aaaaaaaa                                                  2718
```

<210> SEQ ID NO 26
<211> LENGTH: 39
<212> TYPE: DNA
<213> ORGANISM: Homo sapiens

```
<400> SEQUENCE: 26
atcaaccccc cgactgtgct gctcgcgaag gtcccacag                              39

<210> SEQ ID NO 27
<211> LENGTH: 39
<212> TYPE: DNA
<213> ORGANISM: Homo sapiens

<400> SEQUENCE: 27
atcaaccccc cgactgttaa tttcgcgaag gtcccacag                              39

<210> SEQ ID NO 28
<211> LENGTH: 39
<212> TYPE: DNA
<213> ORGANISM: Homo sapiens

<400> SEQUENCE: 28
ttaatgttat atctgatgct gctatatcca ctgtccaac                              39

<210> SEQ ID NO 29
<211> LENGTH: 39
<212> TYPE: DNA
<213> ORGANISM: Homo sapiens

<400> SEQUENCE: 29
ttaatgttat atctgattaa tttatatcca ctgtccaac                              39

<210> SEQ ID NO 30
<211> LENGTH: 39
<212> TYPE: DNA
<213> ORGANISM: Homo sapiens

<400> SEQUENCE: 30
tctctttcac attgtttgct gctattggag gatcagttt                              39

<210> SEQ ID NO 31
<211> LENGTH: 39
<212> TYPE: DNA
<213> ORGANISM: Homo sapiens

<400> SEQUENCE: 31
tctctttcac attgtttaaa tatattggag gatcagttt                              39

<210> SEQ ID NO 32
<211> LENGTH: 39
<212> TYPE: DNA
<213> ORGANISM: Homo sapiens

<400> SEQUENCE: 32
ctccattttc ttattgcgct gctaccgttg acttccagg                              39

<210> SEQ ID NO 33
<211> LENGTH: 39
<212> TYPE: DNA
<213> ORGANISM: Homo sapiens

<400> SEQUENCE: 33
ctccattttc ttattgctaa tttaccgttg acttccagg                              39
```